United States Patent
Fong et al.

(10) Patent No.: US 10,260,044 B1
(45) Date of Patent: *Apr. 16, 2019

(54) METHODS OF EXPANDING MYELOID CELL POPULATIONS AND USES THEREOF

(71) Applicant: Cellerant Therapeutics, Inc., San Carlos, CA (US)

(72) Inventors: Timothy C. Fong, Moraga, CA (US); Adrianus Geertrudis Wilhelmus Domen, Kansas City, KS (US); Julie Lynne Christensen, Boulder Creek, CA (US)

(73) Assignee: CELLERANT THERAPEUTIC, INC., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/155,598

(22) Filed: Oct. 9, 2018

Related U.S. Application Data

(60) Continuation of application No. 14/481,715, filed on Sep. 9, 2014, now abandoned, which is a division of application No. 13/540,471, filed on Jul. 2, 2012, now Pat. No. 8,877,495, which is a division of application No. 11/259,592, filed on Oct. 25, 2005, now Pat. No. 8,252,587.

(60) Provisional application No. 60/622,318, filed on Oct. 25, 2004.

(51) Int. Cl.
| | |
|---|---|
| *C12N 5/078* | (2010.01) |
| *C12N 5/0789* | (2010.01) |
| *A61K 9/10* | (2006.01) |
| *A61K 35/15* | (2015.01) |
| *A61K 35/28* | (2015.01) |
| *A61K 9/00* | (2006.01) |
| *A61K 35/12* | (2015.01) |

(52) U.S. Cl.
CPC .......... *C12N 5/0647* (2013.01); *A61K 9/0014* (2013.01); *A61K 9/10* (2013.01); *A61K 35/12* (2013.01); *A61K 35/15* (2013.01); *A61K 35/28* (2013.01); *A61K 2035/124* (2013.01); *C12N 2500/44* (2013.01); *C12N 2500/90* (2013.01); *C12N 2500/99* (2013.01); *C12N 2501/125* (2013.01); *C12N 2501/145* (2013.01); *C12N 2501/22* (2013.01); *C12N 2501/23* (2013.01); *C12N 2501/2303* (2013.01); *C12N 2501/26* (2013.01); *C12N 2501/727* (2013.01)

(58) Field of Classification Search
None
See application file for complete search history.

(56) References Cited

U.S. PATENT DOCUMENTS

| | | |
|---|---|---|
| 5,137,809 A | 8/1992 | Loken et al. |
| 5,199,942 A | 4/1993 | Gillis |
| 5,750,397 A | 5/1998 | Tsukamoto et al. |
| 5,772,992 A | 6/1998 | Bauer et al. |
| 5,808,002 A | 9/1998 | Buhring |
| 5,821,108 A | 10/1998 | Akashi et al. |
| 5,840,580 A | 11/1998 | Terstappen et al. |
| 5,843,633 A | 12/1998 | Yin et al. |
| 5,877,299 A | 3/1999 | Thomas et al. |
| 5,879,940 A | 3/1999 | Torok-Storb et al. |
| 5,905,041 A | 5/1999 | Beug et al. |
| 5,986,049 A | 11/1999 | Forstrom et al. |
| 5,989,537 A | 11/1999 | Holly et al. |
| 5,997,860 A | 12/1999 | Bauer et al. |
| 6,013,067 A | 1/2000 | Fibbe et al. |
| 6,030,836 A | 2/2000 | Thiede et al. |
| 6,326,198 B1 | 12/2001 | Emerson et al. |
| 6,335,195 B1 | 1/2002 | Rodgers et al. |
| 6,338,942 B2 | 1/2002 | Kraus et al. |
| 6,433,142 B1 | 8/2002 | Turner et al. |
| 6,465,247 B1 | 10/2002 | Weissman et al. |
| 6,465,249 B2 | 10/2002 | Reya et al. |
| 6,558,662 B2 | 5/2003 | Sykes et al. |
| 6,589,759 B1 | 7/2003 | Loscalzo et al. |
| 6,733,746 B2 | 5/2004 | Daley et al. |
| 6,761,883 B2 | 7/2004 | Weissman et al. |
| 6,967,029 B1 | 11/2005 | Zsebo et al. |
| 6,982,082 B1 | 1/2006 | Schreiber et al. |
| 7,618,654 B2 | 11/2009 | Weissman et al. |
| 7,811,815 B2 | 10/2010 | Brown |
| 8,383,095 B2 | 2/2013 | Christensen et al. |
| 2003/0060425 A1 | 3/2003 | Ahlem et al. |

(Continued)

FOREIGN PATENT DOCUMENTS

| | | |
|---|---|---|
| WO | 94/001534 A1 | 1/1994 |
| WO | 99/010478 A1 | 3/1999 |

(Continued)

OTHER PUBLICATIONS

Aggarwal, et al., "Human mesenchymal stem cells modulate allogeneic immune cell responses," *Blood*, vol. 105(4), pp. 1815-1822 (Feb. 15, 2005).

Akahori, et al., "Effects of pegylated recombinant human megakaryocyte growth and development factor on thrombocytopenia induced by a new myelosuppressive chemotherapy regimen in mice," *Stem Cells*, vol. 14(6), pp. 678-689 (Nov. 1996).

Akashi, "A clonogenic common myeloid progenitor that gives rise to all myeloid lineages," *Nature*, vol. 404(6774), pp. 193-197 (Mar. 2000).

Akashi, et al., "Bcl-2 rescues T lymphopoiesis in interleukin-7 receptor-deficient mice," *Cell*, vol. 89(7), pp. 1033-1041 (1997).

(Continued)

*Primary Examiner* — Laura Schuberg
(74) *Attorney, Agent, or Firm* — Kilpatrick Townsend & Stockton LLP

(57) ABSTRACT

The present disclosure relates to a method of expanding myeloid progenitor cells by culturing an initial population of cells in a medium comprising a mixture of cytokines and growth factors that promote growth and expansion of the myeloid progenitor cells. The expanded cell population provides a source of cells as therapeutic treatments for neutropenia and/or thrombocytopenia arising in patients subjected to myeloablative therapy and hematopoietic stem cell transplantation.

20 Claims, 26 Drawing Sheets

(56) References Cited

U.S. PATENT DOCUMENTS

| | | |
|---|---|---|
| 2003/0180269 A1 | 9/2003 | Hariri |
| 2004/0241856 A1 | 12/2004 | Cooke |
| 2005/0118147 A1 | 6/2005 | Oh |
| 2005/0215473 A1 | 9/2005 | Alvarez et al. |
| 2006/0134783 A1 | 6/2006 | Fong et al. |
| 2006/0222625 A1 | 10/2006 | Brown |
| 2007/0237752 A1 | 10/2007 | Christensen et al. |
| 2013/0004468 A1 | 1/2013 | Fong et al. |
| 2013/0089527 A1 | 4/2013 | Fong et al. |
| 2014/0377234 A1 | 12/2014 | Fong et al. |

FOREIGN PATENT DOCUMENTS

| | | | |
|---|---|---|---|
| WO | 99/40180 | A2 | 8/1999 |
| WO | 00/70022 | A2 | 11/2000 |
| WO | 01/00019 | A | 1/2001 |
| WO | 2004/024875 | A2 | 3/2004 |
| WO | 2004/046312 | A | 6/2004 |
| WO | 2004/071443 | A | 8/2004 |

OTHER PUBLICATIONS

Akashi, et al., "Lymphoid development from hematopoietic stem cells," *Int. J. Hematol.*, vol. 69(4), pp. 217-226 (Jun. 1999).

Akashi, et al., "Prospective Isolation of a Progenitor Common to all Myeloid Lineages and its Lineal Descendant Myelomonocytic and Erythroid/Megakaryocytic Progenitors," *Blood*, 94 (10, Suppl. 1 Part 1):377a (1999).

Akashi, et al., "Transcriptional accessibility for genes of multiple tissues and hematopoietic lineages is hierarchically controlled during early hematopoiesis," *Blood*, vol. 101(2), pp. 383-390 (Jan. 2003) (first pub'd online Sep. 5, 2002).

Antoni, et al., "A short synthetic peptide fragment of human interleukin 1 with immunostimulatory but not inflammatory activity," *J. Immunol.*, vol. 137(10), pp. 3201-3204 (Nov. 1986).

Arber, et al., "MHC-mismatched murine committed myeloid progenitors engraft and protect against invasive aspergillosis", Stanford University School of Medicine, Dept. of Medicine, Divisions of Bone Marrow Transplantation and Infectious Diseases, Stanford CA 94305 USA, Abstract published in *Blood*, Nov. 16, 2003. Poster presented Dec. 8, 2003 at ASH.

Arber, et al., "Protection against Lethal *Aspergillus fumigatus* Infection in Mice by Allogenic Myeloid Progenitors is Not Major Histocompatibility Complex Restricted," *J Infect Dis.*, vol. 192(9), pp. 1666-1671 (2005).

Arbor, et al., "Common lymphoid progenitors from MHC-mismatched donors engraft without inducing GVHD," *Blood*, 102:3504 (2003).

Barbone, et al., "New epoetin molecules and novel therapeutic approaches," *Nephrol. Dial Transplant.*, vol. 14(Supp. 2), pp. 80-84 (1999).

Barker, J. et al., "Impact of Multiple Unit Unrelated Donor Umbilical Cord Blood Transplantation in Adults: Preliminary Analysis of Safety and Efficacy", *Blood, Grune & Stratton*, 98, No. 11, abstract 2791, pp. 666a (2001).

Barry, et al., "Two contiguous residues in human interleukin-3, Asp$^{21}$ and Glu$^{22}$ selectively interact with the α- and β-chains of its receptor and participate in function," *J. Biol. Chem.*, 269(11), pp. 8488-8492 (Mar. 1994).

Bartley, et al., "Identification and cloning of a megakaryocyte growth and development factor that is a ligand for the cytokine receptor MPL," *Cell*, 77(7), pp. 1117-1124 (Jul. 1994).

Baust et al., "Cryopreservation an emerging paradigm change," *Organogenesis*, 5(3), pp. 90-96 (2009).

Beilhack, G. et al., "Prevention of Type I Diabetes with Major Histocompatibility Complex-Compatible and Nonmarrow Ablative Hematopoietic Stem Cell Transplants"; *Diabetes*, 54, pp. 1770-1779 (2005).

Bender, et al, "Phenotypic analysis and characterization of CD34+ cells from normal human bone marrow, cord. blood, peripheral blood and mobilized peripheral blood from patients undergoing autologous stem cell transplantation", *Clinical Immunology and Immunopathology*, 70, No. 1, pp. 1-18, (1994).

Bender, et al., "Characterization of chemotherapy mobilized peripheral blood progenitor cells for use in autologous stem cell transplantation," *Bone Marrow Transplantation*, 10, pp. 281-285 (1992).

Bender, et al., "Identification and Comparison of CD34-Positive Cells and Their Subpopulations From Normal Peripheral Blood and Bone Marrow Using Multicolor Flow Cytometry," *Blood*, 77, No. 12, pp. 2591-2596 (1991).

Bertolini, et al., "Comparative study of different procedures for the collection and banking of umbilical cord blood," *J. Hematother.*, 4(1), pp. 29-36 (Feb. 1995).

Bhatia, et al., "Quantitative analysis reveals expansion of human hematopoietic repopulating cells alter short term ex vivo culture," *J. Exp. Med.*, 186(4), pp. 619-624 (Aug. 1997).

Bitmansour, et al. "Myeloid progenitors protect against invasive aspergillosis and Pseudomonas aeruginosa infection following hematopoietic stem cell transplantation", *Blood*, 100, No. 13, pp. 4660-4667 (Dec. 15, 2002).

Bittencourt, et al., "Association of CD34 cell dose with hematopoietic recovery, infections, and other outcomes after HLA-identical sibling bone marrow transplantation," *Blood*, 99, No. 8, pp. 2726-2733 (2002).

Blair, et al., "Ex vivo expansion of megakaryocyte progenitor cells from normal bone marrow and peripheral blood and from patients with haematological malignancies"; *British Journal of Hematology*, 116, pp. 912-919 (2002).

Boissel, et al., "Erythropoietin structure-function relationships: Mutant proteins that test a model of tertiary structure," *J. Bioi. Cham.* 268(21):15983-15993 (Jul. 1993).

Booth, et al., "Protection against mucosal injury by growth factors and cytokines," *J. Natl. Cancer Inst. Monogr.*, 29, pp. 16-20 (2001).

Boraschi, et al., "Structure-function relationship in the IL-1 family," *Front. Biosci.*, 1, pp. 270-308 (Oct. 1996).

Broudy, •stem cell factor and hematopoiesis, *Blood*, 90(4), 1345-1364 (Aug. 1997).

Broxmeyer, et al., "High-efficiency recovery of functional hematopoietic progenitor and stem cells from C15 human cord blood cryopreserved for 15 years," *Proc. Na/l. Acad. Sci. SA*, 100(2), pp. 645-650 (Jan. 2003) (first pub'd online 01/0712003).

Burger, "Cloning and expression of interleukin-3 genes of chimpanzee and new world monkeys," *Biochim. Blophys. Acta*, 1217(2), pp. 195-198 (Mar. 1994).

Cairo, et al., "Circulating granulocyte colony-stimulating factor (G-CSF) levels after allogeneic and autologous bone marrow transplantation: endogenous C-CSF production correlates with myeloid engraftment," *Blood*, 79, pp. 1869-1873 (1992).

Chardon, et al., "The porcine major histocompatibility complex and related paralogous regions:.a review," *Genet. Sel. Evo.*, 32(2), pp. 109-128 (Mar.-Apr. 2000).

Chen Yu et al., "Study on Nonmyeloablative Bone Marrow Transplantation", Fudan University Journal of Medical Sciences, vol. 31, No. 5, Sep. 30, 2004, pp. 518-520.

Chiu, et al., "Multiple biological activities are expressed by a mouse interleukin 6 eDNA clone isolated from bone marrow stromal cells," *Proc. Nat/. Acad. Sci. USA*, 85, 19, pp. 7099-7103 (Oct. 1988).

Christensen, et al., "Flk-2 is a marker in hematopoietic stem cell differentiation: a simple method to Isolate long-term stem cells," *Proc. Natl. Acad. Sci. USA*, 98(25), pp. 14561-14568 (Dec. 2001) (first pub'd online 11/2712001).

Cohen, et al., Cloning and expression of the rat interleukin-'3 gene, *Nucleic Acids-Res.*, 14(9), pp. 3641-3658 (May 1986).

Coutinho, et al., "Clonal and long term bone marrow cultures using human bone marrow," In *Haemotology: A Practical Approach*, N. Testa, et al. (eds.); Oxford University Press: Oxford, GB (1992).

Curtis, et al., "Enhanced hematopoietic activity of a human granulocyte/macrophage colony-stimulatingfactor-interleukin 3 fusion protein," *Proc. Natl. Acad. Sci. USA*, 88(13), pp. 5809-5813 (Jul. 1991).

(56) References Cited

OTHER PUBLICATIONS

Dagan, et al., "High-level expression and production of recombinant human interleukin-6 analogs:" *Protein Expr; Purif.*, 3(4), pp. 290-294 (Aug. 1992).
Dasgupta, et al., "Methods of stem cell mobilization," *J. Infusional Chemother.*, 6(1), pp. 12-16 (1996).
David, et al., "The porcine erythropoietin gene: cDNA sequence, genomic sequence and expression analyses in piglets," *Domes. Anim. Endocrinol.*, 20(2), pp. 137-147 (Feb. 2001).
Devine, et al., "Clinical application of hematopoietic progenitor cell expansion: current status and future prospects," *Bone Marrow Transplant*, 31(4), pp. 241-252 (Feb. 2003).
Dexter, et al., Conditions controlling the proliferation of haemopoietic stem cells in vitro, • *J. Cell Physiol.*, 91(3), pp. 335-344 (Jun. 1977).
Drayer, et al., "The in vitro effects of cytokines on expansion and migration of megakaryocyte progenitors"; *British Journal of Hematology*, 109, pp. 776-784 (2000).
Droogmans, et al., "Nucleotide sequence of bovine interleukin-6 eDNA," *DNA Seq*, 2(6), pp. 411-413 (1992).
Dunham, et al., "Isolation, nucleotide sequence and expression of a cDNA encoding feline granulocyte colony-stimulating factor," *Cytokine*, 14(6), pp. 347-351 (Jun. 2001).
Ebrahimi, et al., "Cloning, sequencing and expression of the ovine interleukin 6 gene," *Cytokine* 7(3), pp. 232-236 (Apr. 1995).
Ende, et al. "Pooled umbilical cord blood as a possible universal donor for marrow reconstitution and use in nuclear accidents", *Life Sciences*, 69, pp. 1531-1539 (2001).
Enver, et al., "Do Stem Cells Play Dice?" *Blood*, 92(2):348-351 (1998).
Feese, et al., "Structure of the receptor-binding domain of human thrombopoietin determined by complexation with a neutralizing antibody fragment," *Proc. Natl. Acad. Sci. USA* 101(7):1816-1821 (Feb. 2004) (first publ'd online Feb. 9, 2004).
Fernandez, et al., "Unrelated umbilical cord blood transplants in adults: Early recovery of neutrophils by supportive co-transplantation of a low number of highly purified peripheral D blood CD34+ cells from an HLA-haploidentical donor"; *Experimental Hematology*, 31, pp. 535-544 (2003).
Finke et al., "Matched and Mismatched Allogeneic Stem-Cell Transplantation From Unrelated Donors Using Combined Graft-Versus-Host Disease Prophylaxis Including Rabbit Anti—T Lymphocyte Globulin," *Journal of Clinical Oncology*, 21(3), pp. 506-513, (Feb. 1, 2003).
Fisher, "Erythropoietin: physiologic and pharmacologic aspects,"*Proc. Soc. Exp. Biol. Med.* 216(3), pp. 358-369 (Dec. 1997).
Foster, et al., "Human thrombopoietin: gene structure, cDNA sequence, expression, and chromosomal localization," *Proc. Natl. Acad. Sci. USA*, 91(26), pp. 13023-13027 (Dec. 1994).
Fox, et al., "Thrombopoietin expands hematopoietic stem cells after transplantation," *J. Clin. Invest.* 110(3), pp. 387-394 (Aug. 2002).
Fu, et al., "The sheep erythropoietin gene: molecular cloning and effect of hemorrhage on plasma erythropoietin and renal/liver messenger RNA in adult sheep," *Mol. Cell Endocrinol.* 93(2), pp. 107-116 (Jun. 1993).
Fugier-Vivier, 1., et al., "Plasmacytoid precursor dendritic cells facilitate allogenic hematopoietic stem cell engraftment", *J. Experimental Medicine*, 201, No. 3, pp. 373-383 (2005).
Fung, et al. "Molecular cloning of cDNA for murine interleukin-3," *Nature*, 307(5948), pp. 233-237 (Jan. 1984).
Galy, et al., "Human T, B, natural killer, and dendritic cells arise from a common bone marrow progenitor cell subset," *Immunity*, 3(4), pp. 459-473 (Oct. 1995).
Gasson, et al., "Molecular characterization and expression of the gene encoding human erythroid-potentiating activity," *Nature*, 315, 6022, pp. 768-771 (Jun. 1985).
Georgopoulos, et al., "The Role of the Ikaros Gene in Lymphocyte Development and Homeostasis," *Annu. Rev. Immunol.*, 15, pp. 155-176 (1997).
Gill, et al., "Current status of the major histocompatibility complex in the rat," *Transplant Proc.*, 27(2),pp. 1495-1500 (Apr. 1995).
Gluckman, et al., "Factors associated with outcomes of unrelated cord transplant: guidelines for donor choice," *Exp. Hematol.*, 32, pp. 397-407 (2004).
Greiner, et al., "SCID mouse models of Human stem cell engraftment," *Stem Cells*, 16(3), pp. 166-177 (1998).
Grewal, et al., "Unrelated donor hematopoietic cell transplantation: marrow or umbilical cord blood?" *Blood*, 101:11, pp. 4233-4244 (2003).
Gronenborn, et al., "A 1H-NMR study of human interleukin-1 beta. Sequence-specific assignment of aromatic residues using site-directed mutant proteins," *Eur. J. Biochem.*, 161(1), pp. 37-43 (Nov. 1986).
Gryn, J., et al. "Multiple Unmatched Umbilical Cord Units (MUCs) for adult allogenic transplantation" *Blood, Grune & Straton*, 98(11), abstract 2792, pp. 666a (2001).
Gurney, et al., Genomic structure, chromosomal localization, and conserved alternative splice forms of thrombopoietin, *Blood*, 85(4), pp. 981-988 (Feb. 1995).
Han, et al., "Cloning and expression of the cDNA encoding rat granulocyte colony-stimulating factor," *Gene* 175(1-2), pp. 101-104 (Oct. 1996).
Harman, B. et al., "Mouse plasmacytoid dendritic cells derive exclusively from estrogen-resistant myeloid progenitors"; *Blood*, 108, No. 3,, pp. 878-885 (2006).
Heidari, et al., "Cloning, sequencing, and analysis of cDNA encoding bovine granulocyte-colony stimulating factor," *Vet. Immunol. Immunopathol,.* 73(2), pp. 183-191 (Feb. 2000).
Heimfeld, et al., "The in vitro Response of Phenotypically Defined Mouse Stem Cells and Myeloerythroid Progenitors to Single or Multiple Growth Factors," *Proc. Natl. Acad. Sci. USA*, 88, pp. 9902-9906 (1991).
Heise, et al., The major histocompatibility complex of primates, *Genetica*, 73(1-2), pp. 53-66 (Aug. 1987).
Henschler, et al., Maintenance of transplantation potential in ex vivo expanded CD34(+)-selected human peripheral blood progenitor cells, *Blood*, 84(9), pp. 2898-2903 (Nov. 1994).
Hill, et al., "The structure of granulocyte-colony-stimulating factor and its relationship to other growth factors," *Proc. Natl. Acad. Sci., USA*, 90(11), pp. 5167-5171 (Jun. 1993).
Hirano, et al., "Complementary DNA for a novel human interleukin (BSF-2) that induces B lymphocytes to produce Immunoglobulin," *Nature*, 324(6092), pp. 73-76 (Nov. 1986).
Howard, et al., "Cloning of equine interleukin 1 alpha and equine interleukin 1 beta and determination of their full-length cDNA sequences," *Am. J. Vet. Res.*, 59(6), pp. 704-711 (Jun. 1998).
Huang, et al., "Muteins of human interleukin-1 that show enhanced bioactivities," *FEBS Lett.*, 223(2), pp. 294-298 (Nov. 1987).
Huether, et al., "Cloning, sequencing and regulation of an mRNA encoding porcine interleukin-1β," *Gene*, 129(2), pp. 285-289 (Jul. 1993).
Iwasaki-Arai, et al., "Enforced granulocyte/macrophage colony-stimulating factor signals do not support lymphopoiesis, but instruct lymphoid to myelomonocytic lineage conversion." *J. Exp. Med.*, 197(10), pp. 1311-1322 (May 2003).
Jagerschmidt, et al., "Human thrombopoietin structure-function relationships: identification of functionally important residues," *Biochem. J,.* 333(Pt. 3), pp. 729-734 (Aug. 1998).
Jaroscak, et al., "Augmentation of umbilical cord blood (UCB) transplantation with ex vivo-expanded UCB cells: results of a phase 1 trial using the AastromReplicell System," *Blood*, vol. 101(12), pp. 5061-5067 (Jun. 15, 2003).
Jones, et al. "Refolding and Oxidation of Recombinant Human stem Cell Factor Produced in *Escherichia coli*", *J. Bio. Chem.*, 271, No. 19, pp. 11301-11308, (1998).
Kanamaru, et al., "Low Numbers of Megakaryocyte Progenitors in Grafts of Cord Blood Cells May Result in Delayed Platelet Recovery After Cord Blood Cell Transplant," *Stem Cells*, 18, No. 3, pp. 190-195 (2000).
Kashiwakura, et al., "Basic fibroblast growth factor-stimulated ex vivo expansion of haematopoietic progenitor cells from human placental and umbilical cord blood," *British Journal of Haematology*, vol. 122(3), pp. 479-488 (2003).

(56) References Cited

OTHER PUBLICATIONS

Kato, et al., "Isolation and characterization of CD34+ hematopoietic stem cells from human peripheral blood by high-gradient magnetic cell sorting," *Cytometry*, 14(4), pp. 384-392 (1993).

Kennedy, et al., "A common precursor for primitive erythropoiesis and definitive haematopoiesis," *Nature*, 386(6624), pp. 488-493 (Apr. 1997).

Ketterer, et al., High CD34+ Cell Counts Decrease Hematologic Toxicity of Autologus Peripheral Blood Progenitor Cell Transplantation, *Blood*, 91, No. 9, pp. 3148-3155 (1998).

Kiel, "SLAM family receptors distinguish hematopoietic stem and progenitor cells and reveal endothelial niches for stem cells," *Cell*, 121(7), pp. 1109-1121 (2005).

Kiessinger, et al., *Exp. Hematol.*, 23, pp. 609-612 (1995).

Kondo, et al., "Identification of clonogenic common lymphoid progenitors in mouse bone marrow," *Cell*, 91(5), pp. 661-672 (Nov. 1997).

Kydd, et al., "Report of the First International Workshop on Equine Leucocyte Antigens, Cambridge, UK, Jul. 1991," *Vet. Immunol. Immunopathol.*, 42(1), pp. 3-60 (Jul. 1994).

Langley, et al., "Properties of variant forms of human stem cell factor recombinantly expressed in *Escherichia coli*," *Arch Biochem. Biophys.*, 311(1), pp. 55-61 (May 1994).

Langley, et al., Purification and characterization of soluble forms of human and rat stem cell factor recombinantly expressed by *Escherichia coli* and by Chinese hamster ovary cells, *Arch. Biochem. Biophys.*, 295(1), pp. 21-28 (May 1992).

Lapidot, et al., "Current understanding of stem cell mobilization: the roles of chemokines, proteolytic enzymes, adhesion molecules, cytokines, and stromal cells," *Exp. Hematol.*, 30(9), pp. 973-981 (Sep. 2002).

Laughlin, et al., "Outcomes after transplantation of cord blood or bone marrow from unrelated donors in adults with leukemia," *N. Eng. J. Med.*, 351:22, pp. 2265-2275 (2004).

Lee, et al., "The pattern of gene expression in human CD15+ myeloid progenitor cells", *Proc. Natl. Acad. Sci. USA*, 2001, vol. 98, No. 6, pp. 3340-3345.

Lee, et al., "Outcomes Research in Hematopoietic Cell Transplantation," *Thomas' Hematopoietic Cell Transplantation*, pp. 434-446 (2004).

Leong, et al., "The nucleotide sequence for the cDNA of bovine interleukin-1β." *Nucleic Acids Res.*, 16(18), 9054 (Sep. 1988).

Lev, et al., "Interspecies molecular chimeras of kit help define the binding site of the stem cell factor," *Mol. Cell. Biol.*, 13(4), pp. 2224-2234 (Apr. 1993).

Lewin, et al., "Comparative organization and function of the major histocompatibility complex of domesticated cattle," *Immunol. Rev.*, 167, pp. 146-158 (Feb. 1999).

Lin, et al., "Cloning and expression of the human erythropoietin gene," *Proc. Natl. Acad. Sci. USA*, 82(22), pp. 7580-7584 (Nov. 1985).

Lin, et al., "Monkey erythropoietin gene: cloning, expression and comparison with the human erythropoietin gene," *Gene*, 44(2-3), pp. 201-209 (1986).

Lin, et al., "Serial granulocyte transfusions as a treatment for sepsis due to multidrug-resistant Pseudomonas aeruginosa in a neutropenic patent." *J. Clin. Microbiol.*, 41(10), pp. 4892-4893 (Oct. 2003).

Lok, et al., "Cloning and expression of murine thrombopoietin cDNA and stimulation of platelet production in vivo," *Nature*, 369(6481), pp. 565-568 (Jun. 1994).

Lok, et al., "The structure, biology and potential therapeutic applications of recombinant thrombopoietin," *Stem Cells*, 12(6), pp. 586-598 (Nov. 1994).

Lopez, et al., "A human interleukin 3 analog with increased biological and binding activities," *Proc. Natl. Acad. Sci. USA*, 89(24), pp. 11842-11846 (Dec. 1992).

Lovejoy, et al., "Crystal structure of canine and bovine granulocyte-colony stimulating factor (G-CSF)," *J. Mol. Biol.*, 234(3), pp. 640-653 (Dec. 1993).

Lu, et al., "Influence in vitro of IL-3/Epo fusion proteins compared with the combination of IL-3 plus Epo in enhancing the proliferation of single isolated erythroid and multipotential progenitor cells from human umbilical cord blood and adult bone marrow," *Exp. Hematol.*, 23(10), pp. 1130-1134 (Sep. 1995).

Lu, et al., "Isolation and characterization of a disulfide-linked human stem cell factor dimer. Biochemical, biophysical, and biological comparison to the noncovalently held dimmer," *J. Biol Chem.*, 271(19), pp. 11301-11316 (May 1996).

Lyman, et al., "Cloning of the human homologue of the murine flt3 ligand: a growth factor for early hematopoietic progenitor cells," *Blood*, 83(10), pp. 2795-2801 (May 1994).

Lyman, et al., "Biology and potential clinical applications of flt3 ligand," *Curr. Opin. Hematol.*, 2(3), pp. 177-181 (May 1995).

Lyman, et al., "Molecular cloning of mast cell growth factor, a hematopoietin that is active in both membrane bound and soluble forms," *Cell*, 75(6), pp. 1157-1167 (Dec. 1993).

Magli, et al., "Transient Nature of Early Hematopoietic Spleen Colonies," *Nature*, 295, pp. 527-529 (1982).

Magro, et al., "Early hematopoietic recovery after single unit unrelated cord blood transplantation in adults supported by co-infusion of mobilized stem cells from a third party donor"; *Haematoligical Hematology Journal*, 91, No. 5. (2006).

Manz, et al., "Prospective isolation of human clonogenic common myeloid progenitors," *Proc. Natl. Acad. Sci. USA*, 99(18), pp. 11872-11877 (Sep. 2002) (first pub'd online Aug. 22, 2002).

March, et al., "Cloning, sequence and expression of two distinct human interleukin-1 complementary DNAs," *Nature*, 315(6021), pp. 641-647 (Jun. 1985).

Martin, et al., "Primary structure and functional expression of rat and human stem call factor DNAs," *Cell*, 63(1), pp. 203-211 (Oct. 1990).

Mavroudis, et al., "CD34+ cell does predicts survival, post-transplant morbidity, and rate of hematologic recovery after allogeneic marrow transplants for hematologic malignancies," *Blood*, vol. 88, No. 8, pp. 3223-3229 (1996).

Mayani, et al., "Characterization of Functionally Distinct Subpopulations of CD34+ Cord Blood Cells in Serum-Free Long-Term Cultures Supplemented with Hematopoietic Cytokines," Blood, vol. 82, No. 9, pp. 2664-2672 (1993).

McClanahan, et al., "Biochemical and genetic characterization of multiple splice variants of the Flt3 ligand," *Blood*, 88(9), pp. 3371-3382 (Nov. 1996).

McCullough, et al., "Effects of storage of granulocytes on their fate in vivo," *Transfusion* 23(1), 20 (Jan.-Feb. 1983).

McInnes, et al., "Cloning of a cDNA encoding bovine interleukin-3," *Gene*, 139(2), pp. 286-290 (Feb. 1994).

McInnes, et al., "The Cloning and Expression of the cDNA for Ovine Stem Cell Factor (Kit-Ligand) and Characterization of its Vitro Haematopoietic Activity", *Cytokine*, 11, No. 4 pp. 249-256 (Apr. 1999).

McNeice, et al., "Ex vivo expanded peripherap blood progenitor cells provide rapid neutrophil recovery after high dose chemotherapy in patients with breast cancer," *Blood*, 96, No. 9 (Nov. 2000).

Metcalf, "Lineage Commitment and Maturation in Hematopoietic Cells: The Case for Extrinsic Regulation," *Blood*, 92(2), pp. 345-352 (1998).

Meyers, et al., "Purification and characterization of human recombinant interleukin-1 β," *J. Biol. Chem.*, 262(23), pp. 11176-11181 (Aug. 1987).

Mickelson, et al., *Hematopoietic Cell Transplantation*, E. Thomas (ed.), Blackwell Scientific Press: Malden, MA, pp. 28-37 (1999).

Middleton, et al., Methods in Molecular Biology: *MHC Protocols* 210, pp. 67-112 (2002).

Miyadai, et al., "Importance of the carboxy-terminus of human interleukin-11 in conserving its biological activity," *Biosci. Biotechnol. Biochem.*, 60(3), pp. 541-542 (Mar. 1996).

Miyamoto, et al., "Myeloid or lymphoid promiscuity as a critical step in hematopoietic lineage commitment," *Dev. Cell*, 3(1), pp. 137-147 (Jul. 2002).

(56) References Cited

OTHER PUBLICATIONS

Miyamoto, et al., "Persistence of Multipotent Progenitors Expressing AML1/ETO Transcripts in Long-Term Remission Patients with t(8;21) Acute Myelogenous Leukemia," *Blood*, 87(11), pp. 4789-4796 (1996).
Montillo, et al., "Successful CD34+ cell mobilization by intermediate-dose Ara-C in chronic lymphocytic leukemia patients treated with sequential fludarabine and Campath-1H," *Leukemia*, 18(1), pp. 57-62 (Jan. 2004).
Morishima, et al., "The clinical significance of human leukocyte antigen (HLA) allele compatibility in patients receiving a marrow transplant from serologically HLA-A, HLA-B, and HLA-DR matched unrelated donors," *Blood*, 99(11), pp. 4200-4206 (Jun. 2002).
Morris, et al., *J. Hematol.*, 120, pp. 413-423 (2003).
Morrison, et al., "The Aging of Hematopoietic Stem Cells," *Nature Medicine*, 2(9), pp. 1011-1016 (1996).
Morrison, et al., "The Long-Term Repopulating Subset of Hematopoietic Stem Cells is Deterministic and Isolatable by Phenotype," *Immunity*, 1, pp. 661-673 (1994).
Mullighan, et al., "Genomic Polymorphism and Allogeneic Hematopoietic Transplantation Outcome"; *American Society for Blood and Marrow Transplantation Biology of Blood Marrow Transplantation*, 12, pp. 19-27 (2006).
Murray, et al., "Optimization of Retroviral Gene Transduction of Mobilized Primitive Hematopoietic Progenitors by Using Thrombopoietin, Flt3, and Kit Ligands and RetroNectin Culture," *Human Gene Therapy*, 10, pp. 1743-1752 (1999).
Mwangi, et al., "Cloning of the bovine interleukin-3-encoding cDNA," *Gene*, 162(2), pp. 309-312 (Sep. 1995).
Nagao, et al., "Nucleotide sequence of rat erythropoietin," *Biochim. Biophys. Acta*, 1171(1), pp. 99-102 (Nov. 1992).
Northemann, et al., "Structure of the rat interleukin 6 gene and its expression in macrophage-derived cells," *J. Biol. Chem.*, 264(27), pp. 16072-16082 (Sep. 1989).
Novelli, et al., "Ex Vivo Culture of Cord Blood CD34+ Cells Expans Progenitor Cell Numbers, Preserves Engraftment Capacity in Nonobese Diabetic/Severe Combined Immunodeficiency Mice, and Enhances Retroviral Transduction Efficiency", *Human Gene Therapy*, 1999, vol. 10, pp. 2927-2940.
O'Brien, et al., "Cloning and sequencing of an ovine granulocyte colony-stimulating factor cDNA," *DNA Seq.*, 4(5), pp. 339-342 (1994).
O'Brien, et al., "Comparative genome organization of the major histocompatibility complex: lessons from the Felidae," *Immunol. Rev.*, 167, pp. 133-144 (Feb. 1999).
O'Doherty, et al., "Dendritic Cells Freshly Isolated from Human Blood Express CD4 and Mature into Typical Immunstimulatory Dendritic cells after Culture in Monocyteconditioned Medium," *J. Exp. Med. Uni. Press*, 178, pp. 1067-1078 (1993).
Ogami, et al., "The sequence of a rat DNA encoding thrombopoietin," *Gene*, 158(2), pp. 309-310 (Jun. 1995).
Ogawa, "Differentiation and Proliferation of Hematopoietic Stem Cells," *Blood*, 81(11), pp. 2844-2853 (1993).
Ohsumi, et al., "Adipogenesis inhibitory factor. A novel inhibitory regulator of adipose conversion in bone marrow," *FEBS Lett.* 288(1-2), pp. 13-16 (Aug. 1991).
Okubo, et al., "Stroma-dependent maintenance of cytokine responsive hematopoietic progenitor cells derived from long-term bone marrow culture," *Cell Struct. Funct.*, 25(2), pp. 133-139 (Apr. 2000).
Olins, et al., "Saturation mutagenesis of human interleukin-3," *J. Biol. Chem.*, 270(40), pp. 23754-23760 (Oct. 1995).
Olivieri, et al., "Factors affecting hemopoietic recovery after high-dose therapy and autologous peripheral blood progenitor cell transplantation: a single center experience," *Haematologica*, 83, pp. 329-337 (1998).
Omerod, *Flow Cytometry: A Practical Approach*, 3d ed., Oxford University Press, General Guidance on Fluorescence Activated Cell Sorting, (2003).

Orita, et al., "Polypeptide and carbohydrate structure of recombinant human interleukin-6 produced in Chinese hamster ovary cells," *J. Biochem.*, 115(2), pp. 345-350 (Feb. 1994).
Orkin, "Development of the Hematopoietic System," *Current Biology*, 6, pp. 597 602 (1996).
Otsuka, et al., "Isolation and characterization of an expressible cDNA encoding human IL-3. Induction of IL-3 mRNA in human T cell clones," *J. Immunol.*, 140(7), pp. 2288-2295 (Apr. 1988).
Palaszvnski, "Synthetic C-terminal peptide of IL-1 functions as a binding domain as well as an antagonist for the IL-1 receptor," *Biochem. Biophys. Res. Commun.*, 147(1), pp. 204-211 (Aug. 1987).
Park, et al., "Identification of functionally important residues of human thrombopoietin," *J. Biol. Chem.*, 273(1), pp. 256-261 (Jan. 1998).
Passegue, et al., "Normal and Leukemic Hematopoiesis: Are leukemias a stem cell disorder or a reacquisition of stem cell characteristics?" *PNAS*, 100, pp. 11842-11849 (2003).
Paul, et al., "Molecular cloning of a cDNA encoding interleukin 11, a stromal cell-derived lymphopoietic and hematopoietic cytokine," *Proc. Natl. Acad. Sci. USA*, 87(19), pp. 7512-7516 (Oct. 1990).
Perkins, et al., "The complete cDNA sequences of IL-2, IL-4, IL-6 and IL-10 from the European rabbit (*Oryctolagus cuniculus*)," *Cytokine*, 12(6), pp. 555-565 (Jun. 2000).
Petersdorf, et al., "Optimizing outcome after unrelated marrow transplantation by comprehensive matching of HLA class I and II alleles in the donor and recipient," *Blood*, 92(10), pp. 3515-2520 (Nov. 1998).
Pevny, et al., "Erythroid Differentiation in Chimaeric Mice Blocked by a Target Mutation in the Gene for Transcription Factor GATA-1," *Nature*, 349, pp. 257-260 (1991).
Pflumio, et al., "Phenotype and function of human hematopoietic cells engrafting immune-deficient CB17-severe combined immunodeficiency mice and nonobese diabetic-severe combined immunodeficiency mice after transplantation of human cord blood mononuclear cells," *Blood*, 88(10):3731 (Nov. 1996).
Piacibello, et al., "Engraftment in nonobese diabetic severe combined immunodeficient mice of human CD34(+) cord blood cells after ex vivo expansion; evidence for the amplification and self-renewal of repopulating stem cells," *Blood*, 93(11), pp. 3736-3749 (Jun. 1999).
Ploemacher, et al., "An in vitro limiting-dilution assay of long-term repopulating hematopoietic stem cells in the mouse," *Blood*, 74(8), pp. 2755-2763 (Dec. 1989).
Priestle, et al., Crystallographic refinement of interleukin 1β at 2.0 a resolution, *Proc. Natl. Acad. Sci. USA*, 86(24), pp. 9667-9671 (Dec. 1989).
Rappold, et al., "Functional and Phenotypic Characterization of Cord Blood and Bone Marrow Subsets Expressing FLT3 (CD135) Receptor Tyrosine Kinase," *Blood*, vol. 90(1), pp. 111-125 (Jul. 1, 1997).
Reichle, et al., Autologous tandem transplantation: almost complete reduction of neutropenic fever following the second transplantation by ex vivo expanded autologous myeloid postprogenitor cells, *Bone Marrow Transplant.*, 32(3), pp. 299-305 (Aug. 2003).
Reiffers, et al., "Abrogation of post-myeloablative chemotherapy neutropenia by ex-vivo expanded autologous CD34-positive cells," *Lancet*, 354(9184), pp. 1092-1093 (Sep. 1999).
Richel, et al., "Highly purified CD34+cells isolated using magnetic activated cell selection provide rapid engraftment following high dose chemotherapy in breast cancer patients", *Bone Marrow Transplantation*, 25, pp. 243-249 (2000).
Rocha, et al., "Transplants of umbilical-cord blood or bone marrow from unrelated donors in adults with acute leukemia," *N. Eng. J. Med.*, 351:22, pp. 2276-2285 (2004).
Rosnet, et al., "Close physical linkage of the FLT1 and FLT3 genes on chromosome 13 in man and chromosome 5 in mouse," *Oncogene*, 8, pp. 173-179 (1993).
Rosnet, et al., "Murine Flt3, a gene encoding a novel tyrosine kinase receptor of the PDGFR/CSFIR family," *Oncogene*, 6, pp. 1641-1650 (1991).

(56) References Cited

OTHER PUBLICATIONS

Rowley et al., "A randomized phase III clinical trial of autologous blood stem cell transplantation comparing cryopreservation using dimethylsulfoxide vs dimethlyslfoxide with hydroxyethylstarch," *Bone Marrow Transplantation*, 31(11), pp. 1043-1051 (Jun. 2003).
Savvides, et al., "Flt3 ligand structure and unexpected commonalities of helical bundles and cystine knots," *Nat. Struct. Biol.*, 7(6), pp. 486-491 (Jun. 2000).
Scheinkonig, et al., "Adoption of long-term cultures to evaluate the cryoprotective potential of trehalose for freezing hematopoietic stem cells," *Bone Marrow Transplant.*, 34(6), pp. 531-536 (Sep. 2004).
Schwarz, et al., "TNF in combination with GM-CSF enhances the differentiation of neonatal cord blood stem cells into dendritic cells and macrophages," *Journal of Leukocyte Biology*, 52, (1992).
Shamblott, et al., "Derivation of pluripotent stem cells from cultured human primordial germ cells," *Proc. Natl. Acad. Sci. USA*, 95:,13726 (1998).
Shanafelt, et al., "Identification of critical regions in mouse granulocyte-macrophage colony-stimulating factor by scanning-delection analysis," *Proc. Natl. Acad. Sci. USA*, 86, pp. 4872-4876 (1989).
Shapiro, et al., "The effects of Flk-2/flt3 ligand as compared with c-kit ligand on short-term and long-term proliferation of CD34+ hematopoietic progenitors elicited from human fetal liver, umbilical cord blood, bone marrow, and mobilized peripheral blood," *J. Hematother.*, 5(6), pp. 655-662 (Dec. 1996).
Shapiro, Practical Flow Cytometry, 4th ed., Wiley-Liss, [General Guidance on Fluorescence Activated Cell Sorting] pp. VII-XXVI (2003).
Shin, et al., "Cloning of canine GM-CSF and SCF genes", *Vet. Sci.*, 2(3), pp. 159-166 (2001).
Shin, et al., *J. Vet. Sci.*, 2(3) pp. 233-237 (1996).
Shinkai, et al., "RAG-2-deficient mice lack mature lymphocytes owing to inability to Initiate V(D)J rearrangement." *Cell*, 68(5), pp. 855-867 (Mar. 1992).
Shivdasani, et al., "A Lineage-Selective Knockout Establishes the Critical Role of Transportation Factor GATA-1 in Megakaryocyte Growth and Platelet Development," *The EMBO Journal*, 16(13)pp. 3965-3973 (1997).
Shizuru, "The Experimental Basis for Hematopoietic Stem Cell Transplantation for Autoimmune Diseases," *Thomas' Hematopoietic Cell Transplantation*, pp. 324-343 (2004).
Shoemaker, et al., "Murine erythropoietin gene: cloning, expression, and human gene homology," *Mol. Cell Biol.*, 6(3), pp. 849-858 (Mar. 1986).
Siminovitch, et al., "The Distribution of Colony-Forming Cells Among Spleen Colonies,"*Journal of Cellular and Comparative Physiology*, 62(3), pp. 327-336 (1963).
Singh, "Gene Targeting Reveals a Hierarchy of Transcription Factors Regulating Specification of Lymphoid Cell Fates," *Current Biology*, 8, pp. 160-165 (1996).
Singhal, et al., "A low CD34+ cell does results in higher mortality and poorer survival after blood or marrow stem cell transplantation from HLA-identical siblings: should be 2×10 CD34+ cells/kg be considered the minimum threshold?" *Bone Marrow Transplantation*, 26, pp. 489-496 (2000).
Sitnicka, et al., "The Effect of Thrombopoietin on the Proliferation and Differentiation of Murin Hematopoietic Stem Cells," *Blood*, W.B. Saunders, Philadelphia, PA, 87, No. 12, pp. 4998-5005 (1996).
Skelly, et al., "High-level expression of a biologically active human interleukin-6 mutein," *J. Biotechnol.*, 34(1), pp. 79-86 (Apr. 1994).
Souyri, et al., "A putative truncated cytokine receptor gene transduced by the myeloproliferative leukemia virus immortalizes hematopoietic progenitors," *Cell*, 63(6), pp. 1137-1147 (Dec. 1990).
Spangrude, et al., "Purification and characterization of mouse hematopoietic stem cells," *Science*, 241(4861), pp. 58-62 (Jul. 1988).
Steinam, "Linking innate to adaptive immunity through dendritic cells"; *Novartis Found Symp.*, 279, pp. 101-109 (2006).
Storms, et al., Isolation of primitive human hematopoietic progenitors on the basis of aldehyde dehydrogenase activity, *Proc. Natl. Acad. Sci. USA*, 96(16), pp. 9118-9123 (Aug. 1999).
Stoyan, et al., "Recombinant soluble human interleukin-6 receptor. Expression in *Escherichia coli*, renaturation and purification." *Eur. J. Biochem.*, 216(1), pp. 239-245 (Aug. 1993).
Suda, et al., "Analysis of Differentiation of Mouse Hematopoietic Stem Cells in Culture by Sequential Replating of Paired Progenitors," *Blood*, 64(2), pp. 393-399 (1984).
Sudo, et al., "Synergistic effect of FLT-3 ligand on the granulocyte colony-stimulating factor-induced mobilization of hematopoietic stem cells and progenitor cells into blood in mice," *Blood*, 89(9), pp. 3186-3191 (May 1997).
Suliman, et al., "Cloning of a cDNA encoding bovine erythropoietin and analysis of its transcription in selected tissues," *Gene* 171(2), pp. 275-280 (Jun. 1996).
Sutherland, et al., "Functional characterization of individual human hematopoietic stem cells cultured at limiting dilution on supportive marrow stromal layers," *Proc. Natl. Acad. Sci. USA*, 87(9), pp. 3584-3588 (May 1990).
Swiderski, et al., "Molecular cloning, sequencing, and expression of equine interleukin-6," *Vet. Immunol. Immunopathol.*, 77(3-4), pp. 213-220 (Dec. 2000).
Szilvassym, et al.,"Quantitation of Murine and Human Hematopoietic Stem Cells by limiting-dilution analysis in competitively repopulated hosts," *Meth in Mod Med.*, 63, Hematopoietic Stem Cell Protocols, C.A. Klug and C.T. Jordan, eds.; Humana Press Inc., Totowas, N.J., pp. 167-187 (2002).
Tacken, et al., "Definition of receptor binding sites on human interleukin-11 by molecular modeling-guided mutagenesis," *Eur. J. Biochem.*, 265(2), pp. 645-655 (Oct. 1999).
Telford, et al., "The murine interleukin 1β gene: structure and evolution," *Nucleic Acids Res.*, 14(24), pp. 9955-9963 (Dec. 1986).
Terskikh, et al., "Gene expression analysis of purified hematopoietic stem cells and committed progenitors," *Blood*, 102(1), pp. 94-101 (Jul. 2003) (first pub'd online Mar. 6, 2003).
Thomson, et al, "Embryonic Stem Cell Lines Derived from Human Blastocysts," *Science*, 282:1145 (1998).
Traver, et al, "Mice Defective in Two Apoptosis Pathways in the Myeloid Lineage Develop Acute Myeloblastic Leukemia," *Immunity*, 9, pp. 47-57 (1998).
Traver, et al., "Fetal liver myelopoiesis occurs through distinct, prospectively isolatable progenitor subsets," *Blood*, 98(3), pp. 627-635 (Aug. 2001).
Tsuchiya, et al., "Isolation and characterization of the cDNA for murine granulocyte colony-stimulating factor," *Proc. Natl. Acad. Sci. USA*, 83(20), pp. 7633-7637 (Oct. 1986).
Turner, et al., "A modified harvest technique for cord blood hematopoietic stem cells," *Bone Marrow Transplant.*, 10(1), pp. 89-91 (Jul. 1992).
Uchida et al, "Rapid and Sustained Hematopoietic Recovery in Lethally Irradiated Mice Transplaned with Purified Thy-1.1.sup.lo Lin.sup.-Sca-1.sup+ Hematopoietic Stem Cells," *Blood*, 83(12), pp. 3758-3779 (1994).
Uchida, et al., "High doses of purified stem cells cause early hematopoietic recovery in syngeneic and allogeneic hosts," *J. Clin. Invest.*, 101(5), pp. 961-966 (Mar. 1998).
Vaughn, Methods in Molecular Biology: *MHC Protocols*, 210, pp. 45-60 (2002).
Vilalta, et al., "Rabbit EPO gene and cDNA: expression of rabbit EPO after intramuscular injection of pDNA," *Biochem. Biophys. Res. Commun.*, 284(3), pp. 823-827 (Jun. 2001).
Wada, et al., "Characterization of the truncated thrombopoietin variants," *Biochem. Biophys. Res. Commun.*, 213(3), pp. 1091-1098 (Aug. 1995).
Wagemaker, et al., "Interleukin-3," *Biotherapy*, 2(4), pp. 337-345 (1990).
Wagner, et al., "Organization of the canine major histocompatibility complex: current perspectives." *J. Hered.*, 90(1), pp. 35-38 (Jan.-Feb. 1999).
Wagner, et al., "Transplantation of unrelated donor umbilical cord blood in 102 patients with malignant and nonmalignant diseases:

(56) References Cited

OTHER PUBLICATIONS influence of CD34 cell does and HLA disparity on treatment-related mortality and survival," *Blood*, 100:1611, pp. 1611-1618 (2002).

Wardley, et al, "Prospective evaluation of oral mucositis in patients receiving myeloablative conditions regimens and haemopoietic progenitor rescue," *British Journal of Haematology*, 110, pp. 292-299 (2000).

Wen, et al., "Erythropoietin structure-function relationships: high degree of sequence homology among mammals." *Blood*, 82(5), pp. 1507-1516 (Sep. 1993).

Wright, et al., "Cyclophosphamide/granulocyte colony-stimulating factor causes selective mobilization of bone marrow hematopoietic stem cells into the blood after M phase of the cell cycle," *Blood*, 97(8), pp. 2278-2285 (Apr. 2001).

Wu et al., "High Efficiency Electroporation of Human Umbilical Cord Blood CD34+ Hematopoietic Precursor Cells," *Stem Cells*, 19, pp. 492-499 (2001).

Yang, et al., "Human IL-3 (multi-CSF): identification by expression cloning of a novel hematopoietic growth factor related to murine IL-3," *Cell*, 47(1), pp. 3-10 (Oct. 1986).

Yang, et al., "Molecular cloning of canine and feline FLT3 ligand reveals high degree of similarity to the human and mouse homologue but uniquely long cytoplasmic domain," *DNA Sequence.*, 11 (1-2), pp. 163-166 (2000).

Yin, et al., "AC133, a novel marker for human hematopoietic stem and progenitor cells," *Blood*, 90(12), pp. 5002-5012 (Dec. 1997).

Young, et al., "Cloning of rabbit interleukin-1 beta: differential evolution of IL-1 α and IL-1 β proteins," *Protein Eng.*, 2(7), pp. 545-551 (May 1989).

Zeigler, et al, "In vitro megakaryocytopoietic and thrombopoietic activity of c-mpl ligand (TPO) on purified murine hematopoietic stem cells," *Blood*, 84, No. 12, pp. 4045-4052 (1994).

Zhang, et al., "Purification and characterization of a recombinant murine interleukin-6. Isolation of N-and C-terminally truncated forms," *Eur. J. Biochem.*, 207(3), pp. 903-913 (Aug. 1992).

Zhang, et al., "Crystal structure of human stem cell factor implication for stem cell factor receptor dimerization and activation," *Proc. Natl. Acad. Sci. USA*, 97(14), pp. 7732-7737 (Jul. 2000).

Zhao, et al., "Overexpression and characterization of recombinant human fusion protein IL-6/IL-2 (CH925)," *Stem Cells*, 12(3), pp. 339-347 (May 1994).

Zimmerman, et al., Clinical impact of ex vivo differentiated myeloid precursors after high-dose chemotherapy and peripheral blood progenitor cell rescue, *Bone Marrow Transplant.*, 26(5), pp. 505-510 (Sep. 2000).

Zon, et al, "Activation of the Erythropoietin Receptor Promoter by Transcription Factor GATA-1,"*Proc. Natl. Acad. Sci. USA*, 88, pp. 10638-10641 (1991).

English translation dated Nov. 22, 2011, from Office Action to Japanese Patent Application No. 2007-538181, 5 pages.

Japanese Office Action for Japanese Patent Application No. 2007-538181, 3 pages, dated Aug. 21, 2012.

The Supplementary European Search Report from EP Appl. No. 12196180.9, dated Apr. 23, 2014.

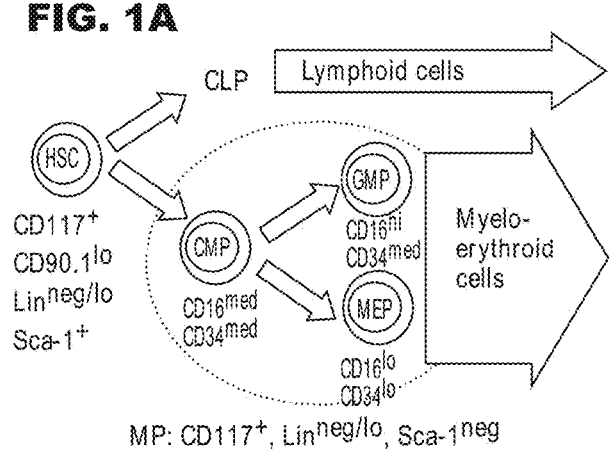
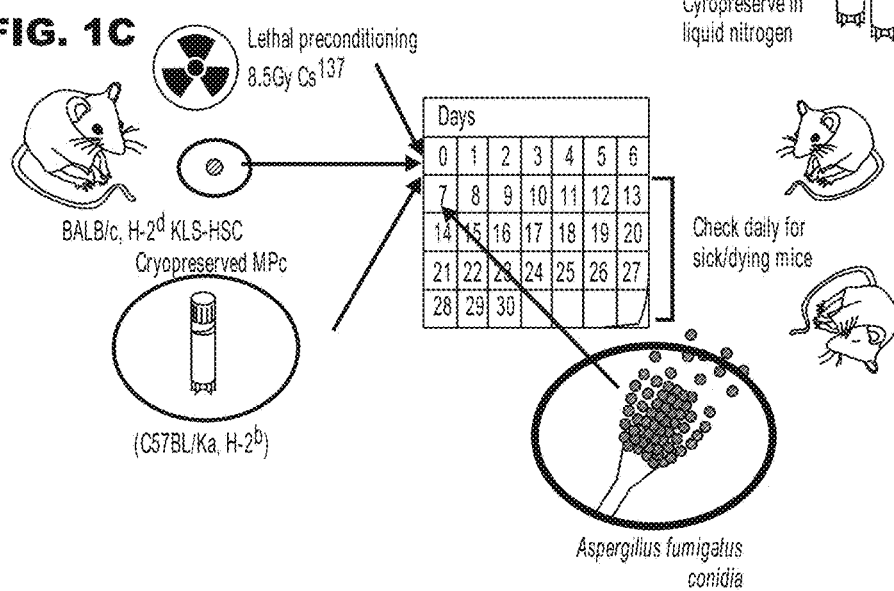

Freshly cultured
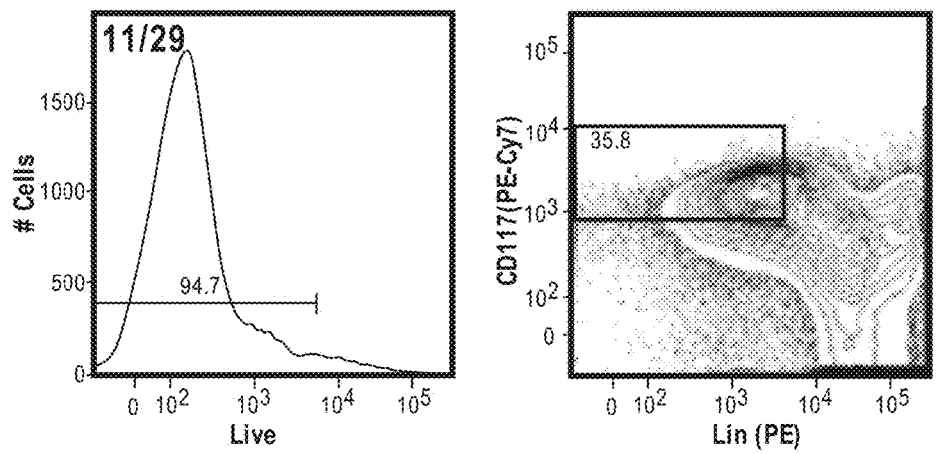
Frozen/thawed
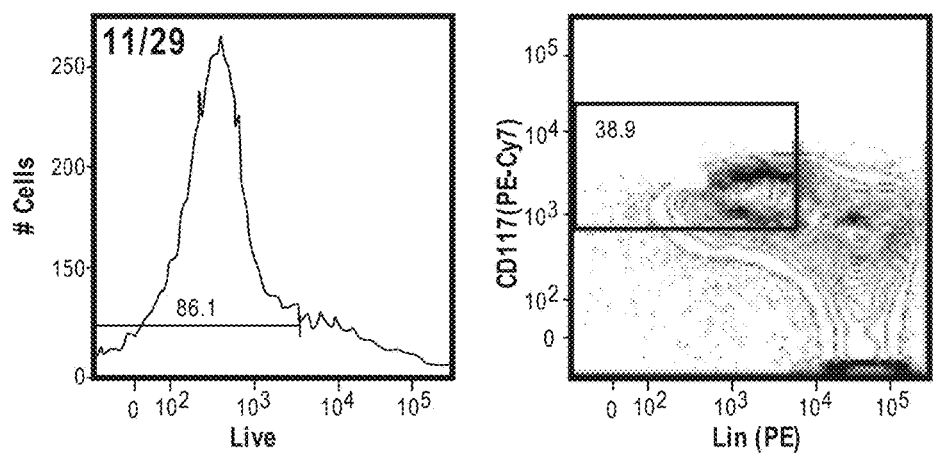
FIG. 4B

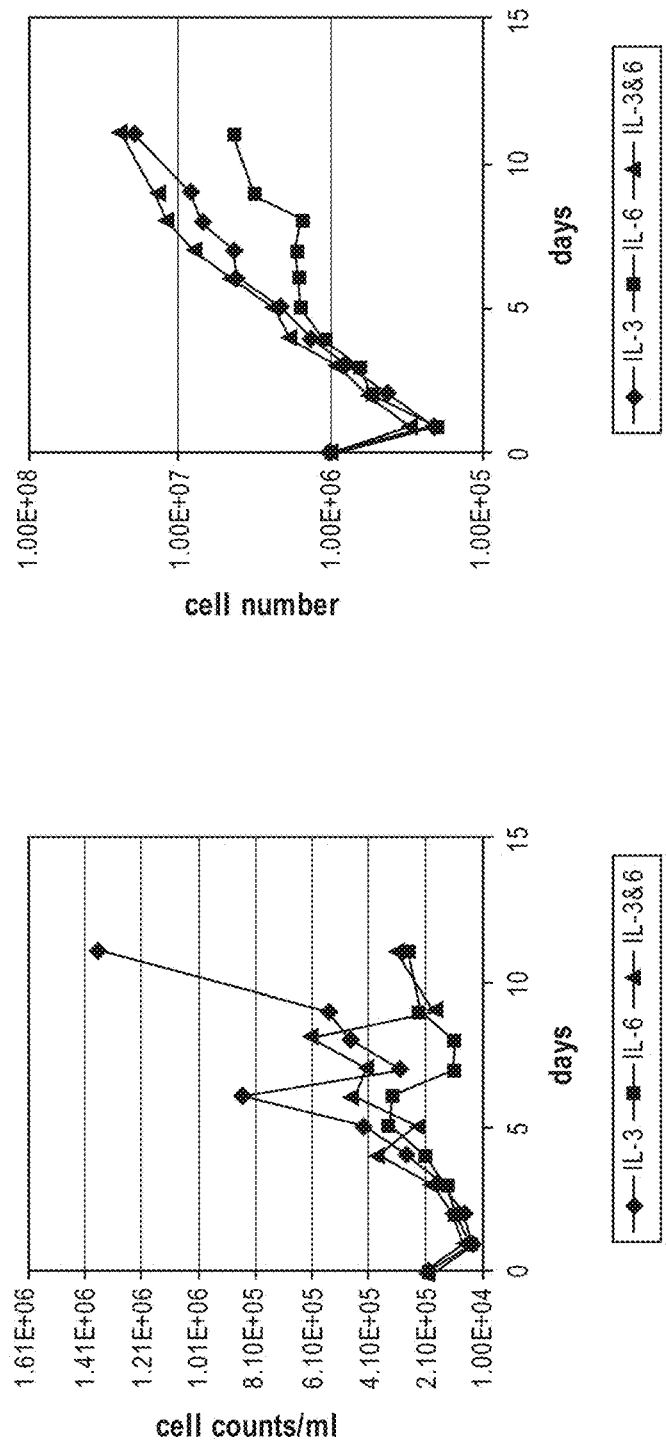

METHODS OF EXPANDING MYELOID CELL POPULATIONS AND USES THEREOF

1. CROSS-REFERENCES TO RELATED APPLICATIONS

The present application is a continuation of U.S. patent application Ser. No. 14/481,715, filed Sep. 9, 2014, which is a divisional of U.S. patent application Ser. No. 13/540,471, filed Jul. 2, 2012, which is a divisional of U.S. patent application Ser. No. 11/259,592, now U.S. Pat. No. 8,252,587, filed Oct. 25, 2005, which claims benefit under 35 U.S.C. § 119(e) to application Ser. No. 60/622,318, entitled "Methods of Expanding Myeloid Cell populations and Uses Thereof", filed Oct. 25, 2004, the disclosure of each is incorporated herein by reference in its entirety.

2. TECHNICAL FIELD

The present disclosure relates to compositions and methods for short-term reconstitution of the hematopoietic system, and uses thereof for treatment of conditions associated with impaired or ablated hematopoiesis.

3. INTRODUCTION

Hematopoietic stem cell transplantation (HSCT) is a standard therapy for various hematological malignancies, and in some cases, is the only viable treatment option, particularly when the disease is refractory to chemotherapy. Bone marrow, peripheral blood, or cord blood serve as typical sources of hematopoietic stem cells (HSCs), but cells from peripheral blood display more rapid engraftment characteristics and may be mobilized by treatment of the donor with cytokines G-CSF, GM-CSF, or with cytoreductive drugs. Cord blood is readily available, shows lower incidences of graft versus host disease but is characterized by delayed engraftment. Prior to transplantation, the recipient is given myeloablative doses of chemotherapy and/or radiation to treat the underlying disease and make the recipient suitable for engraftment of the donor HSCs.

Generally, there are two types of HSCT: autologous and allogeneic. Autologous transplantation involves infusion of a recipient's own cells following myeloablative treatment. Autologous cell transplants minimize the risk of graft versus host disease (GVHD) and result in reduced complications. Since chemotherapy with myeloablative agents is used to eliminate malignant cells in the HSC preparation, autologous transplantation is problematic if the disease is unresponsive to chemotherapy. Allogeneic transplantation involves infusion of donor stem cells, typically using a donor that matches the recipient's MHC. An advantage of allogeneic transplants is the accompanying cell-mediated graft versus host reaction that may develop against malignant cells. However, matched unrelated donor (MUD) transplants are also associated with a stronger graft versus host reaction, and thus result in higher mortality rates.

There are several added complications associated with myeloablative therapy and HSCT, most notably neutropenia and thrombocytopenia. Both conditions arise from impaired hematopoiesis and the inability of the hematopoietic system to adequately replenish the terminally differentiated myeloid cell associated with each disorder. Neutropenia and thromobocytopenia may also develop from other causes of impaired hematopoiesis, such as unintended exposure to lethal doses of ionizing radiation, inherited immunodeficiencies, viral infections affecting the bone marrow, and metabolic disorders (e.g., vitamin deficiencies).

Neutropenia is a condition characterized by abnormally low numbers of white blood cells, particularly neutrophils, which are short lived and represent the most abundant leukocyte in the peripheral blood. Neutrophils and other polymorphonuclear leukocytes migrate to sites of infection through the action of various chemokines to provide a critical immune response against the infectious agents. During the time period required for recovery of the hematopoietic system following transplant, the transplant recipient has low levels of circulating neutrophils and is susceptible to bacterial and fungal infections, particularly to opportunistic infections by commonly occurring microorganisms, such as *Pseudomonas aeruginosa* and *Aspergillus fumigatus*. Prolonged neutropenia, particularly those resulting from delayed engraftment of donor HSCs, increases the probability of infection and is associated with high mortality rates.

One standard therapy for neutropenia is administration of G-CSF. This cytokine promotes granulocyte development and also enhances the immune effector responses of neutrophils. G-CSF accelerates recovery following hematopoietic stem cell transplantation, but it may not be effective for subjects treated with high dose chemotherapy in the absence of HSCT because of the low numbers of responsive hematopoietic stem cells in the patient.

Another therapeutic approach involves infusion of neutrophils (granulocyte transfusions) as a temporary measure to protect against infections. Following treatment of the donor with G-CSF or GM-CSF, cells are collected by leukapheresis of peripheral blood and administered into the recipient to elevate circulating neutrophil levels (see, e.g., Lin, Y-W et al., *J. Clin. Microbiol.* 41(10):4892-4893 (2003)). Subjects treated by this method show increased survival, but the clinical efficacy of this approach appears uncertain, possibly owing to the short life span of differentiated neutrophils following transplant or due to adverse effects of storage on neutrophil activity (McCullough, J. et al., *Transfusion* 23(1):20 (1983)). Moreover, because the efficacy of neutrophil transfusion correlates with the number of cells administered, the limited availability of donor cells, usually from matched sibling or haplomatched parent, and the inability to store the cells may limit the general applicability of this approach.

Thrombocytopenia is a condition associated with another terminally differentiated cell of the myeloid lineage, the megakaryocyte, and is characterized by abnormally low levels of platelets. Platelets are essential to the blood clotting process and are needed to limit leakage of erythrocytes from blood vessels. Below normal levels of platelets result in increased risk of bleeding, and may result in spontaneous bleeding when platelet levels drop below a critical level. Thromobocytopenia may arise from impaired platelet production and/or increased rate of removal. Occurrence of thrombocytopenia in the HSCT setting results from the impaired development of megakaryocytes, and is heightened by delayed engraftment of HSCs, complications from infections, and incidences of GVHD. As with neutropenia, managing thrombocytopenia is critical after any myeloablative treatment to minimize life-threatening complications.

Platelet transfusion is a routine therapy to treat thromobocytopenia, and is effective in reducing serious bleeding problems associated with low platelet levels. Use of platelets from MHC-matched donors minimizes any adverse immune response against the donor platelets. The association between infections and thrombocytopenia, however, suggests that neutropenia may complicate the thrombocytopenic condition, requiring more frequent transfusions in such patients. In addition, use of G-CSF therapy for treating neutropenia is contraindicated for thrombocytopenia because of accelerated platelet destruction correlated with G-CSF administration.

Although the infusion of immune protective cells for neutropenia and transfusions of platelets for thrombocytopenia remain viable approaches for treating these conditions, it is desirable to increase the duration of protection, and for neutropenia, to have available a more consistent supply of cells for administration. Moreover, treatments capable of addressing both disorders concurrently, rather than separately, will improve management of these complications of impaired hematopoiesis.

4. SUMMARY

The present disclosure describes compositions and methods useful in the treatment of complications arising from impaired hematopoiesis. The inability to generate terminally differentiated cells of the myeloid lineage in subjects with insufficient hematopoiesis leads to a number of life threatening conditions, most notably neutropenia and thrombocytopenia. By transiently replacing the cell population associated with these conditions, complications arising from depletion of the differentiated myeloid cells are ameliorated or prevented until such time as the patient's endogenous or reconstituted hematopoietic system can regenerate.

Accordingly, in one aspect, the present invention provides methods for preparing therapeutic compositions of myeloid progenitor cells for reconstituting hematopoiesis in a mammalian host, comprising: a) culturing ex vivo a starting cell population including hematopoietic stem cells in a suitable culture medium to expand said cell population and increase the number of myeloid progenitor cells within said cell population; and b) resuspending said myeloid progenitor cells in a pharmaceutically acceptable medium suitable for administration to a mammalian host. Advantageously, as demonstrated herein, the initial population of cells may be derived from an allogeneic donor or, still more preferably, from a plurality of allogeneic donors, resulting in ex vivo expanded allogeneic myeloid progenitor cells obtained from one or a plurality of donors. The donors may be related or unrelated to each other, and in the transplant setting, related or unrelated to the recipient.

Surprisingly, as further demonstrated herein, the present inventors have determined that the expanded myeloid progenitor cells of the present invention can be cryopreserved after expansion and still retain their functionality in reconstituting hematopoiesis in a therapeutic setting, including granulocyte/macrophage progenitors. Although hematopoietic stem cells are known to retain their functionality after cryopreservation, see, e.g., U.S. Pat. No. 5,004,681, the cryopreservation of their more differentiated progeny has not been uniformly successful, thus complicating their practical implementation as a clinical cell-based therapy. The expanded myeloid progenitors provided herein have this advantageous feature, and in a preferred embodiment are cryopreserved prior to resuspension and administration to a patient.

The initial population of cells for expansion may be derived from peripheral blood, mobilized peripheral blood, umbilical cord blood, bone marrow, and/or other organs known to harbor hematopoietic stem cells, such as fetal liver. Cell populations may be mixtures of cells as obtained from a source or cells isolated, particularly as an enriched or substantially pure population, based on a desired cell marker phenotype (e.g., CD34+ and/or CD90+ and/or AC133+ and/or ALDH+ cells). Preferably, the starting cell population is enriched for HSC based on the presence of the cell marker CD34+ or CD90+; and still more preferably, the starting cell population is purified HSC that are both CD34+ and CD90+, particularly for expansion of human myeloid progenitor cells. In a further embodiment, the cells may also have the cell marker phenotype $Lin^{neg/low}$.

In another aspect, the invention provides therapeutic compositions including the expanded myeloid progenitor cells resulting from the inventive methods. In one embodiment, the therapeutic composition comprises or consists essentially of expanded myeloid progenitor cells in a pharmaceutically acceptable carrier. In another embodiment, the therapeutic composition comprises or consists essentially of expanded myeloid progenitor cells cryopreserved in a cryopreservation medium. In a preferred embodiment, the expanded myeloid progenitor cells are allogeneic, and still more preferably, the expanded myeloid progenitor cells are a mixture of allogeneic myeloid progenitor cells. The mixture of allogeneic myeloid progenitor cells may comprise at least a partial mismatch at the MHC, where the MHC mismatch is between the MHC of the various donors or between the donors and the recipient, or a full or complete mismatch at the MHC. Accordingly such mixtures of allogeneic cells may comprise a partial mismatch at the MHC between some cells and a full mismatch between other cells in the population. In a particular embodiment, progenitor cells that undergo temporary engraftment (e.g., progenitor cell populations occurring early in the myeloid lineage) are selected to have a match or a partial mismatch at the MHC while more differentiated progenitor cells have a partial or full mismatch at the MHC.

In a further embodiment, the mixtures of allogeneic myeloid progenitor cells are mixtures of isolated cells. These include isolated CMPs, isolated GMPs, isolated MEPs, or combinations thereof.

Cells for the mixtures may be obtained from unexpanded myeloid progenitor cells, or from ex vivo expanded cell cultures described herein. For mixtures of allogeneic expanded cells, the allogeneic cells may be mixed prior to expansion or subsequent to expansion.

In another aspect, the present disclosure provides methods of generating myeloid progenitor cells through their ex vivo expansion in culture. In the methods, cells capable of producing myeloid progenitor cells such as, e.g., hematopoeitic stem cells (HSC), are contacted with a culture medium comprising a cytokine and growth factor mixture that supports expansion of myeloid progenitor cells, and the cells are then cultured under suitable conditions that facilitate their expansion. Suitable cytokines for ex vivo expansion purposes are selected from IL-1 (i.e., IL-1β), IL-3, IL-6, IL-11, G-CSF, GM-CSF, and analogs thereof. Suitable growth factors for ex vivo expansion purposes are selected from c-kit ligand (SCF or SF), FLT-3 ligand (FL), thrombopoietin (TPO), erythropoietin (EPO), and analogs thereof. As used herein, analogs include variants of the cytokines and growth factors having the characteristic biological activity of the naturally occurring forms.

In a preferred embodiment, the medium is a chemically-defined medium lacking undefined (qualitatively or quantitatively) components, including cell-based expansion materials such as stromal cells or other feeder cells. Significantly, the inclusion of such materials can be problematic from a manufacturing and regulatory perspective, and the selection and development of a chemically-defined alternative that appropriately expands the desired cell types represents another yet significant contribution of the present invention.

In one embodiment, the cytokine and growth factor mixture in its base composition has stem cell factor (SCF), FLT-3 ligand (FL), and thromobopoietin (TPO). In preferred embodiments, the cytokine and growth factor mixture has an additional cytokine selected from IL-3, IL-6, IL-11, G-CSF, GM-CSF, and combinations thereof, and particularly from IL-3, IL-6, IL-11, and combinations thereof. Thus, in one embodiment, the cytokine and growth factor mixture has the composition SCF, FL, TPO, and IL-3 while in another embodiment, the mixture has the composition SCF, FL, TPO, and IL-6. One combination of the additional cytokine is IL-6 and IL-11 such that the cytokine and growth factor mixture has the composition SCF, FL, TPO, IL-6 and IL-11.

Forms of the cytokines and growth factors are their naturally occurring products, recombinant products, variants or analogs, or modified forms having similar biological activity to the naturally occurring forms. The cytokines are chosen to be active on the cells used for expansion, and thus their source will generally reflect the origin of the initial cells used for expansion, although this correspondence between the form of the cytokine and the origin of the cells need not be rigorous since cross-reactivity between forms is known for various cytokines and growth factors, and is readily testable. Thus, in one embodiment the cytokines used are recombinant human (rhu) rhuIL-1, rhuIL-1β), rhuIL-3, rhuIL-6, rhuIL-11, rhuG-CSF, rhuGM-CSF, or analogs thereof. Similarly, the growth factors used are recombinant human rhuSCF, rhuFL, rhuTPO, rhuEPO, or analogs thereof.

The starting cell population is cultured under conditions that support expansion of myeloid progenitor cells to defined levels. Expanded myeloid progenitor cells obtained in accordance with the present invention generally comprise common myeloid progenitor cells (CMP), granulocyte/macrophage progenitor cells (GMP), and megakaryocyte/erythroid progenitor cells (MEP). Thus, in one aspect, the ex vivo expanded cultures comprise expanded CMPs in which the CMP cell population is expanded at least about 5 fold, about 10 fold, about 20 fold, or at least about 30 fold. In the final cell culture preparation (e.g., at the time of cell harvest), the expanded culture comprises a CMP population which is at least about 0.5%, at least about 1%, at least about 2%, at least about 5%, and at least about 10% of the total cells in the culture.

In another aspect, the ex vivo expanded cultures comprise expanded GMPs in which the GMP cell population is expanded at least about 10 fold, about 20 fold, about 40 fold, and preferably at least about 80 fold. In the final cell culture preparation, the expanded cultures comprise a GMP population which is at least about 10%, at least about 20%, at least about 30%, and preferably at least about 50% of the total cells in culture. The MEP cell population in the cultures is expanded at least about 0.1 fold, about 2 fold, about 5 fold, and at least about 10 fold. In the final cell culture preparation, the expanded cultures comprise a MEP cell population which is at least about 0.5%, about 1%, about 2%, and at least about 5% of the total cells in the culture.

Collectively, the combined total of the myeloid progenitor cells in the final cell culture preparation is at least about 25%, at least about 40%, more preferably greater than about 50%, still more preferably at least about 60% or 70%, most preferably at least about 80% or 90%, and ideally at least about 95% of the total cells in the expanded culture.

Cells prepared by ex vivo expansion may be resuspended in a pharmaceutically acceptable carrier and used directly or alternatively may be subjected to processing by various cell purification techniques available to the skilled artisan, such as FACS sorting, magnetic affinity separation, and immunoaffinity columns. Cell populations isolated from the expanded cultures include, among others, isolated myeloid progenitor cells, isolated CMP, isolated GMP and isolated MEP. Preferably the isolated cell population is a substantially pure population of cells.

The cells described herein have various applications in therapeutic and non-therapeutic settings. In therapeutic applications, the cells are used to treat subjects with impaired or ablated hematopoiesis. Cells are administered into a subject, such as by intravenous infusion, in a sufficient amount to provide a therapeutic benefit, either prophylatically to lessen the occurrence of adverse conditions associated with impaired hematopoiesis or to treat a subject already suffering from complications associated with impaired hematopoiesis. In a further aspect, the cells are used to treat subjects in the HSCT setting, either concurrently with or subsequent to the HSCT.

Neutropenia and thrombocytopenia are associated with impaired hematopoiesis, particularly where the subject has undergone myeloablative therapy, although the conditions can occur in other contexts. The cells described herein are applicable for the treatment of these conditions, either as a prophylactic measure to reduce the occurrence of the conditions or when the subject is afflicted with the conditions. As with the other therapeutic applications, cells in therapeutic form include expanded or unexpanded myeloid progenitor cells. Since neutropenia and thrombocytopenia are associated with insufficiency of specific myeloid cell types, the cell populations chosen can be tailored to the specific condition being treated. In one embodiment, the cells are CMPs, which is useful for either condition since CMPs ultimately develop into neutrophils and megakaryocytes. In situations of neutropenia, the cells can be GMPs since GMPs ultimately develop into neutrophils. In situations for thrombocytopenia, the cells can be MEPs since MEPs ultimately develop into megarkaryocytes. As will be apparent to the skilled artisan, combinations of cell populations find application in treating these conditions, as well as the conditions described above. Combinations of isolated GMP and MEP are useful for treating neutropenia and thrombocytopenia concurrently. Addition of CMPs to the combination should provide more prolonged protection arising from the temporary engraftment of CMPs and subsequent production of neutrophils and megakaryocytes. Other combinations include CMP and GMP if neutropenia is the main focus of treatment, while the combination may be CMP and MEP if thrombocytopenia is the main focus of treatment.

Cells are administered by methods well known in the art. In one embodiment, the administration is by intravenous infusion. The administration of cells can be through a single administration or successive administrations. When successive administrations are involved, different cells numbers and/or different cells populations may be used for each administration. Thus in one embodiment, a first administration is of a cell population or a combination of cell populations that provide an immediate therapeutic benefit as well as more prolonged effect (CMP+GMP+neutrophils) while the second administration includes cells providing prolonged effect (e.g., CMP) to extend the therapeutic effect of the first administration. These and other strategies will be apparent to the skilled artisan.

In further embodiments, the myeloid progenitor cells described herein are used in combination with other therapeutic compounds that are effective in treating the conditions associated with impaired hematopoiesis, and/or complications of neutropenia and thrombocytopenia. In one embodiment, the adjunctive treatments are antibacterial, antifungal, or antiviral compounds for preventing opportunistic infections or infections already in progress in the subject.

In another embodiment, the adjunctive treatments are therapeutic compounds that augment the differentiation of myeloid progenitor cells in the myeloid pathway. These adjunctive treatments have the effect of inducing differentiation and mobilization of myeloid progenitor cells that are endogenous, or administered to the subject as part of the therapy. In one embodiment, particularly for treating or preventing neutropenia, G-CSF or GM-CSF is administered concurrently with or subsequent to cell administration. Another adjunctive treatment involves administration of EPO or TPO, in particular as adjunctive treatments for thrombocytopenia since EPO induces differentation of MEK into proerythroblasts and mature erythroid cells while TPO appears to induce growth and differentiation of hematopoietic stem cells and early myeloid progenitor cells into megakaryocytes and mature platelets.

In a final aspect, the disclosure provides kits containing the cytokines and growth factor mixture, initial cells for expansion, media and other necessary components for carrying out the ex vivo expansion methods. Kits directed to use of the cell populations, expanded or unexpanded, for therapeutic applications, such as for treatments for neutropenia and thrombocytopenia, are provided. The kits may further include, by way of example and not limitation, buffers, labels, reagents, and instructions for methods of using the kits.

5. BRIEF DESCRIPTION OF THE DRAWINGS

FIG. 1A-1C is a schematic of an experimental design showing (FIG. 1A) Cell populations sorted and analyzed. (FIG. 1B) Derivation of myeloid progenitors from HSC in culture, culture derived MP cells can be used fresh or cryopreserved. (FIG. 1C) The use of myeloid progenitors to protect neutropenic mice from a fungal challenge.

FIG. 4A-4B shows a comparison of fresh (FIG. 4A) and cryopreserved (FIG. 4B) myeloid progenitors.

FIG. 17A-17B show the effect of IL-3 and IL-6, alone and in combination on human myeloid progenitors cells.

6. DETAILED DESCRIPTION OF PREFERRED EMBODIMENTS

Figures 2A, 2B:
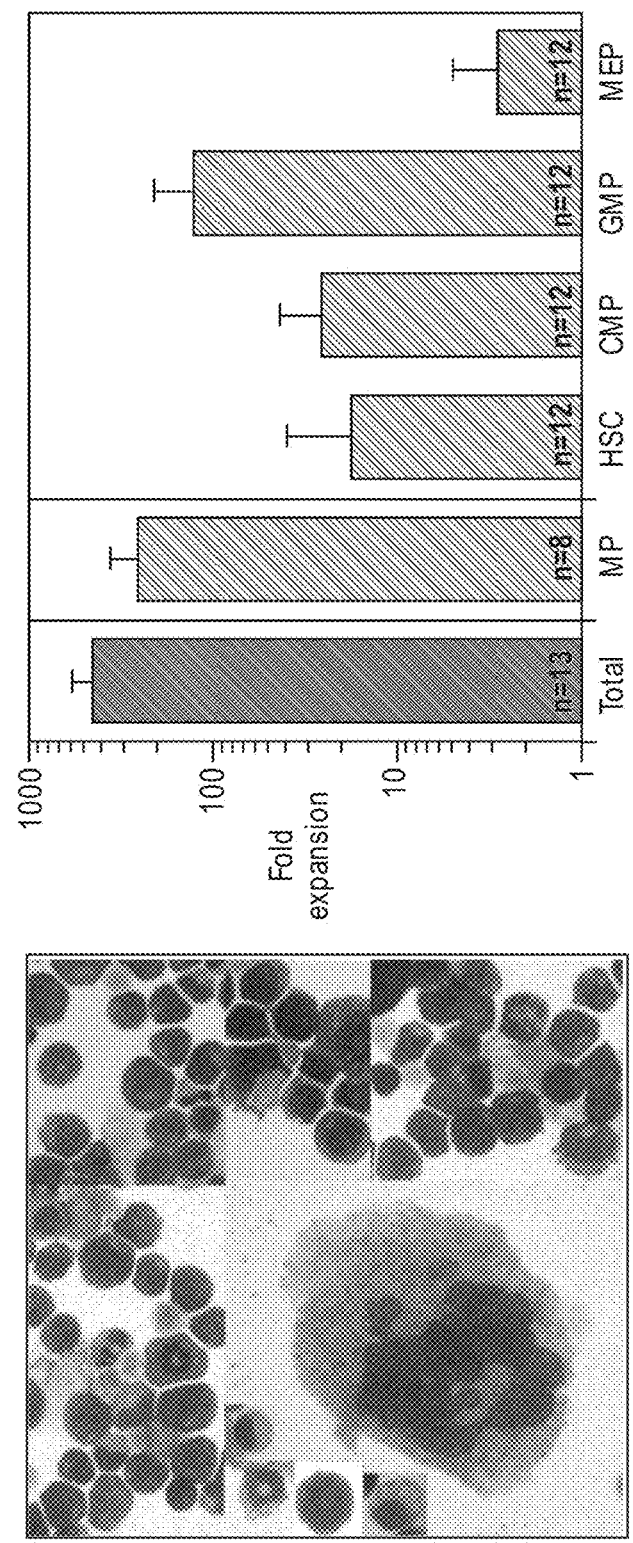
FIG. 2A-2B shows derivation of myeloid progenitors from HSC in culture.

The present disclosure describes methods of generating cells useful for the treatment of conditions associated with a deficient or impaired hematopoietic system, such as the neutropenia and thrombocytopenia that develops following myeloablative therapy and hematopoietic stem cell transplantation, chemotherapy for malignant diseases, or as a consequence of unintentional exposure to high doses of ionizing radiation. The expanded cells described herein comprise committed myeloid progenitor cells (MP) generated by contacting an initial population of stem cells and progenitor cells with a defined cytokine and growth factor mixture permissive for the development of the committed myeloid progenitor cells. Under the defined culture conditions, myeloid progenitor cells expand preferentially to defined levels. The expanded cells are used as a whole, or subjected to purification to provide isolated cells having a defined cell marker phenotype and a characteristic differentiation potential. Isolated cell populations include common myeloid progenitors (CMP), granulocyte/macrophage progenitors (GMP), megakaryocyte/erythroid progenitors (MEP), and combinations thereof. Infusion of these committed myeloid progenitor cells into an immunodeficient patient results in short term engraftment and/or production of terminally differentiated cells of the myeloid lineage. This provides a temporary but prolonged replenishment of terminally differentiated cells, particularly neutrophils and megakaryocytes, thereby complementing the period of deficient hematopoiesis.

In the HSCT field, expansion techniques have been mainly directed towards increasing the population of HSCs for the purposes of transplantation and permanent restoration of hematopoiesis (Devine, S. M. et al., *Bone Marrow Transplantation* 31:241-252 (2003); Henschler, R. et al., *Blood* 84(9):2898-2903 (1994); Bhatia, M. et al., *J. Exp. Med.* 186:619-624 (1997)). Combinations of cytokines and growth factors employed generally attempt to cause preferential expansion of HSCs while limiting their differentiation into committed cells of the myeloid and lymphoid lineages. The number of HSCs expanded in the context of HSCT is especially relevant since the engraftment characteristics of infused cells and survival of the transplant recipient is correlated with increasing numbers of infused HSCs, particularly where there is a mismatch at the MHC of the donor and recipient (Ketterer N. et al., *Blood* 91:3148-3155 (1998)). Culture conditions that induce differentiation of the stem cells are undesirable because of the lower numbers of HSCs produced. Because HSCs have self-renewing capacity, long term cultures are used in some instances to select for self-replenishing HSC populations (Piacibillo, W. et al., *Blood* 93(11):3736-3749 (1999)).

In contrast, committed myeloid progenitor cells have limited or no self renewing capacity, and thus culture conditions suitable for HSC expansion are not optimal for expansion of these cells. On the other hand, the presence of cytokines that promote rapid development of the cultured cells into terminally differentiated cells (e.g., neutrophils and megakaryocytes) is undesirable because these expanded cell populations may not provide the prolonged protection afforded by infusion of less differentiated progenitor cells that are found in initial phases of the myeloid differentiation pathway (Reichle, A. et al., *Bone Marrow Transplantation* 32:299-305 (2003); Zimmerman, T. M. et al., *Bone Marrow Transplantation* 26:505-510 (2000); Reiffers, J. et al., *Lancet* 354:1092-1093 (1999)). Thus, the expansion approach described herein limits the generation of HSCs while increasing the numbers MPs, particularly CMP and GMP cells. HSCs present in the expanded cell population are principally short-term repopulating hematopoietic stem cells (ST-HSC), and are generally less than 10% of the expanded cells, more preferably less than 5%, and typically in the range of 2-5% of the expanded cell population. The expansion methods are applicable to cells used in the autologous or allogeneic transplant setting.

Advantageously, to further increase the number of cells available for expansion and/or therapy and to make widespread clinical application commercially feasible, the cell populations described herein preferably include mixtures of allogeneic myeloid progenitor cells. Typically, allogeneic cells are not used for HSCTs because of possible GVHD and host-versus-graft reactions, both of which can delay engraftment of HSCs in the transplant recipient. Instead, a single donor having a complete or partial match at the MHC is generally used as the source of HSCs. Unlike the HSCT context, however, the use of allogeneic committed myeloid progenitor cells that do not match with the MHC of the host is not adverse to their therapeutic effectiveness since permanent engraftment is neither the purpose nor the effect produced by infusion of these differentiated cells. Loss of HSCs, and long-term repopulating HSCs in particular, also is not detrimental to the therapeutic effect since temporary protection against neutropenia and/or thrombocytopenia is provided by the committed myeloid progenitor cells. The mixtures of allogeneic myeloid cells may be prepared from expanded or unexpanded cells.

6.1 Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor.

"Autologous" refers to deriving from or originating in the same subject or patient. An "autologous transplant" refers to the harvesting and reinfusion or transplant of a subject's own cells or organs. Exclusive or supplemental use of autologous cells can eliminate or reduce many adverse effects of administration of the cells back to the host, particular graft versus host reaction.

"Chemically-defined" as used herein refers to culture media of known chemical composition, both quantitatively and qualitatively, with no deliberately added uncharacterized supplements, even though such a medium may contain trace contaminants in its components. A chemically-defined medium necessarily lacks animal serum, feeder cells such as stromal cells, and cell-based extracellular matrices derived from, e.g., fibroblasts and the like.

"Committed myeloid progenitor cell" or "myeloid progenitor cell" refers to a multipotent or unipotent progenitor cell capable of ultimately developing into any of the terminally differentiated cells of the myeloid lineage, but which do not typically differentiate into cells of the lymphoid lineage. Hence, "myeloid progenitor cell" refers to any progenitor cell in the myeloid lineage. Committed progenitor cells of the myeloid lineage include oligopotent CMP, GMP, and MEP as defined herein, but also encompass unipotent erythroid progenitor, megakaryocyte progenitor, granulocyte progenitor, and macrophage progenitor cells. Different cell populations of myeloid progenitor cells are distinguishable from other cells by their differentiation potential, and the presence of a characteristic set of cell markers.

"Committed lymphoid progenitor cell" or "lymphoid progenitor cell" refers to an oligopotent or unipotent progenitor cell capable of ultimately developing into any of the terminally differentiated cells of the lymphoid lineage, such as T cell, B cell, NK cell, or lymphoid dendritic cells, but which do not typically differentiate into cells of the myeloid lineage. As with cells of the myeloid lineage, different cell populations of lymphoid progenitors are distinguishable from other cells by their differentiation potential, and the presence of a characteristic set of cell markers.

"Common lymphoid progenitor cell" or "CLP" refers to an oligopotent cell characterized by its capacity to give rise to B-cell progenitors (BCP), T-cell progenitors (TCP), NK cells, and dendritic cells. These progenitor cells have little or no self-renewing capacity, but are capable of giving rise to T lymphocytes, B lymphocytes, NK cells, and lymphoid dendritic cells.

"Common myeloid progenitor cell" or "CMP" refers to a cell characterized by its capacity to give rise to granulocyte/monocyte (GMP) progenitor cells and megakaryocyte/erythroid (MEP) progenitor cells. These progenitor cells have limited or no self-renewing capacity, but are capable of giving rise to myeloid dendritic, myeloid erythroid, erythroid, megakaryocytes, granulocyte/macrophage, granulocyte, and macrophage cells.

"Congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus.

"Cytokine" refers to compounds or compositions that in the natural state are made by cells and affect physiological states of the cells that produce the cytokine autocrine factors) or other cells. Cytokine also encompasses any compounds or compositions made by recombinant or synthetic processes, where the products of those processes have identical or similar structure and biological activity as the naturally occurring forms. Lymphokines refer to natural, synthetic, or recombinant forms of cytokines naturally produced by lymphocytes, including, but not limited to, IL-1, IL-3, IL-4, IL-6, IL-11, and the like.

"Expansion" in the context of cells refers to increase in the number of a characteristic cell type, or cell types, from an initial population of cells, which may or may not be identical. The initial cells used for expansion need not be the same as the cells generated from expansion. For instance, the expanded cells may be produced by growth and differentiation of the initial population of cells. Excluded from the term expansion are limiting dilution assays used to characterize the differentiation potential of cells.

"Functional" in the context of cells refers to cells capable of performing or cells that retain the regular functions or activities associated with the specified cell type, as identified by a defined functional assay or assays. For instance, a "functional GMP cell" is a progenitor cell capable of ultimately differentiating into granulocytes and macrophages, where the terminally differentiated cells function as normal granulocytes and macrophages.

"Graft-versus-host response" or "GVH" or "GVHD" refers to a cellular response that occurs when lymphocytes of a different MHC class are introduced into a host, resulting in the reaction of the donor lymphocytes against the host.

"Granulocyte/macrophage progenitor cell" or "GMP" refers to a cell derived from common myeloid progenitor cells, and characterized by its capacity to give rise to granulocyte and macrophage cells, but which does not typically give rise to erythroid cells or megakaryocytes of the myeloid lineage.

"Growth factor" refers to a compound or composition that in the natural state affects cell proliferation, cell survival, and/or differentiation. A growth factor, while having the indicated effect on the cell, may also affect other physiological process, such as secretion, adhesion, response to external stimuli, and the like. Although many growth factors are made by cells, growth factors as used herein also encompass any compound or composition made by recombinant or synthetic processes, where the product of those processes have identical or similar structure and biological activity as the naturally occurring growth factor. Examples of growth factors include epidermal growth factor (EGF), fibroblast growth factor (FGF), erythropoietin (EPO), thromobopoietin (TPO), stem cell factor (SCF), and flt-3 ligand (FL), and analogs thereof.

"Isolated" refers to a product, compound, or composition which is separated from at least one other product, compound, or composition with which it is associated in its naturally occurring state, whether in nature or as made synthetically.

"Hematopoietic stem cell" or "HSC" refers to a clonogenic, self-renewing pluripotent cell capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers. "Enriched" when used in the context of HSC refers to a cell population selected based on the presence of a single cell marker, generally CD34+, while "purified" in the context of HSC refers to a cell population resulting from a selection on the basis of two or more markers, preferably CD34+CD90+.

"Marker phenotyping" refers to identification of markers or antigens on cells for determining their phenotype (e.g., differentiation state and/or cell type). This may be done by immunophenotyping, which uses antibodies that recognize antigens present on a cell. The antibodies may be monoclonal or polyclonal, but are generally chosen to have minimal crossreactivity with other cell markers. It is to be understood that certain cell differentiation or cell surface markers are unique to the animal species from which the cells are derived, while other cell markers will be common between species. These markers defining equivalent cell types between species are given the same marker identification even though there are species differences in structure (e.g., amino acid sequence). Cell markers include cell surfaces molecules, also referred to in certain situations as cell differentiation (CD) markers, and gene expression markers. The gene expression markers are those sets of expressed genes indicative of the cell type or differentiation state. In part, the gene expression profile will reflect the cell surface markers, although they may include non-cell surface molecules.

"Megakaryocyte/erythroid progenitor cell" or "MEP" refers to a cell derived from common myeloid progenitor cells, and characterized by its capacity to give rise to erythroid cells and megakaryocytes, but which does not typically give rise to granulocytes, macrophages, or myeloid dendritic cells.

"Mismatched allogeneic" refers to deriving from, originating in, or being members of the same species having non-identical major histocompatability complex (MHC) antigens (i.e., proteins) as typically determined by standard assays used in the art, such as serological or molecular analysis of a defined number of MHC antigens. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

"Myeloablative" or "myeloablation" refers to impairment or destruction of the hematopoietic system, typically by exposure to a cytotoxic agent or radiation. Myeloablation encompasses complete myeloablation brought on by high doses of cytotoxic agent or total body irradiation that destroys the hematopoietic system. It also includes a less than complete myeloablated state caused by non-myeloablative conditioning. Thus, non-myeloablative conditioning is treatment that does not completely destroy the subject's hematopoietic system.

"Neutropenia" refers to a lower than normal number of neutrophils and other polymorphonuclear leukocytes in the peripheral blood. Typically, a neutropenic condition is diagnosed based on the absolute neutrophil count (ANC), which is determined by multiplying the percentage of bands and neutrophils on a differential by the total white blood cell count. Clinically, an abnormal ANC is fewer than about 1500 cells per ml of peripheral blood. The severity of neutropenia is categorized as mild for an ANC of 1000-1500 cells per ml, moderate for an ANC of 500-1000 cells per ml, and severe for an ANC of fewer than 500 cells per ml.

"Self renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype.

"Short term repopulating hematopoietic stem cells" or "ST-HSC" refers to hematopoietic stem cells that have limited, short term self-renewing capacity, and are characterized by their capacity to differentiate into cells of the myeloid and lymphoid lineage. ST-HSC are distinguished from long-term repopulating (LT) HSCs by their limited length of self-renewal activity in culture assays (e.g., approximately 8 weeks; see, Christensen, J. L. and Weissman, I. L., Proc. Natl. Acad. Sci. USA (2001)).

"Sorting" as it pertains to cells refers to separation of cells based on physical characteristics (such as, e.g., elutriation or other size-based techniques) or presence of markers (such as sorting using side scatter (SSC) and forward scatter (FSC), or fluorescence activation cell sorting (FACS) using labeled antibodies), or analysis of cells based on presence of cell markers, e.g., FACS without sorting, and including as well immunoabsorption techniques such as, e.g., magnetic cell separation systems.

"Substantially pure cell population" refers to a population of cells having a specified cell marker characteristic and differentiation potential that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

"Subject" or "patient" are used interchangeably and refer to, except where indicated, mammals such as humans and non-human primates, as well as rabbits, rats, mice, goats, pigs, and other mammalian species.

"Syngeneic" refers to deriving from, originating in, or being members of the same species that are genetically identical, particularly with respect to antigens or immunological reactions. These include identical twins having matching MHC types. Thus, a "syngeneic transplant" refers to transfer of cells or organs from a donor to a recipient who is genetically identical to the donor.

"Thrombocytopenia" refers to a lower than normal platelet count, generally less than about $100 \times 10^9$/L, which gives rise to increased clotting time and increased risk of spontaneous bleeding, particularly at platelet levels of about $10-50 \times 10^9$/L or lower. The condition occurs when platelets are lost from circulation at a faster rate than their replenishment by megakaryocytes. Thrombocytopenia may result from either failure of platelet synthesis and/or increased rate of platelet destruction.

"Xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

6.2 Cell Types and Sources of Cells for Expansion

The cell types relevant to the present disclosure are those of the hematopoietic system, particularly hematopoieitc stem cells and cells of the myeloid lineage. Descriptions of cells herein will use those known to the skilled artisan, with the understanding that these descriptions reflect the current state of knowledge in the art and the invention is not limited thereby to only those phenotypic markers described herein.

The hematopoietic stem cells (HSC) are pluripotent stem cells capable of self-renewal and are characterized by their ability to give rise under permissive conditions to all cell types of the hematopoietic system. HSC self-renewal refers to the ability of an HSC cell to divide and produce at least one daughter cell with the same self renewal and differentiation potential of a HSC; that is, cell division gives rise to additional HSCs. Self-renewal provides a continual source of undifferentiated stem cells for replenishment of the hematopoietic system. The marker phenotypes useful for identifying HSCs will be those commonly known in the art. For human HSCs, the cell marker phenotypes preferably include $CD34^+$ $CD38^-$ $CD90(Thy1)^+$ $Lin^-$. For mouse HSCs, an exemplary cell marker phenotype is $Sca-1^+$ $CD90^+$ (see, e.g., Spangrude, G. J. et al., Science 1:661-673 (1988)) or $c-kit^+$ $Thy^{lo}$ $Lin^-$ $Sca-1^+$ (see, Uchida, N. et al., J. Clin. Invest. 101(5):961-966 (1998)). Alternative HSC markers such as aldehyde dehydrogenase (see Storms et al., Proc. Nat'l Acad. Sci. 96:9118-23 (1999) and AC133 (see Yin et al., Blood 90:5002-12 (1997) may also find advantageous use.

HSCs give rise to committed lymphoid or myeloid progenitor cells. As used herein committed myeloid progenitor cells refer to cell populations capable of differentiating into any of the terminally differentiated cells of the myeloid lineage. Encompassed within the myeloid progenitor cells are the common myeloid progenitor cells (CMP), a cell population characterized by limited or non-self-renewal capacity but which is capable of cell division to form granulocyte/macrophage progenitor cells (GMP) and megakaryocyte/erythroid progenitor cells (MEP). Non-self renewing cells refers to cells that undergo cell division to produce daughter cells, neither of which have the differentiation potential of the parent cell type, but instead generates differentiated daughter cells. The marker phenotypes useful for identifying CMPs include those commonly known in the art. For CMP cells of murine origin, the cell population is characterized by the marker phenotype $c-Kit^{high}$ (CD117) $CD16^{low}$ $CD34^{low}$ $Sca-1^{neg}$ $Lin^{neg}$ and further characterized by the marker phenotypes $Fc\gamma R^{lo}$ $IL-7R\alpha^{neg}$ (CD127). The murine CMP cell population is also characterized by the absence of expression of markers that include B220, CD4, CD8, CD3, Ter119, Gr-1 and Mac-1. For CMP cells of human origin, the cell population is characterized by $CD34^+$ $CD38^+$ and further characterized by the marker phenotypes $CD123^+$ ($IL-3R\alpha$) $CD45RA^{neg}$. The human CMP cell population is also characterized by the absence of cell markers CD3, CD4, CD7, CD8, CD10, CD11b, CD14, CD19, CD20, CD56, and CD234a. Descriptions of marker phenotypes for various myeloid progenitor cells are described in, for example, U.S. Pat. Nos. 6,465,247 and 6,761,883; Akashi, Nature 404: 193-197 (2000); all publications incorporated herein by reference in their entirety.

Another committed progenitor cell of the myeloid lineage is the granulocyte/macrophage progenitor cell (GMP). The cells of this progenitor cell population are characterized by their capacity to give rise to granulocytes (e.g., basophils, eisinophils, and neutrophils) and macrophages. Similar to other committed progenitor cells, GMPs lack self-renewal capacity. Murine GMPs are characterized by the marker phenotype $c-Kit^{hi}$ (CD117) $Sca-1^{neg}Fc\gamma R^{hi}$ (CD16) $IL-7R\gamma^{neg}$ $CD34^{pos}$. Murine GMPs also lack expression of markers B220, CD4, CD8, CD3, Gr-1, Mac-1, and CD90. Human GMPs are characterized by the marker phenotype CD34+ CD38+ CD123+CD45RA+. Human GMP cell populations are also characterized by the absence of markers CD3, CD4, CD7, CD8, CD10, CD11 b, CD14, CD19, CD20, CD56, and CD235a.

Where relevant to the discussion, the megakaryocyte/erythroid progenitor cells (MEP), which are derived from the CMPs, are characterized by their capability of differentiating into committed megakaryocyte progenitor and erythroid progenitor cells. Mature megakaryocytes are polyploid cells that are precursors for formation of platelets, a developmental process regulated by thrombopoietin. Erythroid cells are formed from the committed erythroid progenitor cells through a process regulated by erythropoietin, and ultimately differentiate into mature red blood cells. Murine MEPs are characterized by cell marker phenotype c-Kit$^{hi}$ and IL-7Rα$^{neg}$ and further characterized by marker phenotypes FcγR$^{lo}$ and CD34$^{low}$. Murine MEP cell populations are also characterized by the absence of markers B220, CD4, CD8, CD3, Gr-1, and CD90. Another exemplary marker phenotype for mouse MEPs is c-kit$^{high}$ Sca-1$^{neg}$ Lin$^{neg/low}$ CD16$^{low}$ CD34$^{low}$. Human MEPs are characterized by marker phenotypes CD34+ CD38+ CD123$^{neg}$ CD45RA$^{neg}$. Human MEP cell populations are also characterized by the absence of markers CD3, CD4, CD7, CD8, CD10, CD11 b, CD14, CD19, CD20, CD56, and CD235a.

Further restricted progenitor cells in the myeloid lineage are the granulocyte progenitor, macrophage progenitor, megakaryocyte progenitor, and erythroid progenitor. Granulocyte progenitor cells are characterized by their capability to differentiate into terminally differentiated granulocytes, including eosinophils, basophils, neutrophils. The GPs typically do not differentiate into other cells of the myeloid lineage. With regards to the megakaryocyte progenitor cell (MKP), these cells are characterized by their capability to differentiate into terminally differentiated megarkaryocytes but generally not other cells of the myeloid lineage (see, e.g., WO 2004/024875).

For the lymphoid lineage, a "committed lymphoid progenitor cell" refers to a cell capable of differentiating into any of the terminally differentiated cells of the lymphoid lineage. Encompassed within the lymphoid progenitor cells are the common lymphoid progenitor cells (CLP), a cell population characterized by limited or non-self-renewal capacity but which is capable of cell division to form T lymphocyte and B lymphocyte progenitor cells, NK cells, and lymphoid dendritic cells. The marker phenotypes useful for identifying CLPs will be those commonly known in the art. For CLP cells of mouse, the cell population is characterized by the presence of markers as described in Kondo, M. et al., Cell 91:661-672 (1997), while for human CLPs, a marker phenotype of CD34+ CD38+ CD10+ IL7R+ may be used (Galy, A et al., Immunity, 3:459-473 (1995); Akashi, K. et al., Int. J. Hematol. 69(4):217-226 (1999)); publications incorporated herein by reference.

A summary of preferred murine cell surface markers is provided in Table 1 below, where an approximate indication of staining levels is shown by the cell colors in the tables: an asterisk indicates no staining, a caret indicates low level staining and a dagger indicates intermediate or high staining.

TABLE 1

| HSC | CD117† | CD90.1^ | Lin1* | Sca-1† | * | * |
| CLP | CD117† | CD90.1* | Lin1* | Sca-1† | CD127† | * |

TABLE 1-continued

| MP | CD117† | Sca-1* | Lin2* | * | * | * |
| CMP | CD117† | Sca-1* | Lin2* | CD16/32^ | CD34† | CD9* |
| GMP | CD117† | Sca-1* | Lin2* | CD16/32† | CD34† | CD9* |
| MEP | CD117† | Sca-1* | Lin2* | CD16/32^ | CD34^ | CD9* |
| MKP | CD117† | Sca-1* | Lin2* | CD16/32^ | CD34^ | CD9† |

Lin1: CD3, CD4, CD5, CD8, B220, Gr-1, CD11b, TER119
Lin2: CD3, CD4, CD5, CD8, B220, Gr-1, CD90.1, CD127, TER119

A summary of preferred human cell surface markers is provided in Table 2 below, where an approximate indication of staining levels is shown by the cell colors in the tables: an asterisk indicates no staining, a caret indicates low level staining and a dagger indicates intermediate or high staining.

TABLE 2

| HSC | CD34† | CD90† | Lin1* | * | * |
| CLP | CD34† | CD127† | CD10† | CD38/CD90* | Lin* |
| MP | CD34† | CD90* | Lin2* | * | * |
| CMP | CD34† | CD90* | Lin2* | CD45RA† | CD123^ |
| GMP | CD34† | CD90* | Lin2* | CD45RA† | CD123† |
| MEP | CD34† | CD90* | Lin2* | CD45RA^ | CD123^ |

Lin 1: CD2, CD3, CD7, CD8, CD10, CD11b, CD14, CD19, CD56, CD235a
Lin 2a: CD2, CD3, CD4, CD7, CD8, CD10, CD11b, CD14, CD19, CD20, CD56, CD235a
Lin 2b: CD10, CD11b, CD14, CD19, CD235a

Numerous other suitable cell surface markers are presently known to the skilled artisan, or will be identified and characterized in due course, and such markers will find advantageous use in the methods and compositions described herein. For instance, several additional potential murine markers have recently been identified for the various myeloid progenitor cell populations based on array analysis of mRNA expression. See, e.g., Iwasaki-Arai, et al. J. Exp. Med. 197:1311-1322 (2003); Akashi, et al. Nature 404:193-197 (2000); Miyamoto, et al. Dev. Cell 3:137-147 (2002); Traver, et al. Blood 98:627-635 (2001); Akashi, et al. Blood 101:383-390 (2003); Terskikh, A., et al. Blood 102:102:94-101 (2003). Based on this same type of mRNA expression analysis, additional cell surface markers such as CD110, CD114, CD116, CD117, CD127, and CD135 may also find use for isolating one or more of the identified myeloid progenitor subpopulations in humans, as described in Manz, et al. Proc Natl Acad Sci USA 99:11872-11877 (2002).

For the methods described herein, the cells for expansion will be cells capable of ultimately differentiating into cells of the myeloid lineage, i.e., granulocytes, macrophages, megakaryocytes, erythroid cells, and/or myeloid dendritic cells. These include, among others, HSCs, and committed myeloid progenitor cells CMPs, GMPs, and MEPs. These cells will have the relevant characteristics, particularly differentiation potential and cell marker characteristics described above. In one embodiment, the initial cells for the expansion comprise cells with marker phenotype CD34+. Because the CD34 marker is found in different progenitor cell types, the initial cell population for expansion can be a mixture of progenitor cells expressing CD34. In another embodiment, the cells are cells comprising the cell marker phenotype Sca-1$^{pos}$, a cell marker found in mouse, and other rodents. Selection for Sca-1$^{pos}$ cells will also result in a mixture of cells displaying the cell marker phenotype, although it will primarily select for HSCs because the mouse committed myeloid progenitor cells are Sca-1$^{neg}$. Thus, in other embodiments for expansion of rodent myeloid cells, the cell marker phenotype of Lin$^{neg/low}$ is used, which includes HSCs, CMPs, and GMPs.

In a further aspect, the initial cells for expansion are isolated cells. These include isolated HSCs, which under the presence of the indicated mixture of cytokines and growth factors, develop into CMPs that further expand into other progenitor cells of the myeloid lineage. In another embodiment, the initial cells for expansion are CMPs with the characteristic differentiation potential and cell marker phenotypes as described above. CMPs may have limited self-renewal capacity, and thus can expand to generate additional CMPs for a limited number of cells divisions while also differentiating into GMPs and MEPs.

Cells for expansion can be obtained from a variety of sources, including bone marrow, peripheral blood, cord blood, and other sources known to harbor hematopoietic and myeloid progenitor cells, including liver, particularly fetal liver. Peripheral and cord blood is a rich source of HSCs and progenitor cells. Cells are obtained using methods known and commonly practiced in the art. For example, methods for preparing bone marrow cells are described in Sutherland et al., *Bone Marrow Processing and Purging: A Practical Guide* (Gee, A. P. ed.), CRC Press Inc. (1991)). Umbilical cord blood or placental cord blood is typically obtained by puncture of the umbilical vein, in both term or preterm, before or after placental detachment (see, e.g., Turner, C. W. et al., *Bone Marrow Transplant.* 10:89 (1992); Bertolini, F. et al., *J. Hematother.* 4:29 (1995)). HSCs and myeloid progenitor cells may also be obtained from peripheral blood by leukapheresis, a procedure in which blood drawn from a suitable subject is processed by continuous flow centrifugation (e.g., Cobe BCT Spectra blood cell separators) to remove white blood cells while the other blood components are returned to the donor. Another type of isolation procedure is centrifugation through a medium of varying density, such as Ficoll-Hypaque (Amersham Pharmacia Biotech, Piscataway, N.J.).

The cells are derived from any animal species with a hematopoietic system, as generally described herein. Preferably, suitable animals will be mammals, including, by way of example and not limitation, rodents, rabbits, canines, felines, pigs, horses, cows, primates (e.g., human), and the like. The cells for the expansion may be obtained from a single subject, or a plurality of subjects. A plurality refers to at least two (e.g., more than one) donors. When cells obtained are from a plurality of donors, their relationships may be syngeneic, allogenenic, or xenogeneic, as defined herein. A preferred embodiment of the present disclosure is directed to a mixture of allogeneic myeloid progenitor cells obtained by the expansion methods herein, as further described below. The allogeneic cells may be expanded separately and the cells mixed following expansion, or the cells mixed prior to expansion, as further discussed below.

Where applicable, stem cells and progenitor cells may be mobilized from the bone marrow into the peripheral blood by prior administration of cytokines or drugs to the subject (see, e.g., Lapidot, T. et al., *Exp. Hematol.* 30:973-981 (2002)). Cytokines and chemokines capable of inducing mobilization include, by way of example and not limitation, granulocyte colony stimulating factor (G-CSF), granulocyte macrophage colony stimulating factor (GM-CSF), erythropoietin (Kiessinger, A. et al., *Exp. Hematol.* 23:609-612 (1995)), stem cell factor (SCF), AMD3100 (AnorMed, Vancouver, Canada), interleukin-8 (IL-8), and variants of these factors (e.g., pegfilgastrim, darbopoietin). Combinations of cytokines and/or chemokines, such as G-CSF and SCF or GM-CSF and G-CSF, can act synergistically to promote mobilization and may be used to increase the number of HSC and progenitor cells in the peripheral blood, particularly for subjects who do not show efficient mobilization with a single cytokine or chemokine (Morris, C. et al., *J. Haematol.* 120:413-423 (2003)).

Cytoablative agents can be used at inducing doses (i.e., cytoreductive doses) to also mobilize HSCs and progenitor cells, and are useful either alone or in combination with cytokines. This mode of mobilization is applicable when the subject is to undergo myeloablative treatment, and is carried out prior to the higher dose chemotherapy. Cytoreductive drugs for mobilization, include, among others, cyclophosphamide, ifosfamide, etoposide, cytosine arabinoside, and carboplatin (Montillo, M. et al., *Leukemia* 18:57-62 (2004); Dasgupta, A. et al., *J. Infusional Chemother.* 6:12 (1996); Wright, D. E. et al., *Blood* 97:(8):2278-2285 (2001)).

The cells for expansion may also be subjected to further selection and purification, which can include both positive and negative selection methods, to obtain a substantially pure population of cells. In one aspect, fluorescence activated cell sorting (FACS), also referred to as flow cytometry, is used to sort and analyze the different cell populations. Cells having the cellular markers specific for HSC or a progenitor cell population are tagged with an antibody, or typically a mixture of antibodies, that bind the cellular markers. Each antibody directed to a different marker is conjugated to a detectable molecule, particularly a fluorescent dye that can be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and progenitor cells is described in, among others, U.S. Pat. Nos. 5,137,809, 5,750, 397, 5,840,580; 6,465,249; Manz, M. G. et al., *Proc. Natl. Acad. Sci. USA* 99:11872-11877 (2002); and Akashi, K. et al., *Nature* 404(6774):193-197 (2000)). General guidance on fluorescence activated cell sorting is described in, for example, Shapiro, H. M., *Practical Flow Cytometry*, 4th Ed., Wiley-Liss (2003) and Ormerod, M. G., *Flow Cytometry: A Practical Approach*, 3rd Ed., Oxford University Press (2000).

Another method of isolating the initial cell populations uses a solid or insoluble substrate to which is bound antibodies or ligands that interact with specific cell surface markers. In immunoadsorption techniques, cells are contacted with the substrate (e.g., column of beads, flasks, magnetic particles) containing the antibodies and any unbound cells removed. Immunoadsorption techniques can be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads can be readily isolated by a magnetic separator (see, e.g., Kato, K. and Radbruch, A., *Cytometry* 14(4):384-92 (1993); $CD34^+$ direct isolation kit, Miltenyi Biotec, Bergisch, Gladbach, Germany). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations.

FACS and most batch wise immunoadsorption techniques can be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that can be employed is use of antibody/complement treatment or immunotoxins to remove unwanted cells.

It is to be understood that the purification of cells also includes combinations of the methods described above. A typical combination may comprise an initial procedure that is effective in removing the bulk of unwanted cells and cellular material, for example leukapharesis. A second step may include isolation of cells expressing a marker common to one or more of the progenitor cell populations by immunoadsorption on antibodies bound to a substrate. For example, magnetic beads containing anti-CD34 antibodies are able to bind and capture HSC, CMP, and GMP cells that commonly express the CD34 antigen. An additional step providing higher resolution of different cell types, such as FACS sorting with antibodies to a set of specific cellular markers, can be used to obtain substantially pure populations of the desired cells. Another combination may involve an initial separation using magnetic beads bound with anti-CD34 antibodies followed by an additional round of purification with FACS.

Determining the differentiation potential of cells, and thus the type of stem cells or progenitor cells isolated, is typically conducted by exposing the cells to conditions that permit development into various terminally differentiated cells. These conditions generally comprise a mixture of cytokines and growth factors in a culture medium permissive for development of the myeloid or lymphoid lineage. Colony forming culture assays rely on culturing the cells in vitro via limiting dilution and assessing the types of cells that arise from their continued development. A common assay of this type is based on methylcellulose medium supplemented with cytokines (e.g., MethoCult, Stem Cell Technologies, Vancouver, Canada; Kennedy, M. et al., *Nature* 386:488-493 (1997)). Cytokine and growth factor formulations permissive for differentiation in the hematopoietic pathway are described in Manz et al., *Proc. Natl Acad. Sci. USA* 99(18): 11872-11877 (2002); U.S. Pat. No. 6,465,249; and Akashi, K. et al., *Nature* 404(6774):193-197 (2000)). Cytokines include SCF, FLT-3 ligand, GM-CSF, IL-3, TPO, and EPO. Another in vitro assay is long-term culture initiating cell (LTC-IC) assay, which typically uses stromal cells to support hematopoiesis (see, e.g., Ploemacher, R. E. et al., *Blood*. 74:2755-2763 (1989); and Sutherland, H. J. et al., *Proc. Natl. Acad. Sci. USA* 87:3745 (1995)).

Another type of assay suitable for determining the differentiation potential of isolated cells relies upon in vivo administration of cells into a host animal and assessment of the repopulation of the hematopoietic system. The recipient is immunocompromised or immunodeficient to limit rejection and permit acceptance of allogeneic or xenogeneic cell transplants. A useful animal system of this kind is the NOD/SCID (Pflumio, F. et al., *Blood* 88:3731 (1996); Szilvassym S. J. et al., "Hematopoietic Stem Cell Protocol," in *Methods in Molecular Medicine, Humana Press* (2002); Greiner, D. L. et al., *Stem Cells* 16(3):166-177 (1998); Piacibello, W. et al., *Blood* 93:(11):3736-3749 (1999)) or Rag2 deficient mouse (Shinkai, Y. et al., *Cell* 68:855-867 (1992)). Cells originating from the infused cells are assessed by recovering cells from the bone marrow, spleen, or blood of the host animal and determining presence of cells displaying specific cellular markers, (i.e., marker phenotyping) typically by FACS analysis. Detection of markers specific to the transplanted cells permits distinguishing between endogenous and transplanted cells. For example, antibodies specific to human forms of the cell markers (e.g., HLA antigens) identify human cells when they are transplanted into suitable immunodeficient mouse (see, e.g., Piacibello. W. et al., supra).

The initial populations of cells obtained by the methods above are used directly for expansion or frozen for use at a later date. A variety of mediums and protocols for freezing cells are known in the art. Generally, the freezing medium will comprise DMSO from about 5-10%, 10-90% serum albumin, and 50-90% culture medium. Other additives useful for preserving cells include, by way of example and not limitation, disaccharides such as trehalose (Scheinkonig, C. et al., *Bone Marrow Transplant.* 34(6):531-6 (2004)), or a plasma volume expander, such as hetastarch hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well known and described in the art (see, e.g., Broxmeyer, H. E. et al., *Proc. Natl. Acad. Sci. USA* 100(2): 645-650 (2003)). Cells are preserved at a final temperature of less than about −135° C.

6.3 Ex Vivo Expansion of Myeloid Progenitor Cells

The initial population of cells obtained above is expanded ex vivo in culture by contacting the cells with a medium having a cytokine and growth factor mixture permissive for expansion of myeloid progenitor cells. Cytokines in their natural context are typically proteins made by cells that modulate a cell's physiological state, whether the cell is another cell or the cell producing the cytokine. Cytokines made by lymphocytes are often described as lymphokines (IL), but are cytokines as defined herein. Cytokines typically act via cellular receptors on the cells modulated by the cytokine. Likewise, growth factors in their natural context are also compounds typically made by cells, affecting the proliferation and differentiation of cells, whether the cell is another cell or the cell producing the growth factor. Like cytokines, growth factors generally act on cells via receptors. Reference to a cytokine or growth factor in the present disclosure, however, is not meant to be exclusionary since certain cytokines have effects on proliferation and differentiation of cells similar to growth factors. Hence, the descriptions of specific cytokines and growth factors herein reflect the state of knowledge in the art and are not meant to limit the scope of this disclosure.

For the expansion methods herein, cytokines and growth factors are chosen to expand populations of committed myeloid progenitor cells, such as CMP, GMP, and MEP cells. Since these cells have limited or no self-renewing capacity, the culture conditions are chosen to support division of cells that develop into these myeloid cells while limiting or minimizing growth and expansion of other cell types that are not committed myeloid progenitors.

Accordingly, cytokines for expansion conditions are generally selected from IL-1 (i.e., IL-1β), IL-3, IL-6, IL-11, G-CSF, CM-CSF, and analogs thereof. Forms of the cytokines are naturally occurring products, recombinant products, variants, or modified forms having similar biological activity as the naturally occurring forms such as, e.g., peptide mimetics. The cytokines may also be selected from the group of fusion proteins or engineered cytokines, suitable non-limiting examples include PIXY321 (Curtis, B. M., et al. Proc. Natl. Acad. Sci. U.S.A. 1991 88.5809-5813) a synthetic hybrid protein of GM-CSF and IL-3, Epo-IL-3 (Lu, L., et al. Exp. Hematol. 1995 23. 1130-1134), IL-2-IL-6 (Zhao. C., et al. Stem Cells 1994. 12. 1130-1134).

Source of the cytokines are chosen to be active on the cells used for expansion, and thus will generally reflect the origin of the initial cells used for expansion. For example, if the progenitor cells are of human origin, human forms of the cytokine, either natural or recombinant, are used. Accordingly, in one embodiment, the cytokines are recombinant human rhuIL-1, rhuIL-1β), rhuIL-3, rhuIL-6, rhuIL-11, rhuG-CSF, rhuGM-CSF, and analogs thereof. However, the association between the form of the cytokine and the origin of cells need not be rigorous. For instance, human IL-6 is able to elicit effects in mouse and rat cells, although mouse IL-6 has no effect on human cells. This type of crossactivity will be apparent to the skilled artisan and can be readily tested by known methods. The structure and function of the specified cytokines will refer to the descriptions below, which reflect the state of knowledge in the art.

IL-1 is a group of cytokines that has important roles in the up- and down-regulation of acute inflammation (e.g., activation of endothelial cells and lymphocytes), bone formation and remodeling, insulin secretion, and fever induction. IL-1 family of cytokines shares an overall structural similarity, being composed of β-barrel with a pseudo three fold axis (see, e.g., Priestle, J. P. et al., *Proc Natl Acad Sci USA* 86, 9667-71 (1989)). Pertinent to the methods herein is IL-1β, which is typically secreted by macrophages along with IL-1α. The two agonists are derived by enzymatic cleavage of precursor proteins (pro-IL-1α and pro-IL-1β), and exert their physiological effects by binding to IL-1 receptors. Amino acid sequences and their corresponding nucleic acid sequences for IL-β are known from various sources, including, by way of example and not limitation, murine (Telford, J. L. et al., *Nucleic Acids, Res.* 14(24): 9955-9963 (1986)); rabbit (Young PR and Sylvester D., *Protein Eng.* 2(7):545-51 (1989)); rat (Accession No. NP 113700 [gi:13928692]); porcine (Huether, M. J, et al., *Gene* 129(2):285-289 (1993)); bovine (Leong S. R., *Nucleic Acids Res.* 16:9054-9054(1988)); feline (Daniel, S. L. et al., *Anim. Biotechnol.* 3:117-121 (1992)); equine (Howard, R. D. et al., *Am. J. Vet. Res.* 59:704-711(1998)); human (March, C. J. et al., *Nature* 315:641 (1985); and recombinant human (Meyers, C. et al., *J. Biol. Chem.* 262(23):11176-11181 (1987)). Variants of IL-1β, are described in Boraschi, D. et al., *Frontiers in Bioscience* 1:270-308 (1995)). Various recombinant forms are also available commercially (see, e.g., human IL-1β, Promega, Madison, Wis., USA; murine IL-1β, Stem Cell Technologies, Vancouver, BC, Canada; and rat IL-1β, Chemicon Int., Temacula, Calif., USA). Variants of IL-1β, are described in, among others, Gronenborn, A. M. et al., *Eur. J. Biochem.* 161(1):37-43 (1986); Antoni, Ge et al., *J. Immunol.* 137(10):3201-4 (1986); Palaszynski, E.W., *Biochem. Biophys. Res. Commun.* 147(1):204-11 (1987); and Huang, J. J. et al, *FEBS Lett.* 223(2):294-8 (1987)).

IL-3, also know as multi-CSF, is a multilineage cell cytokine/growth factor secreted by lymphocytes, epithelial cells, and astrocytes, that stimulates the clonal proliferation and differentiation of various types of blood and tissue cells, particularly the differentiation and function of granulocytes and macrophages. It is considered one of the hematopoietic colony stimulating factors (see, e.g., Wagemaker, G. et al., *Biotherapy* 2(4):337-45 (1990)). Amino acid and nucleic acid sequences for IL-3 have been identified from various organisms, including, among others, murine (Fung M.-C. et al., *Nature* 307:233-237(1984)); rat (Cohen, D. R. et al. *Nucleic Acids Res.* 14:3641-3658(1986); sheep (McInnes C. J. et al., *Gene* 139:289-290 (1994)); bovine (Mwangi S. M. et al., *Gene* 162:309-312(1995)); chimpanzee/monkeys (Burger H. et al., *Biochim. Biophys. Acta* 1217:195-198 (1994)); and human (Yang Y.-C. et al., *Cell* 47:3-10 (1986); Otsuka T. et al., *J. Immunol.* 140:2288-2295(1988)). Variants of IL-3 are described in Lopez, A. F. et al., *Proc Natl Acad Sci USA* 89(24):11842-6 (1992); Barry, S. C. et al., *J Bio.l Chem.* 269(11):8488-92 (1994); and Olins, P. O. et al., *J Biol Chem.* 270(40):23754-60 (1995)).

IL-6 is known as B-cell stimulatory factor 2 (BSF-2) and interferon-β2, and is involved in regulating differentiation of B cells into immunoglobulin secreting cells, induction of myeloma/plasmacytoma growth, and nerve cell differentiation. IL-6 binding to IL-6 receptors induces formation of a multisubunit complex containing protein GP130, which is common to the class I cytokine receptor superfamily. IL-6 appears to have a common structure composed of a four helical bundle, where the helical faces interact with the receptor. Amino acid and nucleic acid sequences for IL-6 have been identified for, among others, mouse (Chiu, C. P. et al., *Proc. Natl. Acad. Sci. USA*. 85(19):7099-103 (1988); rat (Northemann, W. et al., *J. Biol. Chem.* 264(27):16072-82 (1989); rabbit (Perkins, H. D. et al., *Cytokine* 12(6):555-65 (2000)); sheep (Ebrahimi, B. et al., *Cytokine*. 7(3):232-236 (1995)); bovine (Droogmans, L. et al., *DNA Seq.* 2(6):411-3 (1992)); equine (Swiderski, C. E. et al., *Vet Immunol Immunopathol.* 77(3-4):213-20 (2000)); and human (Hirano T. et al., *Nature* 324: 73-76 (1986)). Variants of IL-6 are described in Dagan, S. et al., *Protein Expr. Purif.* 3(4):290-4 (1992); Zhang, J. G. et al., *EurJ Biochem.* 207(3):903-13 (1992); and Skelly, S. M. et al., *J Biotechnol.* 34(1):79-86 (1994). Recombinant forms are described in Stoyan, T. et al., *EurJ Biochem.* 216(1):239-45 (1993)); Orita, T. et al., *J Biochem* (Tokyo) 115(2):345-50 (1994)), and are also commercially available.

IL-11 belongs to the IL-6 group of structurally and functionally related cytokines, which, as noted above, uses the transmembrane glycoprotein gp130 to exert its physiological activity. IL-11 is also known as adipogenesis inhibitor factor (AGIF) and oprelvekin. IL-11 acts synergistically with other cytokines and growth factors to stimulate proliferation and differentiation of stem cells into committed progenitor cells and to promote megakaryopoiesis and thrombopoiesis. Opposing effects of IL-11 are seen in vivo and in vitro in that it can enhance engraftment in vivo while in vitro, IL-11 can maintain primitive population of stem cells. Being a class 1 cytokine, IL-11 is also believed to comprise a four helical bundle structure. Amino acid and nucleic acid sequences of IL-11 have been identified for, among others, murine (Morris, J. C. et al., *Exp. Hematol.* 24:1369 (1996); primate (Paul, S. R. et al., *Proc. Natl. Acad. Sci. USA*. 87(19):7512-6 (1990); and human (Ohsumi, J. et al., *FEBS Lett.* 288:13 (1991)). Recombinant forms and variants of IL-11 are described in Miyadai, K. et al., *Biosci.*

*Biotechnol. Biochem.* 60(3):541-2 (1996); Tacken, I. et al., *EurJ Biochem.* 265(2):645-55 (1999)).

G-CSF or granulocyte-colony stimulating factor acts to induce the bone marrow to produce granulocytes, and promote the survival, proliferation, differentiation and function of neutrophil granulocyte progenitor cells and mature neutrophils. It is produced by a number of different cell types, such as endothelial cells and macrophages. Although naturally occurring as a glycoprotein, G-CSF in its non-glycosylated form made through recombinant techniques is fully active. Structurally, G-CSF is related to the class 1 cytokine family, as indicated by the presence of a four-alpha-helix bundle (Hill, C. et al., *Proc Natl Acad Sci USA* 90(11):5167-71 (1993); Lovejoy, B. et al., *J Mol Biol.* 234(3):640-53 (1993). Amino acid and nucleic acid sequences for G-CSF have been identified for, among others, murine (Tsuchiya, M. et al., *Proc Natl Acad Sci USA.* 83(20):7633-7 (1986); rat (Han, S. W. et al., *Gene* 175(1-2):101-4 (1996)); bovine (Heidari, M. and Kehrli, M. E., *Vet. Immunol. Immunopathol.* 73(2):183-91 (2000); sheep (O'Brien, P. M., *DNA Seq.* 4(5):339-42 (1994)); feline (Dunham, S. P. and Onions, D. E., *Cytokine* 14(6):347-51 (2001)); porcine (Kulmburg, P. et al., *Gene* 197(1-2):361-5 (1997)); and human (Nagata, S. et al., *EMBO J.* 5:575-581 (1986)). Recombinant forms and variants of G-CSF are described in Lu, H. S. et al., *Arch Biochem Biophys.* 268(1):81-92 (1989); Kuga, T. et al., *Biochem Biophys Res Commun.* 159(1):103-11 (1989); and Fujii, I. et al., *FEBS Lett.* 410(2-3):131-5 (1997)), and commercially available under the trade name filgrastim; lenograstim; pluripoietin, Neupogen®, granulokine (Amgen, Thousand Oaks, Calif., USA), and granocyte (Rhone-Poulenc).

GM-CSF or granulocyte-macrophage colony stimulating factor, also known as colony stimulating factor 2 stimulates growth and differentiation of hematopoietic precursor cells from various lineages, including granulocytes, macrophages, eosinophils and erythrocytes. It is also part of the class 1 cytokine family, having a four helical bundle structure, and exerts its physiological effect by binding to granulocyte-macrophage colony stimulating factor receptor. Amino acid and nucleic acid sequences known for GM-CSF include, among others, mouse (Gough, N. M. et al., *Nature* 309:763-767(1984); sheep (McInnes, C. J. and Haig, M. C. K., *Gene* 105:275-279(1991); bovine (Maliszewski, C. R., *Mol. Immunol.* 25:843-850(1988)); and human (Cantrell, M. A. et al., *Proc. Natl. Acad. Sci. USA* 82:6250-6254(1985); Lee, F. et al., *Proc Natl Acad Sci USA.* 82(13):4360-4 (1985)). Recombinant forms and variants of GM-CSF are described in DeLamarter, J. F. et al., *EMBO J.* 4(10):2575-81 (1985); Shanafelt A. B. and Kastelein, R. A., *Proc Natl Acad Sci USA.* 86(13):4872-6 (1989), and are available commercially under the tradename molgramostin and sargramostim.

The growth factors for purposes of expansion are selected from stem cell factor (SCF or SF), FLT-3 ligand (FL), thrombopoietin (TPO), erythropoietin (EPO), and analogs thereof. As with the cytokines, growth factor forms are either naturally occurring products or are recombinant forms having similar biological activity as the naturally occurring factors. Accordingly, in one embodiment, the growth factors are recombinant human rhuSCF, rhuFL, rhuTPO, rhuEPO, and analogs thereof. As with the selection of cytokines, growth factors are chosen to be active on the cells used for expansion, and thus will generally reflect the origin of the initial cells, although the association need not be a rigorous one, as noted above. For instance, rat and mouse SCF are active on human cells, but the human protein is much less active on mouse or rat cells. This type of crossactivity will be apparent to the skilled artisan and can be readily tested by known methods. The structure and function of the specified growth factors will refer to the descriptions that follow, which reflect the state of knowledge in the art and are not meant to be limiting.

SCF, also known as c-kit ligand, mast cell growth factor, or Steel factor, acts on multiple levels of the hematopoietic hierarchy to promote cell survival, proliferation, differentiation, adhesion and functional activation in combination with other cytokines. It is of particular importance in the myeloid lineages, particularly on the development of mast cells, but also acts on multipotent stem and progenitor cells, megakaryocytes, and a subset of lymphoid progenitor (Broudy, V. C., *Blood* 90(4):1345-1364 (1997)). SCF exerts its biological effects by binding to its receptor, C-KIT. Naturally occurring SCF is synthesized by bone marrow stromal cells as either a transmembrane form or a soluble form, both of which are biologically active. The overall structure of SCF has an anti-parallel four-helix bundle fold (Zhang, Z. et al., *Proc. Natl. Acad. Sci. USA* 97(14):7732-7 (2000)). Amino acid and nucleic acid sequences known for SCF include, among others, murine (Lyman, S. D. et al., *Cell* 75(6):1157-67 (1993)), rat (Martin, F. H. et al., *Cell* 63(1):203-11 (1990)); feline (Dunham, S. P. and Onions, D. E., *DNA Seq.* 6(4):233-7 (1996); sheep (McInnes, C. J. et al., *Cytokine* 11(4):249-56 (1999)); canine (Shin, I. S. et al., *J Vet Sci.* 2(3):159-66 (2001)); and human (Martin, F. H. et al., supra). Recombinant SCF and variants are described in Jones, M. D. et al., *J. Biol. Chem.* 271:11301 (1996); Lu, H. S. et al., *J. Biol. Chem.* 271:11309 (1996); Langley, K. E. et al., *Arch. Biochem. Biophys.* 295:21 (1992); Lev, S. et al., *Mol Cell Biol.* 13(4):2224-34 (1993); and Langley, K. E. et al., *Arch. Biochem. Biophys.* 311:(1):55-61 (1994).

"FLT-3 ligand", also known as "FL" or "SL cytokine" or "FMS related tyrosine kinase 3 ligand" is a factor that binds to flt-3 receptor (also, "ACD135" or "Aflk2"), a tyrosine kinase receptor molecule generally found on hematopoietic stem cells and primitive progenitor cells, including CD34+ cells. It synergizes with other factors such as CD117 (c-kit) to stimulate hematopoietic stem cell proliferation in vitro and stimulate expansion and mobilization of progenitor cells in vivo (Lyman, S. D. and Williams, D. E., *Curr. Opin. Hematol.* 2(3):177-81 (1995)). Both the full-length FLT-3 ligand (composed of an extracellular domain, a transmembrane domain and an intracellular domain) and a soluble extracellular domain are biologically active (Lyman, S. D. et al., *Cell* 75:1157 (1993); Lyman, S. D. et al., *Blood* 83:2795 (1994)). Preferably, the FLT-3 ligand is the soluble form that contains the amino acid sequence of the full-length extracellular domain. Structure of soluble FLT-3 ligand reveals the presence of two short chain alpha-helical bundles, similar to SCF and G-CSF (Sawides, S. N. et al., *Nat. Struct. Biol.* 7(6):486-91 (2000)). Amino acid and nucleic acid sequences of FL have been identified for, among others, murine (Rosnet, O. et al., *Oncogene.* 6(9):1641-50 (1991); feline (Yang S. and Sim, G. K., *DNA Seq.* 11(1-2):163-6 (2000); canine (Yang, S., supra); and human (Rosnet, O. et al., *Blood.* 82(4):1110-9 (1993)). Recombinant forms and variants of FLT-3 ligand are described in, among others, Sudo, Y. et al., *Blood* 89:3186 (1997) and McClanahan, T. et al., *Blood* 88:3371-3382 (1996)).

Thrombopoietin or "TPO", also known as megakaryocyte growth and differentiation factor (MGDF) or c-Mpl ligand, stimulates the proliferation and differentiation of megakaryocytes, and thus enhances production of platelets in vitro and in vivo (see, e.g., Lok, S. et al., *Stem Cells* 12(6):586-98 (1994)), TPO exerts its effects via binding to a specific cell surface receptor encoded by the proto-oncogene c-mpl. As with many other cytokines and growth factors, TPO is characterized by the presence of an antiparallel four-helix bundle fold (Feese, M. D. et al., *Proc. Natl. Acad. Sci. USA.* 101 (7):1816-21 (2004)). Amino acid and nucleic acid sequences for thrombopoietin are known for, among others, murine (Lok, S., *Nature* 369(6481):565-568 (1994)); rat (Ogami, K. et al., *Gene* 158(2):309-10 (1995)); and human (Foster, D. C. et al., *Proc. Natl. Acad. Sci. USA.* 91(26):13023-13027 (1994); Bartley, T. D. et al., *Cell* 77 (7):1117-1124 (1994)). Recombinant and variant forms of TPO are described in, among others, Souryi, M. et al., *Cell* 63:1137-1147 (1990); Gurney, A. L. et al., *Blood* 85(4): 981-8 (1995); Wada, T. et al., *Biochem Biophys Res Commun.* 213(3):1091-8 (1995); Park, H. et al., *J Biol Chem.* 273(1):256-61 (1998); and Jagerschmidt, A. et al., *Biochem. J.* 333 (Pt 3):729-34 (1998).

Erythropoietin or EPO regulates red blood cell production by stimulating the expansion and maturation of immature erythrocytes and megakaryocyte development (see, e.g., Fisher, J. W., *Proc. Soc. Exp. Biol. Med.* 216(3):358-69 (1997)). It exerts its effect by binding to the EPO receptor. Although the primary site for EPO synthesis is the renal cortex of the kidney, lower levels of EPO are synthesized by the liver and macrophages in the bone marrow. EPO is structurally similar to TPO, as characterized by the presence of a four-helix bundle (Feese, M. D. et al., *Proc. Natl. Acad. Sci. USA.* 101(7):1816-21 (2004)). Amino acid and nucleic acid sequences for EPO are known for, among others, mouse (Shoemaker, C. B. and Mitsock, L. D. et al., *Mol Cell Biol.* 6(3):849-58 (1986)); rat (Nagao, M. et al., *Biochim. Biophys. Acta.* 1171(1):99-102 (1992)); sheep (Fu, P. et al., *Mol Cell Endocrinol.* 93(2):107-16 (1993)); canine (Wen, D. et al., *Blood* 82(5):1507-16 (1993)); bovine (Suliman, H. B. et al., *Gene* 171(2):275-80 (1996)); rabbit ((Vilalta A. et al., *Biochem Biophys Res Commun.* 284(3):823-7 (2001)); swine (Wen, D. et al., supra; David, R. B. et al., *Domest. Anim. Endocrinol.* 20(2):137-47 (2001); monkey (Lin, F. K. et al., *Gene.* 44(2-3):201-9 (1986;)); and human (Lin, F. K. et al., *Proc. Natl. Acad. Sci. USA* 82 (22): 7580-7584 (1985); Gasson, J. C. et al., *Nature* 315(6022):768-71 (1985)). Recombinant forms and variants of EPO are described in Barbone, F. P. et al., *Nephrol Dial Transplant.* 14 Suppl 2:80-4 (1999); Boissel, J. P. et al., *J. Biol. Chem.* 268(21): 15983-93 (1993). EPO is commercially available under the trade names Epogen® (Amgen, Thousand Oaks, Calif., USA), Epogin® (Chugai Pharmaceuticals, JAPAN), Eprex® (Janssen-Cilag, Saunderton, UK), Recormon® (Roche, Basel, Switzerland), and Procrit® (Ortho Biotech., Bridgewater, N.J., USA).

Variants as used herein include substitutions, deletions, insertions of any amino acid in the cytokine or growth factor sequence, where the variant retains the biological activity associated with each cytokine or growth factor. Substitutions of one or more amino acid residues may be made while preserving biological activity, and typically involves substutution of one amino acid with a homologous amino acid, also referred to herein as "conservative substitution." In some instances a non-conservative substitutions may also be made. Homologous amino acids may be classified based on the size of the side chain and degree of polarization, including, small non-polar (e.g., cysteine, proline, alanine, threonine); small polar (e.g., serine, glycine, aspartate, asparagine); intermediate polarity (e.g., tyrosine, histidine, tryptophan); large non-polar (e.g., phenylalanine, methionine, leucine, isoleucine, valine). Homologous amino acid may also be grouped as follows: uncharged polar R groups (e.g., glycine, serine, threonine, cysteine, tyrosine, asparagine, glutamine); acidic amino acids (e.g., aspartic acid, glutamic acid); and basic amino acids (lysine, arginine, and histidine). Examples of conservative variants include the substitution of one hydrophobic residue such as isoleucine, valine, leucine, or methionine for another; the substitution of one polar residue for another polar residue, such as substitution of one arginine for lysine, glutamic acid for aspartic acid, or glutamine for asparagines; and the substitution of one hydroxylated amino acid serine or threonine for another.

Deletions range from about 1 to about 20 residues, although in some cases, deletions may be much larger, particularly when the cytokine or growth factor has physically separable structural and/or functional domains. For instance, a variant of FL is the cleaved extracellular domain, which, as discussed above, retains biological activity when separated from the sequences containing the transmembrane and cytoplamic domains. In addition, amino acids may be added to the amino or carboxy terminus, or in the amino acid sequences joining structural domains, such as a peptide region joining alpha helixes or beta sheets present in the cytokine or growth factor. Variants for each of the cytokines and growth factors will be apparent to the skilled artisan, exemplary references of which are given above.

Cytokine and growth factor combinations are chosen to expand the committed myeloid progenitor cells while limiting expansion of HSCs and restricting the production of terminally differentiated cells of the myeloid lineage. In one embodiment, the mixture of cytokines and growth factors has the basic composition SCF, FL, and TPO. This cytokine and growth factor mixture permits limited expansion HSCs and is permissive for differentiation of HSCs and other progenitor cells into MPs, including, among others, CMP, GMP, and MEPs.

In a further aspect, the basic composition is supplemented with an additional cytokine, including IL-3, IL-6, or IL-11, or combinations thereof. Thus, in one embodiment, the mixture of cytokines and growth factors has the composition SCF, FL, TPO, and IL-3, a cytokine mixture that appears to efficiently expand human myeloid progenitor cells. In another embodiment, the mixture of cytokines and growth factors has the composition SCF, FL, TPO, and IL-6, a cytokine mixture that appears to efficiently expand murine myeloid progenitor cells. Yet in another embodiment, the mixture of cytokine and growth factor has the composition SCF, FL, TPO, IL-6, and IL-11.

In instances where more mature cells of the myeloid lineage are desired to enhance immediate protection against neutropenia and/or thrombocytopenia, the cytokines G-CSF or GM-CSF is added to the foregoing cytokine mixtures. This may be done after an initial period of growth in media lacking G-CSF or GM-CSF to permit expansion of more primitive myeloid progenitor cells prior to promoting differentiation into the progenitor cells that are further along in the myeloid lineage.

It is to be understood that different cytokine and growth factor mixtures above may be used to favor expansion of specified progenitor cells. Preferential expansion of certain cell populations is desirable if the cells are to be used to treat a single condition or a combination of conditions (e.g., neutropenia and thromobocytopenia), and the duration of therapeutic effect desired. For instance, presence of CMPs will provide prolonged amelioration of both neutropenia and thrombocytopenia since CMPs are able to differentiate into granulocytes, macrophages, megakaryocytes, and erythroid cells. On the other hand, a cell population having a significant proportion of GMPs, as compared to CMPs and MEPs, will provide amelioration of neutropenia but have less therapeutic impact on thrombocytopenia since GMPs differentiate into granulocytes and macrophages but not megakaryocytes. Conversely, a cell population having a significant proportion of MEPs, as compared to CMPs and GMPs, will provide amelioration of thrombocytopenia but have less therapeutic impact on neutropenia since MEPs differentiate into erythroid cells and megakaryocytes but not granulocytes and macrophages.

The amount of cytokines and growth factors in the expansion medium is the amount sufficient to support expansion of myeloid progenitor cells to the specified levels in the cell culture. As representative embodiments, SCF is used at an amount sufficient to support expansion, generally in the amount of at least about 1 to about 1000 ng/ml, and preferably at about 50 to about 100 ng/ml. FL is used at an amount sufficient to support expansion, generally in the amount of at least about 1 to about 1000 ng/ml, and preferably at about 30 to about 100 ng/ml. TPO is used at an amount sufficient to support expansion, generally in the amount of at least about 0.5 to about 500 ng/ml, and preferably at about 5 to about 50 ng/ml. IL-1 is used at an amount sufficient to support expansion, generally in the amount of at least about 1 to about 100 ng/ml, and preferably at about 10 to about 50 ng/ml. IL-3 is used at an amount sufficient to support expansion, generally in the amount of at least about 1 to about 100 ng/ml, and preferably at about 10 to about 50 ng/ml. IL-11 is used at an amount sufficient to support expansion, generally in the amount of at least about 1 to about 100 ng/ml, and preferably at about 10 to about 50 ng/ml. G-CSF is used at an amount sufficient to support expansion, generally in the amount of at least about 1 to about 1000 ng/ml, and preferably at about 10 to about 100 ng/ml. GM-CSF is used at an amount sufficient to support expansion, generally in the amount of at least about 1 to about 100 ng/ml, and preferably at about 10 to about 100 ng/ml. When used, EPO is used at an amount sufficient to support expansion, generally in the amount of at least about 1 to about 30 U/ml, and preferably at about 3 to about 10 U/ml. As a general guide, the mixture of cytokines and growth factors will emphasize growth of myeloid progenitor cells while limiting the expansion of hematopoietic stem cells.

Expansion of myeloid progenitor cells is carried out in a basal medium, which is supplemented with the mixture of cytokines and growth factors described above, sufficient to support expansion of myeloid progenitor cells. The basal medium will comprise amino acids, carbon sources (e.g., pyruvate, glucose, etc.), vitamins, serum proteins (e.g., albumin), inorganic salts, divalent cations, antibiotics, buffers, and other preferably defined components that support expansion of myeloid progenitor cells. Suitable basal mediums include, by way of example and not limitation, RPMI medium, Iscove's medium, minimum essential medium, Dulbeccos Modified Eagles Medium, and others known in the art (see, e.g., U.S. Pat. No. 6,733,746). Commercially available basal mediums include, by way of example and not limitation, Stemline™ (Sigma Aldrich), StemSpan™ (StemCell Technologies, Vancouver, Canada), Stempro™ (Life Technologies, Gibco BRL, Gaithersburg, Md., USA) HPGM™ ((Cambrex, Walkersville, Md., USA), QBSF™ (Quality Biological, Gaithersburg, Md., USA), X-VIVO (Cambrex Corp., Walkersville, Md., USA) and Mesencult™ (StemCell Technologies, Vancouver, Canada). The formulations of these and other mediums will be apparent to the skilled artisan.

The initial population of cells are contacted with the mixture of cytokines and growth factors in the basal medium, and cultured to expand the population of myeloid progenitor cells. Expansion is done for from about 2 days to about 14 days, preferably from about 4 days to 10 days, more preferably about 4 days to 8 days and/or until the indicated fold expansion and the characteristic cell populations are obtained.

In one embodiment, the final cell culture preparation is characterized by a CMP cell population that is expanded at least about 0.5 fold, about 1 fold, about 5 fold, about 10 fold, about 20 fold, or preferably at least about 30 fold. In the final culture, the myeloid cell population will comprise CMPs which are at least about 0.5%, at least about 1%, at least about 2%, at least about 5%, and at least about 10% of the total cells in the culture.

In another embodiment, the final cell culture preparation is characterized by a GMP cell population that is expanded at least about 10 fold, about 20 fold, about 40 fold, and preferably at least about 80 fold. In the final culture, the myeloid cell population will comprise GMPs which are at least about 10%, at least about 20%, at least about 30%, and preferably at least about 50% of total cells in the culture. Thus, in preferred embodiments, the cell populations are expanded to preferentially enrich for GMP cells.

In yet a further embodiment, the final cell culture preparations are characterized by a MEP cell population that is expanded at least about 0.1 fold, about 1 fold, about 2 fold, about 5 fold, and preferably about 10 fold. In the final cultures, the myeloid cell population will comprise MEPs which are least about 0.5%, about 1%, about 2%, and preferably at least about 5% of total cells in the culture.

Generally, in the final culture, the expansion of cells with HSC characteristics will be limited to less than about 25 fold, preferably less that about 15 fold, and more preferably less than about 10 fold, and most preferably less than about 5 fold. Generally, the number of HSC cells will be less than the total number of myeloid progenitor cells (i.e., CMP, GMP, and MEP) in culture.

Although less preferred for practical reasons, in some instances, more undefined culture mediums including feeder cells may be used to approximate the microenvironment of the bone marrow where hematopoiesis occurs. Bone marrow stromal cells, endothelial cells, and mesenchymal cells can produce factors that support development and maintenance of hematopoietic cells in culture, and may be used for the expansion of myeloid progenitor cells. The feeder cell cultures may also be supplemented with the mixture of cytokines and growth factors described above to promote cell expansion and development of specified myeloid progenitor cells. Feeder cell based cultures are described in U.S. Pat. No. 5,879,940; Dexter, T. M. et al., *J. Cell Physiol.* 91:335-344 (1976); Okubo, T. et. al., *Cell Structure and Function* 25:133-139 (2000); Shapiro, F. et al., *J Hematother* 5(6):655-62 (1996)); Coutinho, L. H. et al., "Clonal and long term bone marrow cultures using human bone marrow," in *Haemotology: A Practical Approach*, Testa, N. G. and Molineux, G. eds., Oxford University, Oxford, U K (1992); all publications are incorporated by reference). Typically, mononuclear cells from bone marrow are cultured in suitable medium (e.g., Iscove's Modified Dulbecco's Medium) until a stromal cell layer forms. The cultures are then irradiated and seeded with initial population of cells used for expansion.

Another method based on feeder cell cultures is described in Feugier, P. et al., *J Hematother Stem Cell Res* 11(1):127-38 (2002)). This technique uses immortalized bone marrow endothelial cells modified to express cytokines and growth factors sufficient to support growth of HSCs and/or progenitor cells. Recombinant expression vectors encoding the specified cytokines and growth factors are introduced into the immortalized cell line, and the cells cultured to generate the layer of factor producing endothelial cells. The cells are then irradiated and the culture seeded with cells used for the expansion. Generally, the HSC and progenitor cells are weakly adherent or non-adherent under these culture conditions, which permits washing of the expanded cells away from the endothelial cells. For the purposes herein, the cytokine and growth factor genes introduced into the immortalized cells will reflect the combinations sufficient to support expansion of the committed myeloid progenitor cells. Accordingly, in one embodiment, the cytokine genes are selected from those encoding IL-1 (i.e., IL-1β), IL-3, IL-6, IL-11, G-CSF, or CM-CSF. Similarly, the growth factor genes are selected from those encoding SCF, FL, TPO, and EPO.

In accordance with the above, in one embodiment, expression vectors comprising genes encoding SCF, FL, and TPO are introduced into the feeder cells. In a further embodiment, expression vector comprising genes coding for an additional cytokine, including IL-3, IL-6, or IL-11, or combinations thereof, are used with the growth factor combination. Thus, in one embodiment, the genes introduced into the feeder cells encode SCF, FL, TPO, and IL-3. In a further embodiment, the genes introduced into the cells encode SCF, FL, TPO, and IL-6. In yet a further embodiment, the genes encode SCF, FL, TPO, IL-6, and IL-11. The gene sequences are chosen to express cytokine and growth factor forms that are active on the cells used for expansion, and thus will generally reflect the origin of the initial cells used for expansion. For example, if the progenitor cells are of human origin, nucleic acid sequences encoding human forms of the cytokine are used. When the cells for expansion are of murine origin, nucleic acid sequences encoding murine or other rodent forms of the cytokine are used. Nucleic acid sequences that may be used include those encoding recombinant forms or variants as known in the art. Various other gene combinations sufficient to support expansion of myeloid progenitor cells will be apparent to the skilled artisan.

Cells expanded by the methods above are used without further purification, or are isolated into different cell populations by various techniques known in the art, such as immunoaffinity chromatography, immunoadsorption, FACS sorting, or other procedures as described above. Preferably, FACS sorting or immunoadsorption is used. For example, a FACS gating strategy has an initial selection for live cells based on characteristic forward scatter (cell size) and side scatter (cell density) parameters, and a second selection for expression of cell markers for myeloid progenitor cells or non-myeloid cells (e.g., Sca-1$^{neg}$ C-kit$^{hi}$).

The isolated cell populations may comprise isolated committed myeloid progenitor cells, isolated CMPs, isolated GMPs, isolated MEPs, as defined herein. In some situations, an isolated non-myeloid cell population is prepared by removal of committed myeloid cells from the expanded culture. Isolated cells are generally substantially pure populations of cells, and will typically have at least about 50%, preferably at least about 75-80%, more preferably at least about 85-90%, and most preferably at least about 95% of the indicated cells with the characteristic cell marker phenotype and differentiation potential.

6.4 Allogeneic Mixtures of Myeloid Progenitor Cells

As discussed above, to provide sufficient numbers of cells for treatment purposes, and to enable the production of a commercially-feasable clinical product, the cell populations are preferably a mixture of allogeneic myeloid progenitor cells obtained from a plurality of allogeneic donors. Although there exists the possibility of an immune response against therapeutic cells mismatched with the recipient's MHC, the present therapy is meant to provide temporary protection as opposed to more permanent protection afforded by reconstitution of hematopoiesis by HSCs.

Significantly, as described herein, the possibility of GVHD is greatly minimized by using isolated committed myeloid progenitor cells that are depleted of mature lymphoid cells. In one embodiment, this is accomplished by removal of such cells from the expanded cell population prior to administration. In an alternative and preferred embodiment, this is accomplished by starting with a substantially pure population of CD34+ CD90+ HSCs.

Mixtures of allogeneic cells include, allogeneic mixtures of myeloid progenitor cells, mixtures of isolated CMPs, mixtures of isolated GMPs, mixtures of isolated MEPs, or combinations thereof. Cells in the mixture may be completely matched allogeneic, partially mismatched allogeneic, and/or fully mismatched allogeneic cells with respect to the MHC of the transplant recipient, and may be from related donors, usually siblings with the same parental alleles, or unrelated donors. Determining the degree of MHC mismatch will employ standard tests known and used in the art.

For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests are made of at least 4, and preferably at least 6 MHC antigens within the two or three HLA groups, respectively.

In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis lymphocytotoxicity testing). The reaction is examined and graded according to the amount of cells lysed in the reaction (Mickelson, E. and Petersdorf, E. W., *Hematopoietic Cell Transplantation*, Thomas, E. D. et al. eds., pg 28-37, Blackwell Scientific, Malden, Mass. (1999). Other cell-based assays include flow cytometry using labeled antibodies or enzyme linked immuno assays (ELISA).

Molecular methods for determining MHC type generally employ synthetic probes and/or primers to detect specific gene sequences that encode the HLA protein. Synthetic oligonucleotides may be used as hybridization probes to detect restriction fragment length polymorphisms associated with particular HLA types (Vaughn, R. W., *Methods in*

*Molecular Biology: MHC Protocols* 210:45-60 (2002)). Alternatively, primers may be used for amplifying the HLA sequences (e.g., by polymerase chain reaction or ligation chain reaction), the products of which can be further examined by direct DNA sequencing, restriction fragment polymorphism analysis (RFLP), or hydridization with a series of sequence specific oligonucleotide primers (SSOP) (Petersdorf, E. W. et al., *Blood* 92(10):3515-20 (1998); Morishima, Y. et al., *Blood* 99(11):4200-6 (2002); and Middleton, D. and Williams, F., *Methods in Molecular Biology: MHC Protocols* 210:67-112 (2002)).

While description of "matched allogeneic" or "mismatched allogeneic" is given for human MHC, it is to be understood that similar analysis may be conducted for MHCs for various animal species. These include, by way of example and not limitation, mouse, rat (Gill, T. J. et al., *Transplant Proc.* 27(2):1495-500 (1995)), cow (Lewin, H. A, et al., *Immunol Rev.* 167:145-58 (1999), canine (Wagner, J. L. et al., *J. Hered.* 90(1):35-8 (1999)), feline (O'Brien, S. J. and Yuhki, N., *Immunol Rev.* 167:133-44 (1999)), swine (Chardon, P. et al., Genet Sel Evol. 32(2):109-28 (2000)), horses (Kydd, J. et al., *Vet Immunol Immunopathol.* 42(1): 3-60 (1994), and primates (Heise, E. R. et al., *Genetica* 73(1-2):53-68 (1987)).

Allogeneic mixtures of myeloid progenitor cells may have varying degrees of match in the MHC. Thus, in one embodiment, progenitor cells that undergo temporary engraftment and differentiation may be isolated from a donor having a higher degree of MHC match with the recipient than cells intended to provide a more immediate therapeutic benefit. For instance, CMPs may be from a donor having a complete or partial match with the MHC of the recipient, while GMPs and MEPs may be from mismatched donors. Other combinations will be apparent to those skilled in the art.

Allogeneic mixtures of cells may be made in various ways. In one embodiment, cells are obtained from different donors and mixed prior to their expansion in culture. In another embodiment, myeloid progenitor cells from different donors are expanded separately and then mixed after expansion to generate the mixtures of allogeneic progenitor cells. In another aspect, the mixtures of allogeneic cells are prepared from unexpanded cells by obtaining myeloid progenitor cells from different donors and mixing the cells prior to their infusion into the recipient. Whether expanded or non-expanded cells are used, it is shown in the embodiments herein that allogeneic myeloid progenitor cells are effective in protecting mammalian subjects with compromised hematopoiesis from potentially lethal neutropenic and/or thrombocytopenic conditions.

6.5 Cryopreserved Myeloid Progenitor Cells

Surprisingly, as demonstrated for the first time herein, the expanded population of cells described herein can be cryopreserved and stored for future use and still retain their functionality. As described above, a variety of mediums and protocols for freezing cells are known in the art. Generally the cells are concentrated, suspended in a medium supplemented with a cryoprotectant and/or stabilizer, frozen and stored at a temperature of 0° C. or less. In some embodiements the the cells are stored at −70° C. or less e.g., −80° C., or in liquid nitrogen or in the vapor phase of liquid nitrogen. The cells can be stored in any cryoprotectant known in the art. For example, the cryoprotectant can be dimethyl sulfoxide (DMSO) or glycerol. In some embodiments, the freezing medium comprises DMSO from about 5-10%, 10-90% serum albumin, and 50-90% culture medium. In some embodiments, the cryopreservation medium will comprise DMSO about 7.5%, about 42.5% serum albumin, and about 50% culture medium. The cells can be stored in any stabilizer known in the art. For example, the stabilizer may be methyl cellulose or serum.

Prior to freezing, the cells may be portioned into several separate containers to create a cell bank. The cells may be stored, for example, in a glass or plastic vial or tube or a bag. When the cells are needed for future use, a portion of the cryopreserved cells (from one or more containers) may be selected from the cell bank, thawed and used.

6.6 Treatment

Cells prepared by the methods described herein are used for treatment of various disorders related to deficiencies in hematopoiesis caused by disease or myeloablative treatments. As used herein, "treatment" refers to therapeutic or prophylactic treatment, or a suppressive measure for the disease, disorder or undesirable condition. Treatment encompasses administration of the subject cells in an appropriate form prior to the onset of disease symptoms and/or after clinical manifestations, or other manifestations of the disease or condition to reduce disease severity, halt disease progression, or eliminate the disease. Prevention of the disease includes prolonging or delaying the onset of symptoms of the disorder or disease, preferably in a subject with increased susceptibility to the disorder.

Conditions suitable for treatment with the cells described herein include neutropenia, a condition characterized by decrease in the amount of circulating neutrophils, and thrombocytopenia, a condition characterized by less than normal levels of platelets in the peripheral blood. Both conditions may be a result of acquired or inherited disorder.

Defective hematopoietic stem cell development known to create low neutrophil numbers include, among others, reticular dysgenesis, Fanconis's anemia, Chediak-Higashi syndrome, and cyclic neutropenia. For thrombocytopenia, low platelet levels are manifested in, among others, Wiskott-Aldrich Syndrome, thrombocytopenia with absent radii (TAR), and systemic lupus erythematosus. Acquired forms of neutropenia and thrombocytopenia occur under similar circumstances, such as with hematological malignancies, vitamin deficiency, exposure to ionizing radiation, viral infections (e.g., mononucleosis, CMV, HIV, etc.), and following treatment with various cytotoxic drugs.

For the present purposes, the cells may be used prophylactically to reduce the occurrence of neutropenia and thrombocytopenia, and their associated complications, particularly to lessen infection by opportunistic pathogens in patients that have been treated with myeloablative agents or have undergone HSCT. In the transplant setting, myeloid cells can be used concurrently or subsequent to stem cell transplantation until the recipients own HSCs or transplanted HSCs begin to restore hematopoiesis and raise neutrophil and platelet levels sufficiently. Infusion of myeloid progenitor cells increases the number of neutrophils and megakaryocytes in the treated subject, thereby providing temporary but needed protection during the neutropenic or thrombocytopenic period. Use of myeloid progenitor cell populations, as opposed to more differentiated neutrophils and platelets, provides for longer lasting protection because of the temporary engraftment of myeloid progenitors and their differentiation in vivo.

Further, cells comprising a mixture of CMPs, GMPs, and MEPs have the capacity to generate a broader therapeutic effect than protection afforded by infusion of any one single cell population. This arises from the rapid effect on neutrophil and/or platelet levels from the more differentiated progenitors in the cell population while the more primitive committed myeloid progenitors engraft and develop over time to supply the needed neutrophils and megakaryocytes after the more differentiated cells have become depleted. Infusion with a cell population comprising a mixture of progenitor cells may be appropriate for subjects already suffering from neutropenia or thrombocytopenia, while infusion of isolated cell populations may be suitable for prophylaxis in patients where neutrophil or platelet levels have not yet fallen below a critical level. It is to be noted that while treatments may provide a detectable increase in peripheral cell count or ANC, this increase is not a reliable indicator of successful, transient engraftment or efficacy. Thus other measures, such as reduced infection rate and/or increased survival may be used for determining effectiveness of the treatment.

The amount of the cells needed for achieving a therapeutic effect will be determined empirically in accordance with conventional procedures for the particular purpose. Generally, for administering the cells for therapeutic purposes, the cells are given at a pharmacologically effective dose. By "pharmacologically effective amount" or "pharmacologically effective dose" is an amount sufficient to produce the desired physiological effect or amount capable of achieving the desired result, particularly for treating the disorder or disease condition, including reducing or eliminating one or more symptoms or manifestations of the disorder or disease. As an illustration, administration of cells to a patient suffering from a neutropenia provides a therapeutic benefit not only when the underlying condition is eradicated or ameliorated, but also when the patient reports a decrease in the severity or duration of the symptoms associated with the disease. Therapeutic benefit also includes halting or slowing the progression of the underlying disease or disorder, regardless of whether improvement is realized. Pharmacologically effective dose, as defined above, will also apply to therapeutic compounds used in combination with the cells, as further described below.

Cells for infusion include the expanded cell populations without additional purification, or isolated cell populations having defined cell marker phenotype and characteristic differentiation potential as described herein. Expanded cells may be derived from a single subject, where the cells are autologous or allogeneic to the recipient. Accordingly, in one embodiment, the therapeutic cells comprise isolated committed myeloid progenitors. In other embodiments, the cells comprise isolated CMPs, isolated GMPs, isolated MEPs, or combinations thereof. In other embodiments, the cells used for the infusion comprise non-myeloid cells prepared as described herein.

It is to be understood that cells isolated directly from a donor subject without expansion in culture may be used for the same therapeutic purposes as the expanded cells. Preferably, the isolated cells are a substantially pure population of cells. These unexpanded cells may be autologous, where the cells to be infused are obtained from the recipient, such as before treatment with cytoablative agents. In another embodiment, the unexpanded cells are allogeneic to the recipient, where the cells have a complete match, or partial or full mismatch with the MHC of the recipient. As described above, the isolated unexpanded cells are preferably obtained from different donors to provide a mixture of allogeneic myeloid cells.

Transplantation of cells into an appropriate host is accomplished by methods generally used in the art. The preferred method of administration is intravenous infusion. The number of cells transfused will take into consideration factors such as sex, age, weight, the types of disease or disorder, stage of the disorder, the percentage of the desired cells in the cell population (e.g., purity of cell population), and the cell number needed to produce a therapeutic benefit. Generally, the numbers of expanded cells infused may be from about $1 \times 10^4$ to about $1 \times 10^5$ cells/kg, from about $1 \times 10^5$ to about $10 \times 10^6$ cells/kg, preferably about $1 \times 10^6$ cells to about $5 \times 10^6$ cells/kg of body weight, or more as necessary. In some embodiments, the cells are in a pharmaceutically acceptable carrier at about $1 \times 10^9$ to about $5 \times 10^9$ cells. Cells are administered in one infusion, or through successive infusions over a defined time period sufficient to generate a therapeutic effect. Different populations of cells may be infused when treatment involves successive infusions. A pharmaceutically acceptable carrier, as further described below, may be used for infusion of the cells into the patient. These will typically comprise, for example, buffered saline (e.g., phosphate buffered saline) or unsupplemented basal cell culture medium, or medium as known in the art.

6.7 Adjunctive Treatments

A variety of adjunctive treatments may be used with the cells, expanded or unexpanded, described above. For treating neutropenia and related conditions, the expanded cells may be used in combination with other agents and compounds that enhance the therapeutic effect of the infused cells or treat complications arising from neutropenia. In one aspect, the adjunctive treatments include, among others, anti-fungal agents, anti-bacterial agents, and anti-viral agents. Use of these agents is also suitable for thrombocytopenia, either as prophylaxis to reduce the occurrence of infections or address any ongoing infections that lead to destruction of platelets.

In one aspect, the adjunctively administered agent is an anti-fungal agent. Fungal infections are one of the major causes of mortality in patients suffering from neutropenia, being a significant problem in patients who have undergone myeloablative therapy and HSCT. Recipients with delayed engraftment and patients who develop GVHD typically have prolonged neutropenia, and thus are at high risk for fungal infections. Types of fungal infections are varied, and include, among others, candidiasis (e.g., with *candida krusei, candida glabrata, candida albicans, candida tropicalis*), aspergillosis (e.g., with *aspergillus fumigatus, aspergillus flavus*), mucormycosis (e.g., with *rhizobium arrhizus, absidia corymbifera, rhizomucor pusillus*), cryptococcosis, *histoplasma capsulatum*, and *coccidioides immitis*.

Anti-fungal agents for adjunctive administration will generally be a systemic antifungal agent. One useful antifungal agent of this type is amphotericin B from the family of polyene macrolide antibiotics. Amphotericin B is available in various formulations, including as a complex with deoxycholate; in a colloidal suspension with cholestearyl sulfate; and encapsulated in liposomes made of soy lecithin, cholesterol, and distearoylphosphatidylglycerol. Other formulations are known in the art.

Another antifungal agent is flucytosine, a fluorinated pyrimidine. Deamination of flucytosine by the fungus generates 5-flurouracil, an anti-metabolite and DNA synthesis inhibitor. Flucytosine is typically used for infections of *cryptococcus* and candiadosis. Although used alone, flycytosine is generally used in combination with amphotericin B.

Imidazoles and triazoles represent a broad class of azole based antifungal agents. It is believed that imidazoles and triazoles inhibit sterol 14-α-demethylase, resulting in impaired biosynthesis of ergosterol and disruption of cell membrane based activities, such as electron transport. Azole based antifungals are effective against certain types of candiadosis, such as *candida albicans, candida glabrata*, and *candida neoformans*. Exemplary azole antifungals suitable for systemic administration include, among others, ketoconzaole, itracanazole, fluconazole, econazole, voriconazole, and tercanozole.

In addition to fungal infections, a patient with neutropenia is susceptible to infection with a variety of bacterial pathogens. Patients undergoing myeloablative regimens and HSCT have high rates of bacterial infection with both Gram positive (e.g., *streptococcus* and *staphylococcus aureus*) and Gram negative bacteria (e.g., *E. coli.* and *pseudomonas aeruginosa*). Septecemia is a common occurrence. In addition, delayed engraftment and impaired restoration of immune responses against encapsulated bacteria, such as *streptococcus pneumoniae* or *haemophilus* influenza, increases the morbidity rate for transplant recipients with GVHD.

Adjunctive antibacterial therapy can use any known antibiotics suitable for the particular bacterial pathogen. These include both wide spectrum antibiotics and more targeted anti-bacterial compounds. Various classes of anti-bacterial agents suitable with the expanded myeloid cells include, by way of example and not limitation, quinolones and fluoroquinolones, β-lactam antibiotics, aminoglycosides, tetracyclins, macrolides, and various cogeners thereof. Exemplary quinolone compounds include ciprofloxacin, ofloxacin, sparfloxacin, lomefloxacin, and moxifloxacin. Exemplary β-lactam antibiotics include penicillins (e.g., penicillin G, penicillin V), ampicillin, carbenicillin, methicillin, carbapenem, and cephalosporins (e.g., cephalothin, cefamandole, cefaclor, cefonicid, cefotetan, cefatoxime, ceftazidime, ceftizoxime, cefepime). Exemplary aminoglycosides include neomycin, streptomycin, kanamycin, gentamicin, tobramycin, amikacin, and netilmicin. Exemplary macrolides include erythromycin, clarithromycin, and azithromycin. Other antibiotics will be apparent to the skilled artisan.

Viral infections are also problematic in myeloablated patients and HSCTs. Generally the increased risk of viral infection results from impaired cell mediated immunity brought on by the myeloablative therapy. Many of these infections arise from reactivation of latent virus existing in a seropositive patient or in the cells of a seropositive donor. Viruses commonly encountered include, among others, cytomegalovirus, herpes simplex virus, varicella zoster virus, herepesvirus-6, Epstein Barr virus; adenoviruses, and the like. As an adjunct to the cell infusions, anti-viral compounds selected are those appropriate to the viruses encountered by the patient. Useful antiviral compounds include, by way of example and not limitation, acyclovir, cidofovir, ganciclovir, idoxuridine, penciclovir, valganciclovir, valacyclovir, vidarabine, amantadine, rimantadine, zanamivir, fomivirsen, imiquimod, and ribavirin. Therapeutics directed against retroviruses include, among others, nucleoside reverse transcriptatse inhibitors (e.g., zidovudine, didanosine, stavudine, zalcitabine, lamividudine), non-nucleoside reverse transcriptase inhibitors (e.g., nevirapine, efavirenz, delvirudine), and protease inhibitors (e.g., saquinivir, indinavir, ritonavir, nelfinavir, amprenavir, and lopinavir).

The antifungal, antibacterial, and antiviral agents may be used as prophylaxis to reduce the occurrence of the infection, or upon appearance of the disease. Prophylaxis is particularly indicated for fungal infections common in immunosuppressed patients, and for viral infections in seropositive patients or seropositive transplant donors. Accordingly, embodiments for therapeutic purposes include combinations of the expanded or isolated myeloid progenitor cells and the antifungal, antibacterial, or antiviral compounds.

An additional adjunctive treatment for thrombocytopenia and related conditions include transfusions with platelets as a temporary measure to restore platelet count to safe levels. Transfusions are continued until recovery of platelet production by transfused cells.

In a further embodiment, the adjunctively administered agent is a cytokine or growth factor that enhances differentiation and mobilization of terminally differentiated myeloid cells, particularly granulocytes, macrophages, megakaryocytes and erythroid cells. For enhancing granulocyte development, the cytokines C-CSF and GM-CSF may be used. G-CSF is effective in accelerating engraftment and production of neutrophils in HSCT. In another embodiment, the cytokine or growth factor is thrombopoietin. Administration of TPO enhances engraftment of transplanted progenitor cells and promotes development of megakaryocytes and platelets (Fox, N et al., *J. Clin. Invest.* 110:389-394 (2002); Akahori., H. et al., *Stem Cells* 14(6):678-689 (1996)).

A variety of vehicles and excipients and routes of administration may be used for adjunctive therapy, as will be apparent to the skilled artisan. Representative formulation technology is taught in, inter alia, *Remington: The Science and Practice of Pharmacy,* 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the compounds, or mixture of thereof, or suitable salts thereof. The pharmaceutical composition may be formulated as powders, granules, solutions, suspensions, aerosols, solids, pills, tablets, capsules, gels, topical crémes, suppositories, transdermal patches, and other formulations known in the art.

As used herein, "pharmaceutically acceptable carrier" comprises any of standard pharmaceutically accepted carriers known to those of ordinary skill in the art in formulating pharmaceutical compositions. Thus, the compounds, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

While any suitable carrier known to those of ordinary skill in the art may be employed in the compositions, the type of carrier will typically vary depending on the mode of administration. The therapeutic compositions may be formulated for any appropriate manner of administration, including for example, oral, nasal, mucosal, rectal, vaginal, topical, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above. Alternatively, a pharmaceutical composition may be stored in a freeze-dried condition requiring only the addition of a sterile liquid carrier immediately prior to use. In a preferred embodiment, a pharmaceutical composition is provided comprising the subject expanded myeloid progenitor cells cryopreserved in a suitable cryopreservation medium, which can then be thawed and resuspended as needed for administration to a patient.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease.

Determining the dosages and times of administration for a therapeutically effective amount are well within the skill of the ordinary person in the art. For example, an initial effective dose can be estimated from cell culture or other in vitro assays. A dose can then be formulated in animal models to generate a circulating concentration or tissue concentration, including that of the $IC_{50}$ as determined by the cell culture assays.

In addition, toxicity and therapeutic efficacy are generally determined by cell culture assays and/or using experimental animals, typically by determining a $LD_{50}$ (lethal dose to 50% of the test population) and $ED_{50}$ (therapeutically effectiveness in 50% of the test population). Guidance is found in standard reference works, for example, *Goodman & Gilman's The Pharmacological Basis of Therapeutics*, 10$^{th}$ Ed. (Hardman, J. G. et al., eds.) McGraw-Hill, New York, N.Y. (2001).

For the purposes of this invention, the methods of administration are chosen depending on the condition being treated, the form of the subject antibodies, and the pharmaceutical composition. Administration of the therapeutic compounds can be done in a variety of ways, including, but not limited to, subcutaneously, intravenously, intraperitoneally, intramuscularly, and possibly direct injection to specified organs such as e.g., spleen or bone marrow, although systemic administration is preferred. Administration of the pharmaceutical compositions may be through a single route or concurrently by several routes.

The compositions may be administered once per day, a few or several times per day, or even multiple times per day, depending upon, among other things, the indication being treated and the judgement of the prescribing physician.

Kits

Other embodiments of the compositions described herein are kits comprising the expanded and/or isolated myeloid progenitor cells, cytokines and growth factors (e.g., G-CSF, GM-CSF, TPO) and/or adjunctive therapeutic compounds. A label typically accompanies the kit, and includes any writing or recorded material, which may be electronic or computer readable form (e.g., disk, optical disc, memory chip, or tape) providing instructions or other information for use of the kit contents.

7. EXAMPLES

7.1 Example 1: Experimental Methods

Preparation of HSC Cells from Mice.

For obtaining mouse bone marrow cells, animals are euthanized and the femur/tibia removed and cleaned of muscle. The bones are crushed into a pulp using a pestle and mortar, the marrow filtered through a nylon screen, and then centrifuged at 1200 RPM for 5 minutes. Cells are resuspended in 1 ml ACK solution (0.3M $NH_4Cl$, 0.2M $KHCO_3$, MiliQ filtered water) for 3-4 minutes on ice, and then washed by filling the tube with staining media (HANKS buffered saline containing 2% FCS and 2 mM EDTA, w/o calcium, w/o magnesium, w/o phenol red). Cells are centrifuged, filtered, and resuspended in staining media, and mouse IgG (1:50 dilution of a 1 mg/ml stock, Sigma, St Louis Mo.) are added. Cells are incubated on ice for 10-15 minutes and then mixed with CD117 microbeads (Miltenyi Biotech, Auburn Calif.) at a volume of 10 µl/mouse in a final volume of 100 µl/mouse staining media. Cells are incubated on ice for 25 minutes. Cells are washed, resuspended in staining media at a final volume ~1 ml/mouse, and filtered through a nylon screen. Cells are enriched using an AutoMACs (Miltenyi, Auburn, Calif.), according to manufacturer's directions using the posselds setting.

Following enrichment, cells are resuspended at about $1 \times 10^8$ cells/ml in staining media and the following directed conjugated antibodies (eBioscience, San Diego, Calif.) are added at the appropriate concentration: Sca-1 allophycocyanin (APC), c-kit R-phycoerythrin-cyanine 7 tandem (PE-Cy7), Thy-1.1 fluorescein isothiocyanate (FITC), lineage (CD3, CD4, CD5, CD8, B220, mac-1, Gr-1, and Ter119) R-phycoerythrin (PE).

Cells are incubated on ice for 25 minutes, washed, centrifuged, and resuspended in staining media. Propidium iodide (PI) is added to exclude dead cells. Mouse KTLS-HSC, c-kit$^{high}$Thy$^{low}$Sca-1$^{pos}$lineage$^{neg}$ are isolated by FACS.

Cell Culture and Expansion.

Lin$^{neg/low}$ KTLS-HSC are sorted from BA mice (H2kb) and plated in 500 ul/well serum-free medium containing the cytokine and growth factor combination c-KitL, FL, TPO and IL-6 (X-Vivo15 basal medium (Cambrex Bioscience, MD); penstrep (100×), glutamax (100×), 2-mercaptoethanol (5×10$^{-5}$M), c-KitL (50 ng/ml), FL (30 ng/ml), TPO (5 ng/ml), and IL-6 (long/ml) (Biosource, Camarillo, Calif. and R & D Systems, Minneapolis, Minn.). The cells are plated at about 10,000 cells/well in 24 well plates. The cells are cultured for 7 days to obtain MP$_c$ (culture-derived MP). Cells are fed with 500 ul/well on day 2, and on day 4 half of the media is replaced with fresh media. On day 5, cells are transferred to 6 well plates with an addition of 1 ml fresh media. On day 7, the cultured cells are collected and two small aliquots are removed for analysis. The aliquots are mixed with 30,000 beads and stained to analyze for MP (CMP/GMP/MEP) and HSC content. In addition, cell are stained with trypan blue and counted on a haemocytometer. The analysis data provides information for calculating fold expansion and total cell numbers of HSC and MP (CMP/GMP/MEP).

Analyzing In Vitro Cultures for Myeloid Cell Types.

A suspension of 6.7 µM beads (Spherotech, Libertyville, Ill.) is prepared by adding 4-5 drops of beads to 1 ml of staining medium (SM). Beads are counted using a hemocytometer and trypan blue (1:10 dilution). Beads are at a stock concentration >2×10$^6$ beads/ml and counted daily before use when using the suspension over multiple days. Using a pipette, 20K beads are added to each well of cells to be analyzed. Bead suspension is vortexed between each sample prior to adding beads to the wells. If wells are to be split into multiple samples, i.e., 3 samples, appropriate number of beads is added back (i.e., 3×20K beads for normal sample=60K/well), so that each sample will have an endpoint of about 20K beads for analysis.

Staining for Mouse HSC in Expanded Cell Populations with IL7R Staining:

Cells are removed from each well, washed and then transferred to a corresponding conical FACS tube. Cells are centrifuged for 5 min @ 1100 rpm, and the supernatant removed. 50 ul of blocking antibody (rat IgG and Mouse IgG 1:50) is added, incubated for 10 min, followed by addition of 50-100 ul of CD117-biotin (2× concentration) to each tube. Following incubation on ice for 20 minutes in the dark, cells are washed with 2-3 ml SM, centrifuged, and resuspended in 50-100 pl of the following antibody solution using appropriate concentrations of antibodies (eBioscience, San Diego, Calif.): Streptavidin Cascade Blue (Molecular Probes, Eugene, Oreg.), Sca-1 allophycocyanin (APC), Thy-1.1 fluorescein isothiocyanate (FITC), IL-7Rα R-phycoerythrin (PE) and B220, Mac-1, GR-1 R-phycoerythrin-cyanine 7 tandem (PE-Cy7). Following incubation on ice for 25 minutes, cell are washed, centrifuged, and resuspended in staining media containing P1. Cells are analyzed for HSC by FACS.

Staining for mHSC in Expanded Cell Populations without IL7R Staining.

Cells are removed from each well, washed and then transferred to a corresponding conical FACS tube. Cells are centrifuged for 5 min @ 1100 rpm, and the supernatant removed. 50 ul of blocking antibody (rat IgG and Mouse IgG 1:50) is added followed by 50-100 pl of antibody solution using appropriate concentrations of the following antibodies (eBioscience, San Diego, Calif.): Sca-1 allophycocyanin (APC), Thy-1.1 fluorescein isothiocyanate (FITC), c-kit phycoerythrin-cyanine 7 tandem (PE-Cy7), B220, Mac-1, GR-1 R-phycoerythrin. Following incubation on ice for 25 minutes, cell are washed, centrifuged, and resuspended in staining media containing P1. Cells are analyzed for HSC by FACS.

Staining for Myeloid Progenitors in Culture Expanded Cell Populations:

Cells are prepared in the same manner as done for staining of HSC cells described above. After incubation with 50 ul of blocking antibody (rat IgG and Mouse IgG 1:50), 50-100 ul of CD117-biotin (2× concentration) is added to each tube, followed by 20 minutes on ice in the dark. Cells are washed with 2-3 ml SM, centrifuged, and then resuspended in 50-100 pl of antibody solution at appropriate concentrations: Streptavidin Cascade Blue (Molecular Probes, Eugene, Oreg.), Sca-1 allophycocyanin (APC), CD34 fluorescein isothiocyanate (FITC), 2.4G2 (FcγR) R-phycoerythrin, and B220, Mac-1, GR-1 phycoerythrin-cyanine 7 tandem (PE-Cy7). (eBioscience, San Diego, Calif.). Cells are prepped for FACS analysis as done for HSC analysis.

Staining Culture Expanded Cells for Mature Progenitor Cell Subsets:

Cells are processed as described above. Following incubation with blocking antibody, 50-100 ul of CD3-biotin, CD4-Biotin, and CD8-Biotin (2× concentration) are added to each tube and incubated for 20 minutes on ice in the dark. Cells are washed with 2-3 ml staining media, centrifuged, and resuspended in 50-100 pl of antibody solution: Streptavidin Cascade Blue (Molecular Probes, Eugene, Oreg.), B220 (FITC), Ter119 R-phycoerythrin (PE) and Mac-1, GR-1 R-phycoerythrin-cyanine 7 tandem (PE-Cy7) (eBioscience, San Diego, Calif.)). Following incubation on ice for 25 min, cells are processed for FACS analysis as described previously.

Mouse Myeloid Progenitor Cell Isolation—Lineage Depletion.

Femur and tibia are processed as described above, and the cells resuspend in 1 ml of staining media. Blocking rat and mouse IgG (1:50) is added, and the mixture incubated on ice for 10-15 minutes. Cells are counted and brought up to 10$^8$ cells/ml in staining media with the following biotinylated antibodies at predetermined dilutions: D3, CD4, CD5, CD8, CD127, Ter119, Thy-1.1, and GR-1. Cells are incubated on ice for 25 minutes, washed, centrifuged, and then resuspended in 40 ul/mouse streptavidin beads (Miltenyi, Auburn, Calif.). Staining media is added to a final volume on 100 µl/mouse, incubated on ice for 20 minutes, cells washed twice and resuspended at 10$^8$ cells/ml in staining media. This is followed by filtration through a nylon mesh. Lineage positive cells are depleted using an AutoMacs (Miltenyi Biotech, Auburn, Calif.) as per manufacturers instructions using sensitive depletion mode. After counting, the cells are resuspended at 1×10$^8$ cells/ml in staining media containing the following antibodies at the appropriate concentrations: streptavidin phycoerythrin-cyanine 5 tandem (PE-Cy5), Sca-1 allophycocyanin (APC), CD34 fluorescein isothiocyanate (FITC), 2.4G2 R-phycoerythrin (PE) and c-kit R-phycoerythrin-cyanine 7 tandem (PE-Cy7) (Pharmingen and eBioscience, San Diego, Calif.). Cell are incubated with antibody for 25 minutes on ice, washed, centrifuged, and resuspended in staining media containing PI. Following FACS sorting strategy is used: CMPs are sorted based on lineage$^{neg/lo}$c-kit$^{pos}$Sca-1$^{neg}$CD34$^{pos}$2.4G2$^{low}$; GMPs are sorted based on lineage$^{neg/lo}$c-kit$^{pos}$Sca- $1^{neg}CD34^{pos}2.4G2^{pos}$; and MEPs are sorted based on lineage$^{neg/lo}$c-kit$^{pos}$Sca-$1^{neg}CD34^{low}2.4G2^{low}$.

Growth and Inoculation of *Aspergillus fumigatus* Conidia and Fungal Load Analysis:

A loop of spores from a frozen spore stock is placed onto the middle of a Sabourauds dextrose agar (SDA) culture plate, and the plate sealed and incubated at 37° C. for 2-3 days with periodic checking for any sign of contamination. After 2-3 days a lawn of black spores forms on the plate. The plate is gently rinsed with 5 ml of PBS containing 0.05% Tween 80, and the plate gently scraped until the spores are dispersed into the solution. Spore stock is made by filtering the conidia suspension through sterile gauze to remove hyphae. The solution is dark from the spores and can contain up to $10^8$ conidia per ml. Spore stocks are stored at 4° C. To titrate the spores, serial dilutions are made in PBS/Tween 80 and plated on SDA plates. Following an overnight incubation, the plates are examined for number of colonies. For long-term storage of spores, one volume of the harvested stock spores is mixed with a one volume of 50% glycerol and stored at −80° C.

Injection of the spores into mice is carried out using a conidia solution containing 1,000 conidia per ml (as titrated on Sabourauds dextrose agar plates). Working spore solution (100 μl) is injected intravenously using tail vein injections into the mice of interest, typically 8 days in the prophylactic studies, after lethal irradiation and reconstitution with HSC and/or MP. Following administration, an 100 pl aliquot of the remaining spore solution is plated onto a Sabouroud dextrose agar plate and incubated at 37° C. Colonies are counted the next day to confirm the presence of the required amount of active conidia in the injection.

Fungal Load Analysis.

Following anesthesia with inhaled isoflurane, *Aspergillus* is injected intravenously using the tailvein. Mice are sacrificed and lungs harvested for examination. Lungs are cultured onto Sabourand dextrose agar plates to detect fungal growth.

Screening Reconstituted Mice for Presence of Donor Cells.

Screening of mice transplanted with mHSC's and/or mMP's for donor cell population is done by collecting approximately 10-15 drops of blood in 0.5 ml 5 mM EDTA in PBS at room temperature. One ml of 2% dextran-500 in PBS is added, mixed, and incubated at 37° C. for 30-45 min. Most red blood cells will settle. The resulting supernatant is transferred to a new tube, the cells collected by centrifugation (5 min, 1000 rpm), and red blood cells lysed with 1.0 ml of 1×ACK for 5-6 minutes on ice. This is followed by a wash and centrifugation for 5 minutes at 1200 rpm. If the pellet is still red, the wash steps are repeated. Cells are blocked with rat IgG and mouse IgG (1:50 each) in 50 ul/tube for 10 to 15 minutes on ice. Biotinylated Mac-1 and GR-1 (eBioscience, San Diego, Calif.) are added at the appropriate concentration, and incubated on ice in the dark for 20 minutes. Cells are washed and centrifuged for 5 minutes at 1200 rpm. The following antibodies are added at the appropriate concentrations: Streptaviden Cascade Blue (Molecular Probes, Eugene, Oreg.), CD45.1 allophycocyanin (APC), CD45.2 fluorescein isothiocyanate (FITC), B220 R-phycoerythrin cyanine tandom (PE-Cy7) and CD3, CD4, CD8 R-phycoerythrin (PE) (eBioscience, San Diego, Calif.). Following a 25 minute incubation on ice, cells are washed, centrifuged, and resuspended in SM containing P1. Cells are analyzed by FACS.

Screening Reconstituted Mice for Donor Cells Using H2 Markers.

Approximately 10-15 drops of blood are collected in 0.5 ml 5 mM EDTA in PBS at room temperature. One ml of 2% dextran-500 in PBS (RD is added and the mixture incubated at 37° C. for 30-45 min. Most red blood cells will settle. The supernatant is transferred to a new tube, and cells collected by centrifugation (5 min, 1000 rpm). Red blood cells are lysed with 1.0 ml of 1×ACK ($0.3M$ $NH_4Cl$, $0.2M$ $KHCO_3$) on ice for 5-6 minutes, followed by a wash and then a centrifugation for 5 minutes at 1200 rpm. If the pellet is still very red, steps 4-5 are repeated. Cells are blocked with rat IgG and mouse IgG (1:50 each) in 50 ul/tube for 10 to 15 minutes on ice. Cells are stainted for 20 minutes with the following antibodies: Mac-1 and GR-1 phycoerythrin-cyanine 7 tandem (PE-Cy7), B220 allophycocyanin (APC), CD3, CD4 and CD8 biotin (eBioscience, San Diego, Calif.).

Additional antibodies are used to label MHC markers depending on the mice pairing used for transplant: H2Kd-PE (Balb/c) and H2Kb-FITC (C57/B6) or H2Db-PE (C57/B6) and H2Dk-Fitc (AKR). Cells are prepared by centrifuging for 5 minutes at 1200 rpm and then stained with Streptavidin Cascade Blue (Molecular Probes, Eugene, Oreg.). Following a 20 minute incubation on ice, cells are washed, centrifuged for 5 minutes at 1200 rpm, and then stained with P1. Cells are analyzed by FACS.

7.2 Example 2. Ex Vivo Expanded Cryopreserved Allogenic Myeloid Progenitors Protect Against Lethal Fungus in Neutropenic Mice This study examined whether HSC can be expanded into large numbers of functional myeloid progenitors ex vivo; whether ex vivo expanded myeloid progenitors protect allogeneic neutropenic mice from lethal fungus comparable to the protection provided by myeloid progenitors sorted from BM; and shows myeloid progenitors can be cryopreserved without loss of activity.

FIG. 1A-1C is an exemplary experimental design. FIG. 1A shows cell populations sorted and analyzed, different marker combinations can distinguish HSC and progenitors. $CD117^+$, $CD90.1^{lo}$, $Lin^{neg/lo}$ and $Sca-1^+$ can be used to identify HSC. $CD117^+$, $Lin^{neg/lo}$ and $Sca-1^{neg}$ can be used to identify a mixed population of myeloid progenitors. The individual subpopulations (CMP, GMP and MEP) can be distinguished by their CD16/CD34 profile. FIG. 1B shows derivation of myeloid progenitors from HSC in culture. Culture derived MPc can be used fresh or cryopreserved. FIG. 1C shows the use of myeloid progenitors to protect neutropenic mice from a fungal challenge. Several parameters, such as the strains used, time of infection and the number of cells used vary between experiments. Typical experiments use BALB/c hosts and C57BL/Ka MP donors.

Mice.

C57BL/6 Ka, Thy-1.1, CD45.2 mice were bred and maintained at the Research Animal Facility of Stem Cells Inc, Palo Alto, Calif. BALB/c mice were purchased from Charles River Laboratories. Donor mice were used 6-8 weeks old, recipient mice 8-16 weeks old.

Recipient mice were irradiated with a Cs irradiator. BALB/c recipients received a total of 9.2Gy given in two doses at least 3 hours apart. All mice were maintained on acidified water and were switched to water containing antibiotics (106 U/L polymyxin B sulfate and 1.1 g/L neomycin sulfate) for 4 weeks post-irradiation to reduce opportunistic infections.

Fungal Infections.

A clinical isolate of *Aspergillus fumigatus*, that has been previously described (BitMansour A, et al., *Blood* 100, 4660-4667) was used to infect mice. Briefly, the fungus was plated onto Sabouraud dextrose agar (BD Biosciences, Cockeysville, Md.) and incubated for at least 48 hours at 37° C. The conidia were harvested by pouring 10 ml PBS+ 0.05% Tween80 on the fungal lawn. After gentle scraping the resulting solution was filtered to remove hyphae and the resulting conidia solution was maintained at 4° C. Plating of serial dilutions on Sabouraud agar plates was used to determine the conidia concentration. Mice challenged with *A. fumigatus* received between 100-200 conidia injected i.v. into the tail-vein in a total of 150 µl saline.

Flow Cytometry.

KTLS HSC were prepared by flushing bone marrow from femurs and tibiae of mice, followed by ammonium chloride lysis of the red blood cells. The resulting cell suspension was enriched for $CD117^+$ cells using an AutoMacs device and CD117-microbeads (Miltenyi Biotec). The enriched cells are stained for CD117PE-Cy7 (2B8), $CD90.1^{FITC}$ (HIS51), LinPE (CD3 (145-2C11), CD4 (L3T4), CD5 (53-7.3), CD8 (53-6.7), CD19 (ID3), B220 (RA3-6B2), CD11 b (M1/70), Gr-1 (8C5) TER119 (TER119) and Sca-1APC (D7) (EBioscience, San Diego, Calif.). $CD117^+$, CD90.1lo, $Lin^{neg/lo}$ and $Sca-1^+$ cells were double sorted (yield sort followed by a purity sort) using a Becton and Dickinson FACSAria. HSC from CD90.2 strains (e.g. BALB/c) are sorted without CD90 staining as KLS cells.

Bone marrow derived myeloid progenitor cells, a mix of CMP, GMP and MEP were sorted from mouse bone marrow by enriching bone marrow for $CD117^+$ cells as described above. The cells are stained and CD117+, $Lin_{neg/lo}Sca-1^{neg}$ cells were sorted.

Tissue Culture.

Ten thousand $Lin^{neg/lo}$ KTLS HSC are sorted from mouse bone marrow and plated in 24 well-plates containing 0.5 ml X-vivo15 (Cambrex) supplemented with 1% Penicillin/Streptomycin (Biosource), 1% Glutamax (Invitrogen) and 50 ng/mlc-KitL, 5 ng/ml Tpo, 10 ng/ml IL-6 (Biosource) and 30 ng/ml Flt3L (R&D Systems). All growth factors are mouse recombinant. Media is added every other day. 50% of the medium is replaced on day 4, at which point the cells are replated into a 6 well plate. At the time of harvest on day 7 the total culture volume is 2 ml. containing $2-7 \times 10^6$ cells. Cells are analyzed for the presence of mature progenitor cells as described above, and either used fresh or cryopreserved. Cultured cells were cryopreserved in 7.5% DMSO, 42.5% Fetal Bovine Serum and 50% Xvivo15 medium. Upon thawing the cells were quantitated using a viable cell count (trypan blue) followed by flow cytometric analysis to confirm that the freeze thaw process had not affected the progenitor profiles, prior to injection into irradiated mice.

HSC Expanded Ex Vivo into Functional Myeloid Progenitors.

In order to develop a clinical useful therapy it is desirable to generate myeloid progenitors in large amounts. Highly purified KTLS HSC were sorted and deposited in serum-free medium (X-vivo15) supplemented with growth factors that act on HSC. A number of different cytokine combinations were tested (data not shown). The combination of KitL, Flt3L, Tpo and IL-6 induced rapid proliferation but only slow differentiation of the plated HSC, such that over a one week period total cell expansion for C57BL/Ka derived HSC averaged 500-fold. Flow cytometric analysis of the cells at the end of seven days in culture indicates that a significant proportion of the cells have the surface phenotype of various myeloid progenitors (CMP, GMP and MEP) as well as HSC (as indicated in FIG. 2B). FIG. 2B shows average expansion numbers as observed for C57BL/Ka cells and similar total expansions were observed with HSC from several other strains including AKR, FVB and SJL. Transplantation experiments show that while significant numbers of HSC were present after 5 days of culture, few functional HSC remained after C57BL/Ka HSC were cultured for 7 days.

On average the expansion of the various progenitor populations, combined in the $CD117^+Lin^{neg/lo}$ gate, averaged about 100-fold over the number of KTLS-HSC plated under the conditions used. Thus, these culture conditions resulted in significantly more MP than can be directly purified from mouse bone marrow. Furthermore, using methylcellulose plating of single cells, the progenitor populations identified by surface marker phenotype have the expected lineage differentiation potential (data not shown)

In addition to the various well-defined myeloid progenitors these cultures also contain more differentiated cells, including a small number of relatively mature megakaryocytes. However, as can be seen in FIG. 2A, the majority of cells, while showing signs of myeloid commitment, are not terminally differentiated and many retain the blast cell characteristics of stem and progenitor cells. FIG. 2A shows May-Grünwald/Giemsa stained cytospins of a day 7 culture, most cells are immature, many clearly myeloid committed. Low numbers of relatively mature megakaryocytes are present. FIG. 2B show the yield of different types of progenitors, as defined by surface marker profile, from HSC after 7 days in serum-free culture.

Ex Vivo Expanded Myeloid Progenitors Protect Allogenic Neutropenic Mice from Invasive *Aspergillus*.

Bone marrow derived myeloid progenitors have been used to protect neutropenic mice from fungal infection. This example shows that culture derived myeloid progenitors protect allogenic neutropenic mice from invasive fungal infections similar to bone marrow derived myeloid progenitors.

Figure 3:
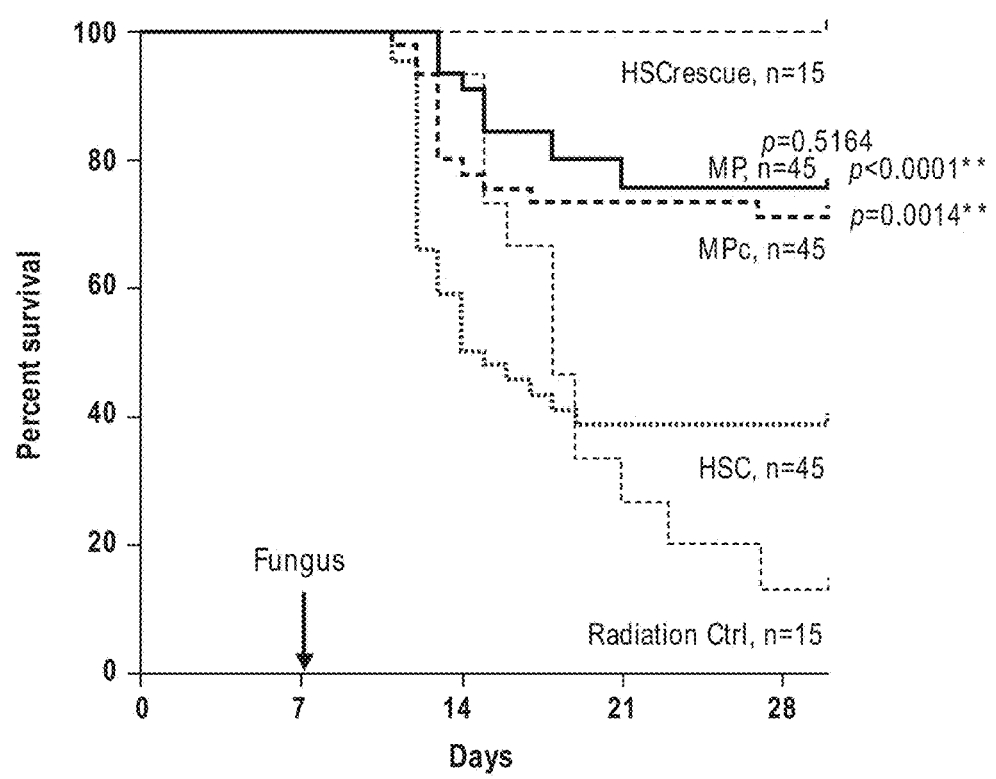
FIG. 3 shows protection of neutropenic mice by allogeneic culture-derived myeloid progenitors.

Reconstitution was performed in lethally irradiated mice (BALB/c, CD90.2, $CD45.2,H-2^d$) with 200 syngeneic BALB/c HSC ($CD117^+$, $Lin^{neg/lo}$, $Sca-1^{neg}$, KLS) and either $8 \times 10^4$ bone marrow MP sorted as $CD117^+$, $Lin^{neg/lo}$, $Sca-1^{neg}$ cells from C57BL/Ka, $H-2^b$ bone marrow or $5 \times 10^5$ Day 7 culture derived MPc cells. The mice were infected, by tail vein injection, with 150 conidia of a clinical isolate of *Aspergillus fumigatus* 7 days after the initial irradiation and HSC/MP transfusion. The experiment was repeated three times with 15 mice per group (data not shown). As shown in the pooled data in FIG. 3, only 2/15 irradiation controls survived for more than 30 days, confirming that the lethal irradiation dose used is relatively low. Injection of 200 KLS HSC at day 0 (HSC-rescue group) fully rescues the irradiated mice; however, only 17/44 of these mice survive injection of 150 *A. fumigatus* conidia. In contrast, 34/45 mice (76%) that received BM MP and 32/45 mice (71%) that received culture-derived cells survived the fungal challenge and the culture-derived cells prevent death. Statistical analysis (logrank) show significant protection by both BM MP cells (p<0.0001) and culture-derived cells (p=0.0014) when compared to the stem cells only group. There is no discernable difference in the 30 day survival between the groups that received BM MP cells when and the group that received culture derived-cells (p=0.5164). Thus, ex vivo expanded myeloid progenitors protect neutropenic mice from invasive aspergillosis as well as bone marrow derived myeloid progenitors.

Cryopreserved Ex Vivo Expanded Allogenic Myeloid Progenitors Protect Against Aspergillosis in Neutropenic Mice.

An advantage of the use of myeloid progenitors, in contrast to mature granulocyte infusions, is the ability to cryopreserve progenitors cells prior to use. The frozen MP cells could be stockpiled and thawed when needed.

This study is adapted from the standard Fungus experiments with murine MPc. The standard design is to culture C57BL/Ka HSC for 7 days in Xvivo15 supplemented with KitL, Flt3L, Tpo and IL-6. On day 0 the host mice (BALB/c) are lethally irradiated (2×4.4Gy, 4 hours apart) and injected on the same day with $5 \times 10^5$ cells from the MPc cultures and 200 BALB/c HSC (KLS). On day 7 the mice are injected i.v. with 150 conidia of *Aspergillus fumigatus*. The mice are inspected daily and the 30 day survival is determined.

The experiments described here will differ in that (i) MPc are cultured at several different occasions (ii) the earlier cultures were frozen and stored in liquid nitrogen (iii) fresh and frozen MPc are compared (iv) composition of MPc were analyzed by flow cytometry before freezing and after thawing.

Mouse cells can be frozen in a cryopreservation media that is a serum free or a serum containing mix. For all the research experiments used a serum containing cyropreservation media. Serum containing mix: (150 ml total) with 37.5 ml serum and 22.5 ml DMSO.

1. Pellet cells
2. Resuspend cells in serum free media (IMDM or Xvivo)
3. Prepare a metal bowl with ice and water
4. Place the tube of resuspended cells in the icy water and slowly drop an equal volume of the cyropreservation mix from above to the resuspended cells while gently mixing the tube.
5. Pipet the mixture in vial and put freezing apparatus at −80 overnight
6. Transfer vial to −180 for long storage.

For thawing cultured mouse cells:

1. Thaw the vial in 37 C bath until the content is mostly thawed Resuspend cells in serum free media (IMDM or Xvivo)
2. Pipet cells slowly in vial containing DNAse, take out small aliquot to do initial vial cell count.
3. Dropwise add 10 ml of Media (IMDM/DMEM etc with 10% NCS) to cells while gently rocking the tube to allow slow mixing of media and cells.
4. Spin down cells and resuspend in staining media (HBSS/2% NCS)
5. Count

| Date | Description |
| --- | --- |
| Dec. 1, 2004 | Day -14. Sort BS.BA HSC to initiate MPc cultures (frozen MPc). |
| Dec. 8, 2004 | Day - 7. Harvest MPc, analyze by flow and freeze the cells (plate CD117+ cells in MCM/Terasaki plate). |
| Dec. 9, 2004 | Sort BS.BA HSC to initiate MPc cultures (fresh). |
| Dec. 16, 2004 | Day 0. Sort BALB/c HSC, harvest MPc cultures, irradiate 65 BALB/c mice and inject 60 BALB/c mice with MPc (fresh or frozen) and/or HSC. |
| Dec. 23, 2004 | Day 7. Inject 50 reconstituted mice with 150 conidia of *Aspergillus fumigatus* |
| 2005 | Day 5 to 30. Daily records of surviving and dying mice Test mice for level of reconstitution starting at 4 weeks |

| Group | n | HSC | MPc | Growth factor | Fungus (conidia) | Day |
| --- | --- | --- | --- | --- | --- | --- |
| G1: fresh MPc | 15 | 200 | Fresh, 500,000 | No | 150 | 7 |
| G2: frozen 11/29 MPc | 15 | 200 | Frozen 500,000 | No | 150 | 7 |
| G3: frozen 12/8 MPc | 15 | 200 | Frozen 500,000 | No | 150 | 7 |
| G4: no MP | 10 | 200 | | 0 | No | 150 | 7 |
| G5: Radiation Ctrl | 5 | | | 0 | No | | 7 |
| Totals | 60 | 11,000 | 3*7,500,000 | None | 8,250 | |

Mp-Cultures.

$CD117^+$ $CD90.1^{low}$ $Lin^{neg/lo}$ $Sca-1^+$ HSC were sorted from CD117-enriched BS.BA bone marrow as described below. Mouse HSC Isolation—directly conjugated c-kit microbeads. Collect femurs and tibia, clean of muscle. Crush using pestle and mortar. Filter through nylon screen, 5 mice/tube (10 leg bones and 10 arms). Centrifuge 1200 RPM for 5 minutes. Resuspend in 1 ml ACK~3-4 minutes on ice. Wash by filling tube with staining media. Centrifuge. Count cells. Resuspend in staining media ~50-60 μl mouse, filter, wash tip and filter with another 40-50 μl, add rat IgG (1:50)+mouse IgG (1:50) for 10-15 minutes. Remove 10 ul whole BM for staining. Add 10 μl/mouse of anti c-kit microbeads (CD117) per mouse, (lot#5040428046). Note: If humerus are added, use 12 μll beads/mouse. Incubate on ice 25 minutes. Wash 2×. Resuspend cells and filter through nylon screen final volume-0.5-1.0 ml/mouse, wash tip and filter mesh with another 0.5 ml. Enrich cells on AutoMACs, use posselds program. Alternatively, prepare Midi column by washing with 3-4 ml staining media. Filter cells through nylon mesh to apply to column. Pass cells over column 3× (no more than 10 mice/column). Wash column with 5-10 ml staining media. Remove column from magnet and flush cells from column 2×. (note: 10 mice=midi and 5 mice=mini) Count, centrifuge. Resuspend cells at $1 \times 10^8$ cells/ml in staining media plus antibodies.

| Antibody | Lot # | Titer | |
| --- | --- | --- | --- |
| c-kit (2B8) biotin | E000225 | 1:400 | Orc-kit |
| (2B8) PE-Cy7 | E009158 | 1:400 | |
| Sca-1 APC | E007871 | 1:200 | |
| Thy-1.1 FITC | E008124 | 1:400 | |
| Lineage PE: | | | |
| Ter 119 | E005015 | 1:400 | |
| CD3 | E009288 | 1:100 | |
| CD5 | E004526 | 1:1600 | |
| CD8 | E009271 | 1:200 | |
| B220 | E007026 | 1:800 | |
| CD4 | E008789 | 1:3200 | |
| Mac-1 | E005858 | 1:6400 | |
| GR-1 | E008723 | 1:3200 | |

Incubate on ice for 25 minutes, wash and centrifuge. If c-kit bio used resuspend in SM ($1 \times 10^8$ cells/ml). Stain with streptavidin Cy7-PE (Lot # E006330) 1:800 25 minutes on ice. Wash, centrifuge, resuspend in staining media+PI (1:1000) filter before FACS. Set up comp tubes based in what colors are used:

| Antibody | Lot # | Titer |
| --- | --- | --- |
| B220-PE Cy7 | E009142 | 1:400 |
| B220-Bio | E004692 | 1:800 |
| Cascade-Blue | 65A1-1 | 1:400 |

-continued

| Antibody | Lot # | Titer |
|---|---|---|
| B220-PE | E007026 | 1:400 |
| B220-FITC | E005965 | 1:200 |
| B220-APC | E011511 | 1:200 |
| B220-Cy5PE | E004592 | 1:800 |
| PI | | 1:1000 |
| No stain | | |

Stain whole BM: Centrifuge cells. Resuspend in 100 ul SM+antibodies (see above). Incubate on ice 25 minutes. Wash, centrifuge. (If 2B8-biotin is used, resuspend in 100 ul ($10^7$ cells/100 μl) and stain with streptavidin Cy7-PE 1:800 25 minutes on ice). Wash, centrifuge, resuspend in SM+PI (1:1000), filter before FACS.

Approximately $3 \times 10^4$ HSC were used to initiate MPc cultures. The cells were cultured in Xvivo15+2ME+Pen/Strep+50 ng/ml KitL+30 ng/ml Flt3L+5 ng/ml Tpo+10 ng/ml IL-6 for 7 days as described below.

Large scale mouse HSC to Myeloid Progenitor culture: $Lin^{neg/low}$ KTLS-HSC are sorted from mouse bone marrow and plated in 500 μl/well Xvivo15 supplemented with Pen/Strep, Glutamax and β-mercaptoethanol as well as KitL, Flt-3L, Tpo and IL-6. The cells are cultured for 7 days to obtain $MP_c$ (culture-derived MP). The expected expansion during this period for C57BL/Ka-cells is 200-700 fold total expansion, with 10-35% of the cells falling in the $CD117^+$ $Lin^-$ gate. Cells are sorted twice, first on yield then followed by a final sort on purity. For a 100,000 bulk sort, first sort should yield around 300,000 cells. In a 24 well plate, 10,000 KTLS-HSC are sorted directly per well in 500 μl media. Sterile water is added to the outer wells of the plate to prevent evaporation. The cells are incubated at 37° C., 5% $CO_2$ in a fully humidified incubator. On day 2, 500 μl of fresh media is added to each well. On day 4, half of the media (500 μl) is discarded (pipet carefully from the top to avoid removing cells). The cells are resuspended (pipet up and down using a P1000) and transferred to a well on a 6 well plate containing 500 μl fresh medium. The empty well on the 24 well plate is rinsed with 500 μl fresh medium, transfer this to the same well on the 6 well plate. Total volume should be 1.5 ml per well. Some cells will remain attached to the bottom of the 24 well plate, these are discarded. On day 6, add 500 μl of fresh medium. On day 7, the cultured cells are collected and analyzed. In addition, cell are stained with trypan blue and counted using a hemocytometer. The analysis data provides information for calculating fold expansion and total cell numbers of HSC and MP (CMP/GMP/MEP).

Reagents for Large scale mouse HSC to Myeloid Progenitor culture: X-vivo15 (Cambrex Bio science 04-744Q) supplemented with Penicillin/Streptomycin (100x) Biosource International Inc., Glutamax (100x) Invitrogen, β-Mercaptoethanol (1000x) Sigma Aldrich Fluka Inc. The growth factors include:

| | Manufacturer | Catalog No | Stock solution | Use at: |
|---|---|---|---|---|
| rmKitL | Biosource | PMC2115 | 25 ng/μl | 50 ng/ml |
| rmFlt3L | R&D | 427-FL | 25 ng/μl | 30 ng/ml |
| rmTpo | Biosource | PMC1144 | 10 ng/μl | 5 ng/ml |
| rmIL-6 | Biosource | PMC0066 | 10 ng/μl | 10 ng/ml |

Culture media for 100,000 cells (500 ul/well) is 5 ml complete Xvivo, 5 μl IL6, 2.5 μl TPO, 10 μl KilL, 6 μl Flt3L. For 100 ml Complete Xvivo use 100 /μβ-mercaptoethanol, 1 ML Pen/Strep, 1 ML Glutamax.

After 7 days in culture the cells were harvested and counted. Aliquots were analyzed as described below. Analyze of HSC/MP by adding 4-5 of spherotck (6.7 uM) beads to 1 ml of staining medium (SM). Dilute beads 1:10 in trypan blue, count using a haemocytometer. Beads should be at a stock concentration $>2 \times 10^6$ beads/ml. Count beads before each analysis. Add 30,000 beads per sample. Transfer a small aliquot of cells to analysis tubes. Block with rIgG (1:50) and mIgG (1:50) on ice for 10 min. To MP tubes add CD117-BIOTIN @ 1:200. Incubate for 20 min on ice in dark. Prepare HSC (Ckit cy7-pE at 1:400, Sca-1 APC at 1:200, Thy-1.1FITC at 1:200, B220 PE at 1:800, Mac-1 PE at 1:800, and GR-1 PE at 1:800) and MP (SA-cascade blue at 1:400, Sca-1 APC at 1:200, CD34 FITC at 1:25, 2.4G2 at 1:50, B220 Cy7-PE at 1:800, GR-1 Cy7-PE at 1:800) antibody mix. Wash all tubes w/2 ml sm, spin @ 1100 rpm for 5 min. Incubate with antibody mix for 20 min on ice in dark. Wash cells w/sm and spin. Rresuspend cells in PI media. [P1 media (1:1000) 10 ml stock: 10 μl PI in 10 ml sm].

Briefly, flow cytometric analysis was performed to determine the presence of HSC, CMP, GMP, MEP and more mature cells (CD11 b+, $Gr-1^+$, $Ter119^+$). Cytospins (to be stained with May-Grünwald/Giemsa stain) were made. Approximately 3 times $7.5 \times 10^7$ culture derived cells are needed for injections, fresh (1x) and frozen (2x).

Freezing of MPc.

MPc were culture-derived from HSC as described. The cells were analyzed by flow cytometry prior to freezing. In addition, single $CD117^+Lin^-$ cells were plated, either in Terasaki plates with MPc medium (Xvivo+KitL, Flt3L, Tpo and IL-6) above. The percentage of cells forming colonies will be determined one week after plating. The cells were frozen according to protocol as described below. Cells can be frozen in a cryopreservation media that is a serum free or a serum containing mix. For all the research experiments serum containing cyropreservation media was used. Serum containing mix: (150 ml total) 37.5 ml serum, 90 ml hetastarch, 22.5 ml DMSO. Pellet cells and resuspend cells in serum free media (IMDM or Xvivo). Prepare a metal bowl with ice and water. Place the tube of resuspended cells in the icy water and slowly drop an equal volume of the cyropreservation mix from above to the resuspended cells while gently mixing the tube. Pipet the mixture in vial and put freezing apparatus at −80 overnight transfer vial to −180 for long storage.

Thawing of Frozen MPc.

Frozen MPc were thawed as describd below. Thaw the vial in 37° C. bath until the content is mostly thawed Resuspend cells in serum free media (IMDM or Xvivo). Pipet cells slowly in vial containing DNAse, take out small aliquot to do initial vial cell count. Dropwise add 10 ml of Media (IMDM/DMEM etc with 10% NCS) to cells while gently rocking the tube to allow slow mixing of media and cells. Add media at approximately 1 ml/minute. Spin down cells and resuspend in staining media (HBSS/2% NCS). Then "rest" cells by leaving them at RT for 1/2 hour. Count/stain or plate cells accordingly.

In this expirment, following thawing the cells were rested for approximately 1 hour and viability determined by (i) trypan blue/haemocytometer count (ii) PI exclusion flow cytometry analysis. In addition, single $CD117^+Lin^-$ MPc were plated and cultured.

Balb/c Hsc Sort.

HSC, CD117+Lin$^{neg/low}$Sca-1$^{pos}$, were sorted from 5 BALB/c mice using as described above. 10,000 HSC (200 per recipient) were needed. The sorted BALB/c HSC were mixed with culture-derived BS.BA MPc in the desired ratio's and used for injection into lethally irradiated BALB/c mice.

Fungus Injections.

On day 7 the mice will be injected in the tail vein with 150 conidia of *Aspergillus fumigatus* as described below including the testing of part of the injection solution on Sabarouddextrose agar to quantify the number of live conidia injected. *Aspergillus* injection determine the concentration of conidia for each experiment prior to injections. Total volume of 150 μl (sterile 1×PBS+0.05% tween+conidia) is injected per mouse. During injections, keep conidia solution on ice and vortex before each syringe filling. Plate 150 μl from the syringe onto a SDA plate and incubate at 37° C. Next day count colonies to confirm the presence of conidia injected.

Figure 4A:
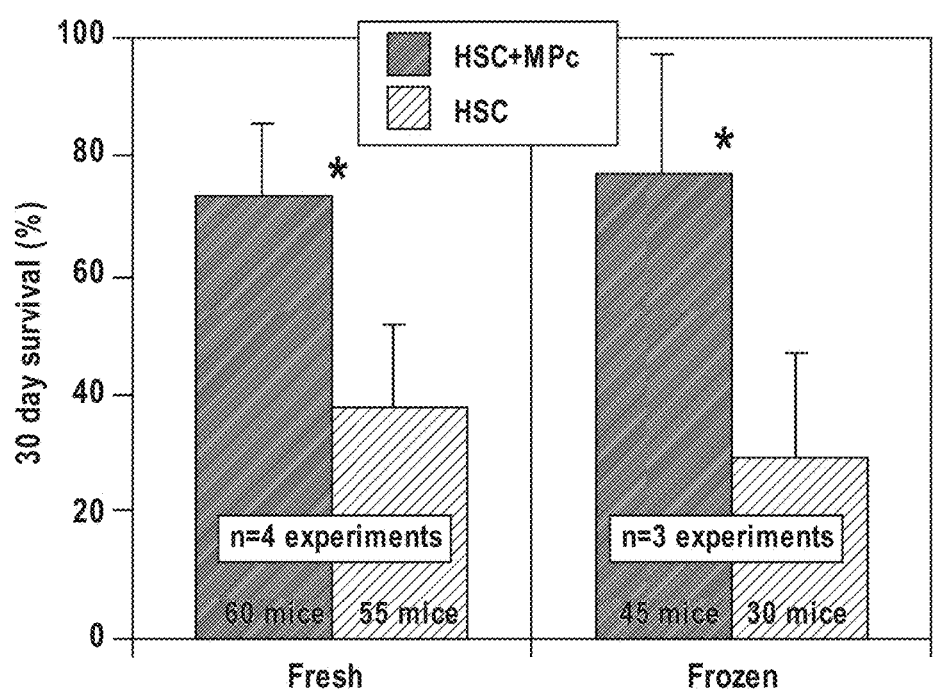

To demonstrate that culture-derived myeloid progenitors retain their ability to prevent invasive aspergillosis in neutropenic mice HSC were plated and cultured as described above. After seven days the cultures were harvested and analyzed by flow cytometry. The cells were then cryopreserved as described in the above and stored in the vapor phase of liquid nitrogen. After at least seven days the vials were rapidly thawed in a 37° C. water bath, washed twice with medium. An aliquot was removed for flow cytometric analysis and the remainder of the cells was used to inject into lethally irradiated allogeneic hosts. FIG. 4A compares survival data for fresh MP with that of culture derived myeloid progenitors that were cryopreserved prior to use, the 30 day survival of mice challenged with *A. fumigatus* conidia 7 days after lethal irradiation and reconstitution with 200 syngeneic HSC and 500,000 allogeneic culture-derived MP, used either fresh or after cryopreservation. Survival after fungal challenge in 4 groups of 15 mice that received 500,000 fresh cells differs significantly from that of mice receiving only HSC (p=0.009, t-test). The same is true for 3 groups of 15 mice that received 500,000 culture-derived myeloid progenitors that had been cryopreserved compared to HSC-only groups (p=0.0329). There is no difference in survival between the groups receiving fresh or frozen myeloid progenitors (p=0.7205) or the HSC-only groups in both cases (p=0.5058). FIG. 4B is a comparison of the CD117 Lin staining profile of the cultured MP cells before freezing and after thawing, and shows that a freeze/thaw cycle does not affect the CD117 and Lin staining profiles. Similar results were obtained in analysis for the markers (data not shown).

Reconstitution with Myeloid Progenitors Typically Results in Short-Term Engraftment.

Figure 5A:
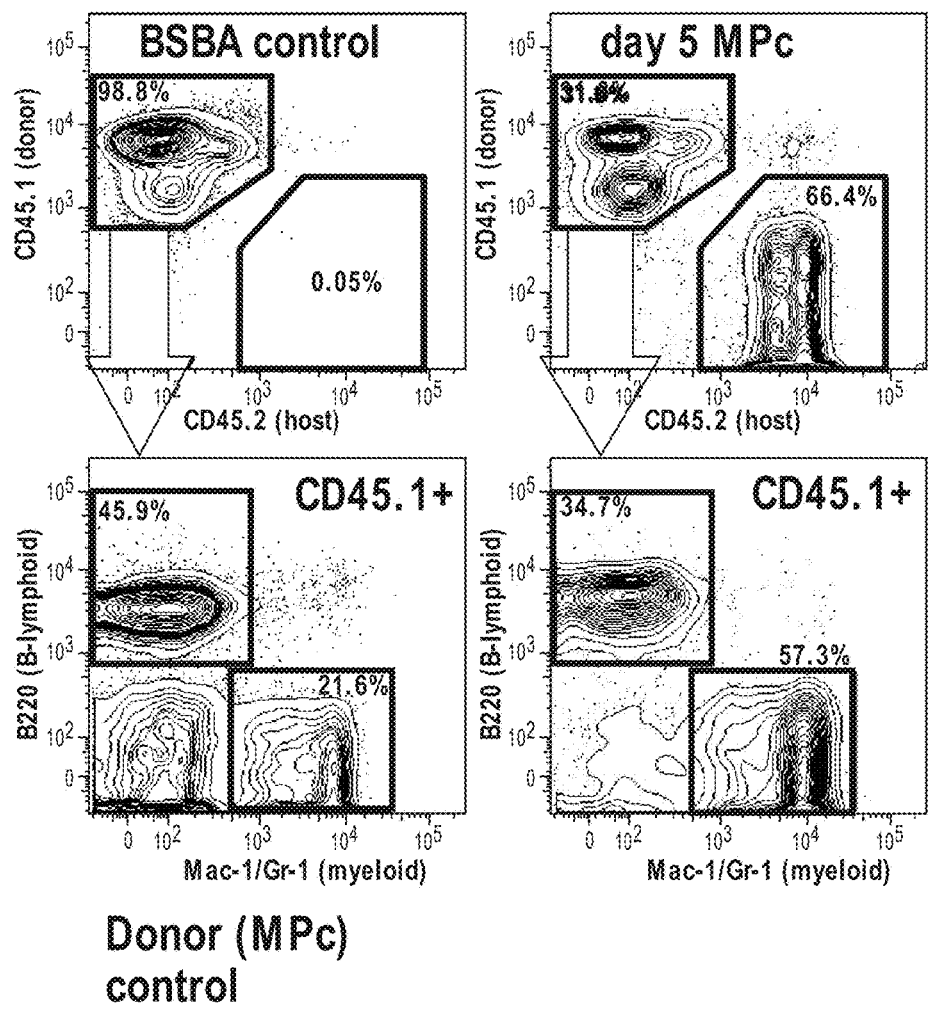
FIG. 5A-5C shows reconstitution with myeloid progenitors in mice.
Figure 5B:
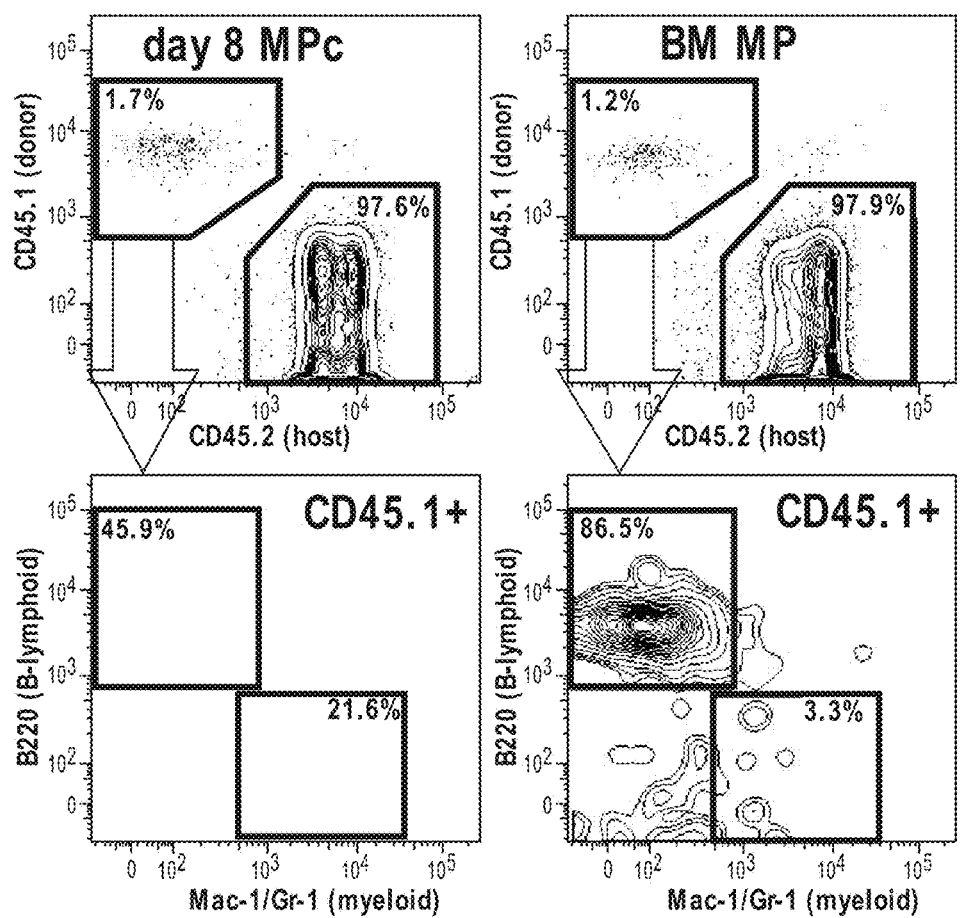
Figure 5C:
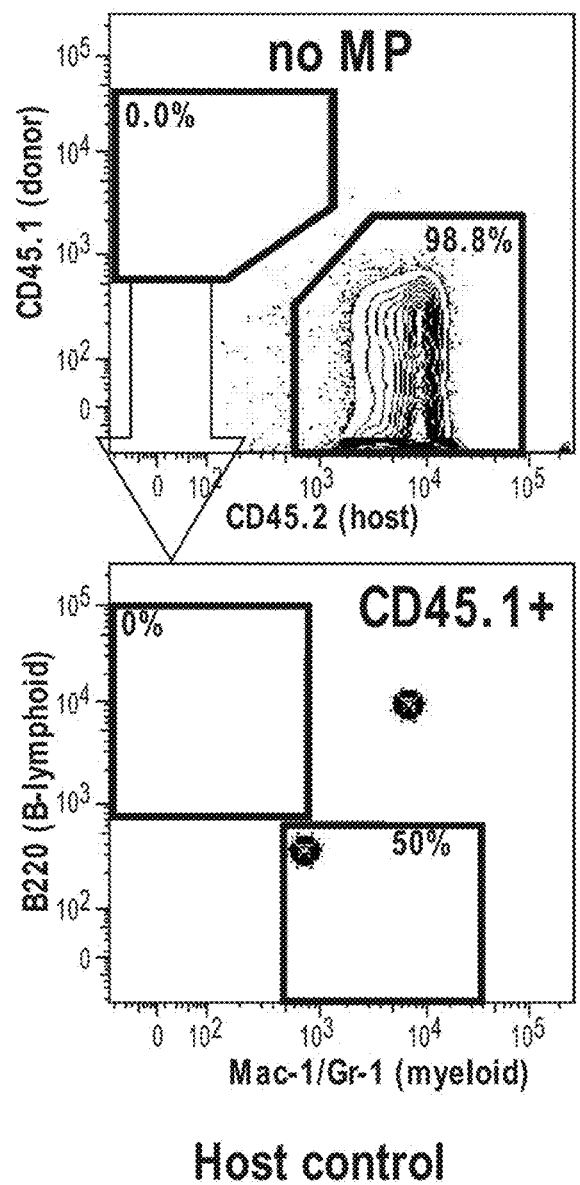

FIG. 5A-5C shows reconstitution with syngeneic MPc illustrates engraftment levels in peripheral blood at 4 weeks post-reconstitution with C57BL/Ka cells cultured either 5 days (2.25×10$^5$ cells/mouse), 7 days (8×10$^5$ cells per mouse), or sorted directly from mouse bone marrow as myeloid progenitors (4×10$^4$ cells/mouse). As shown in FIG. 5A-5C, few (five percentages) MP-derived cells are present in circulation one month after administration. MP-derived cell numbers disappear over time, and are lower at 8 weeks than at 4 weeks post administration (data not shown). The cells that are present are mostly B-lymphocytes. HSC that have been cultured for five days under MP-inducing conditions show a dramatically different pattern of reconstitution. At 4 weeks many of the circulating cells are MP-derived, and these contain cells representing the three major lineages, myeloid cells, B cells and T cells. This suggests that engraftment is by residual functional HSC. MP-derived cells numbers are significantly lower 8 weeks post-reconstitution, indicating that the engrafting HSC are mainly restricted to ST-HSC Administration of cells that have been cultured for eight days display an engraftment pattern very much like the purified myeloid progenitors. Few MP-derived cells are seen and these mainly represent long-lived B cells. Thus, the number and type of donor-derived cells was related to the duration of culture and seven days of culture results in few MP-derived cells being detected in the host 8 weeks after infusion.

Figure 6B:
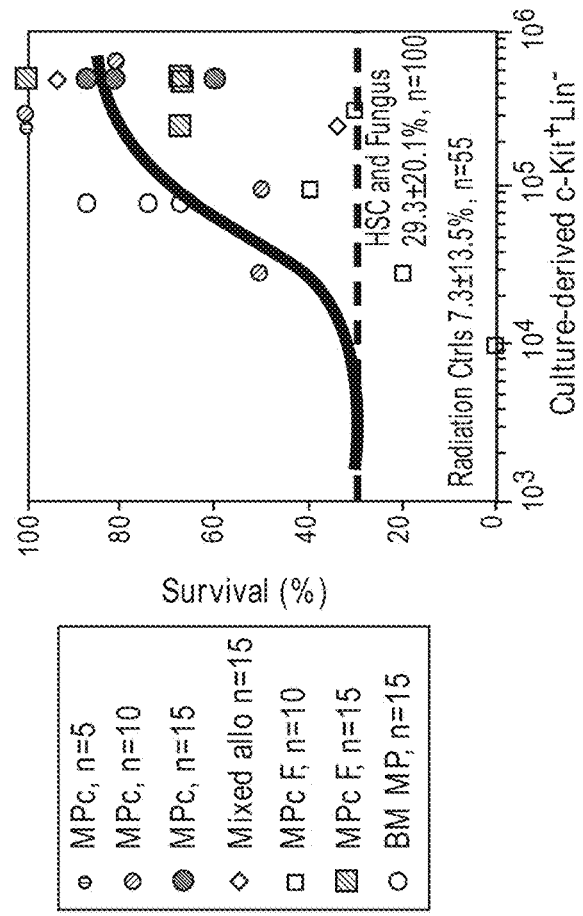
FIG. 6A-6B shows dose response of protection by culture-derived myeloid progenitors.
Figure 6A:
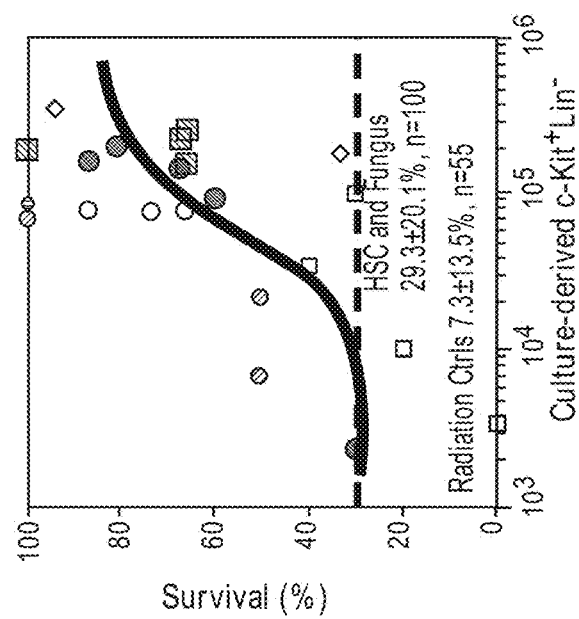

FIG. 6 shows dose response of protection by culture-derived myeloid progenitors. Combined data from ten independent experiments. Doses are either plotted as total cell numbers (FIG. 6A) or CD117+Lin− cells in the MPc (FIG. 6B). These experiments were performed as described for FIG. 5A-5C. BALB/c mice were lethally irradiated and injected with BALB/c HSC and C57BL/Ka MPc, followed by challenge with *A. fumigatus* conidia at D+7.

Cultured Myeloid Progenitors Rapidly Provide Effective Protection.

Figure 7:
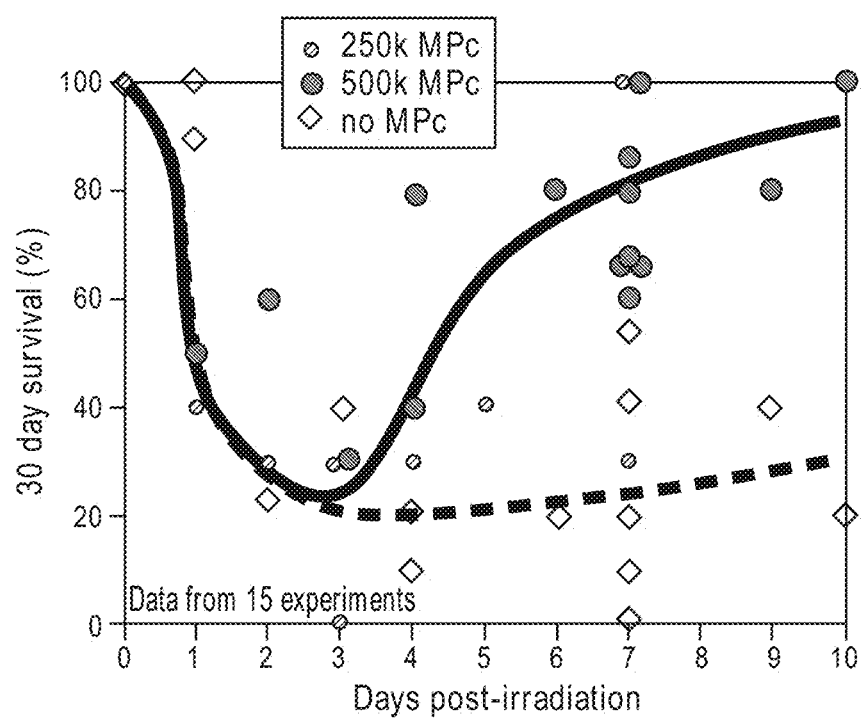
FIG. 7 shows time to effective protection using myeloid progenitors in mice.

FIG. 7 shows combines survival data from 15 separate experiments in which fungus was injected at different times after reconstitution of the lethally irradiated mice with 200 syngeneic HSC and 250,000 or 500,000 culture-derived MP. FIG. 7 shows recipients mice were able to survive fungal challenge during the first two days following irradiation; by D+3, mice were fully susceptible to infectious challenge.

Mixed Allogenic Cultured Myeloid Progenitors.

The purpose of the experiment was to determine whether mixed allogeneic MPc (i) protects to the same extend as single donor MPc (ii) does not adversely affects the mice. The experiment shows MPc in pooled batches and cryopreserved as aliquots are a clinically relevant therapeutic.

This study was modified from the standard Fungus experiments with murine MPc. The standard design is to culture C57BL/Ka HSC for 7 days in Xvivo15 supplemented with KitL, Flt3L, Tpo and IL-6. On day 0 the host mice (BALB/c) are lethally irradiated (2×4.4Gy, 4 hours apart) and injected on the same day with 5×10$^5$ cells from the MPc cultures and 200 BALB/c HSC (KLS). On day 7 the mice are injected i.v. with 150 conidia of *Aspergillus fumigatus*. The mice are inspected daily and the 30 day survival is determined.

The experiments described herein differ in that (i) HSC were sorted and cultured from BS.BA, AKR, FVB and SJL mice (ii) reduced numbers of MPc were given (iii) the fungus was given more rapid post-irradiation.

| Date | Description |
|---|---|
| Jan. 6, 2005 | Day -7. Sort BS.BA, AKR, FVB and SJL HSC to initiate 4 separate MPc cultures. |
| Jan. 13, 2005 | Day 0. Sort BALB/c HSC, harvest MPc cultures, irradiate 51 BALB/c mice and inject 45 BALB/c mice with MPc and/or HSC. |
| Jan. 20, 2005 | Day 7. Inject 45 reconstituted mice with 200 conidia of *Aspergillus fumigatus* |
| Jan. 21, 2004 to Feb. 13, 2005 | Day 8 to 30. Daily records of surviving and dying mice |
| 2005 | Test mice for level of reconstitution starting at 4 weeks |

| Group | n | HSC | BS.BA MPc | AKR/SJL/ FVB | Fungus | Day |
|---|---|---|---|---|---|---|
| HSC noMP | 15 | 200 | 0 | no | 200 conidia | 7 |
| BS.BA MPc | 15 | 200 | 500,000 | no | 200 conidia | 7 |

-continued

| Group | n | HSC | BS.BA MPc | AKR/SJL/ FVB | Fungus | Day |
|---|---|---|---|---|---|---|
| Mixed MPc | 15 | 200 | 125,000 | 125,000 each | 200 conidia | 7 |
| Radiation Ctrl | 5 | 0 | 0 | no | 0 | n/a |
| Total | 50 | 9,000 | 9,375,000 | 1,875,000 each | 9,000 | |

Hosts: BALB/c, H-$2^d$, CD90.2, CD45.2 (Charles Rivers Laboratories). Approximately 56 mice necessary, 51 as hosts and 5 as HSC-donors. MPc: C57BL/Ka, H-$2^b$, CD90.1, CD45.1 (BS.BA, bred in house); MPc:AKR, H-$2^k$, CD90.1, CD45.2 (CRL); MPc:SJL, H-$2^s$, CD90.2, CD45.1 (CRL); MPc:FVB, H-$2^q$, CD90.1, CD45.2 (CRL). Approximately 5 to 10 mice of each strain are necessary, sufficient to generate 8-10×$10^4$ HSC. More BS.BA cells are needed than the other strains.

MP-Cultures.

CD117$^+$ CD90.1$^{low}$Lin$^{neg/low}$Sca-1$^+$ HSC were sorted from CD117-enriched BS.BA, AKR and FVB bone marrow as described above. SJL HSC were sorted as CD117$^+$ Lin$^{neg/low}$Sca-1+ cells. Approximately 3×$10^4$ HSC will be used to initiate MPc cultures. The cells were cultured in Xvivo15+2ME+Pen/Strep+50 ng/ml KitL+30 ng/ml Flt3L+5 ng/ml Tpo+10 ng/ml IL-6 for 7 days as described above After 7 days in culture the cells were harvested and counted. Aliquots were analyzed. Briefly, flow cytometric analysis was performed to determine the presence of HSC, CMP, GMP, MEP and more mature cells (CD11b+, Gr-1$^+$, Ter119$^+$). Cytospins (stained with May-Grünwald/Giemsa stain) were made. Approximately 1.5×$10^7$ culture derived cells were needed for injections. Excess cells were cryopreserved for future use.

Balb/c Hsc Sort.

HSC, CD117$^+$Lin$^{neg/low}$Sca-1$^{pos}$, were sorted from 5 BALB/c mice. 10,000 HSC (200 per recipient) were needed. The sorted BALB/c HSC were mixed with culture-derived BS.BA MPc in the desired ratio's and used for injection into lethally irradiated BALB/c mice.

Fungus Injections.

The mice were injected in the tail vein with 150 conidia of *Aspergillus fumigatus* as described above. The injections will differ in that these mice will receive fungus on DAY 4 rather then the usual day 7. Other procedures, including the testing of part of the injection solution on Sabauroud-dextrose agar to quantify the number of live conidia injected, remain the same.

Figure 8:
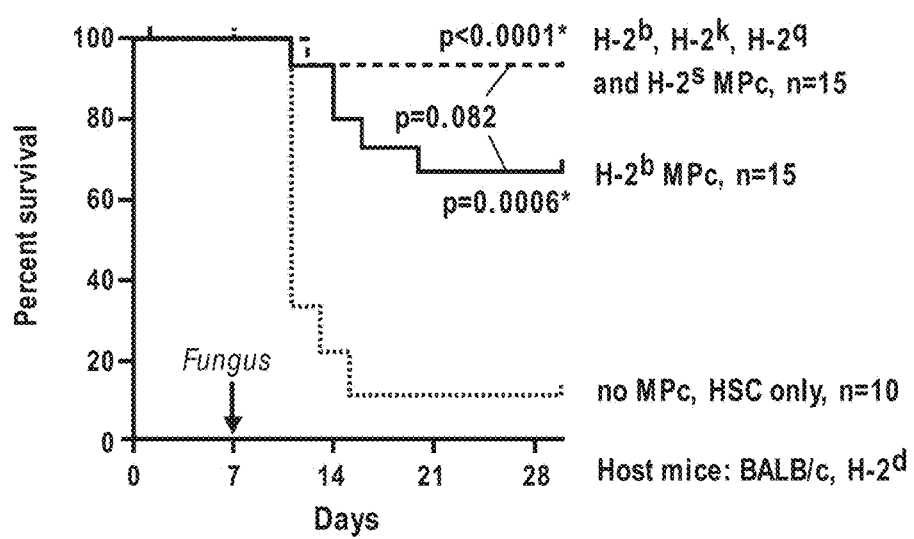
FIG. 8 shows protection of neutropenic mice by mixed allogeneic culture-derived myeloid progenitors.

FIG. 8 shows protection of neutropenic mice by mixed allogeneic culture-derived MP. The results demonstrate the effectiveness of the mixed allogeneic MP cells. The experiment used cells grown from 4 different strains, all mismatched at major and minor antigens. Mixed allogeneic frozen/thawed MP cells from 3 strains (C57BL/Ka, AKR and FVB) and at half the cell dose resulted in protection without long term reconstitution (data not shown).

Radioprotective Ability of Mismatched Allogenic Cultured Derived Progenitors.

Figures 9A, 9B:
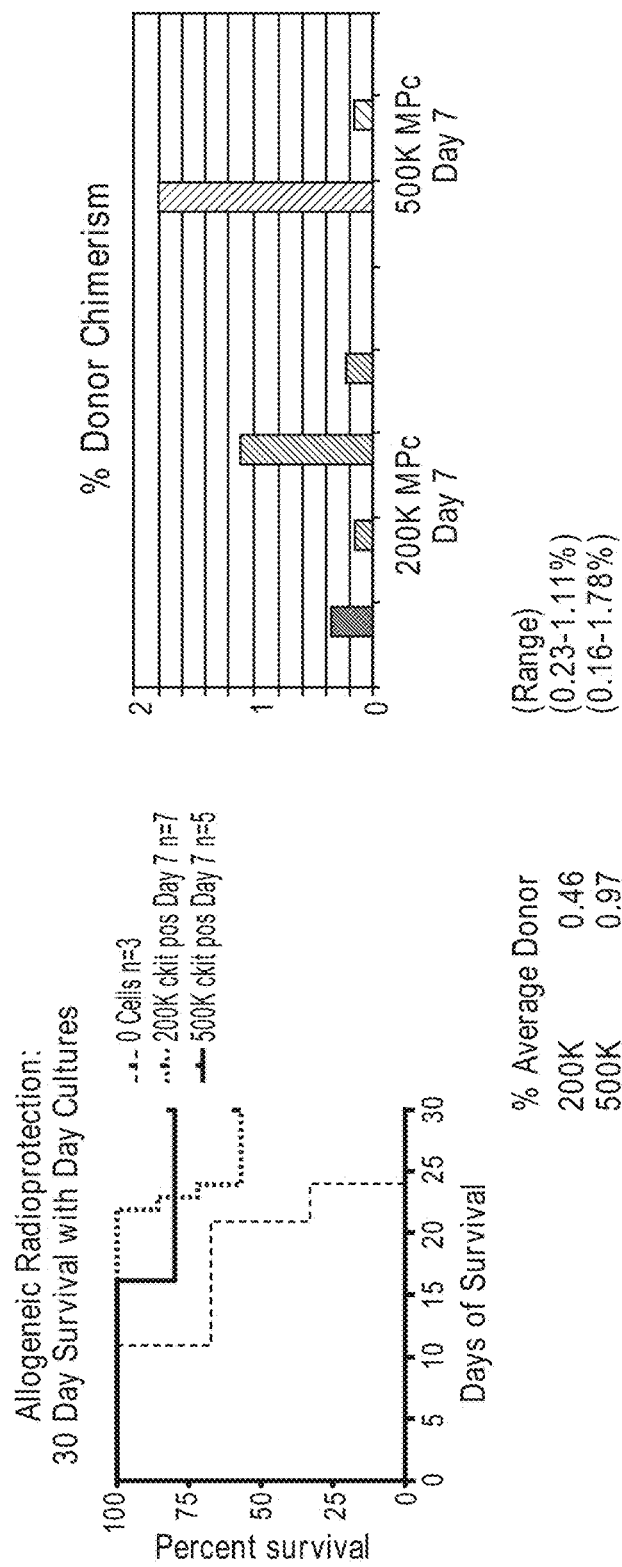
FIG. 9A-9B shows radioprotective ability of completely MHC mismatched allogeneic cultured progenitors (FIG. 9A) and detectable donor chimerism (FIG. 9B).

This experiment used AKR MPc donor and C57/B6Ka recipient. MP were either sorted directly from mouse bone marrow or derived in culture from sorted HSC. Cultured MP were derived over 7 days of culture in X-Vivo media containing KitL, Flt3L, TPO and IL-6. Following seven days of culture, cells were analyzed by FACS to determine the frequency of c-kit positive progenitor cells. A dose of cultured cells was transplanted that contained 200,000 or 500,000 c-kit positive lineage negative progenitors. FIG. 9A shows 30 day radioprotection data from lethally irradiated mice transplanted with completely MHC mismatched allogeneic MP. Surviving mice have little detectable donor chimerism (FIG. 9B)

Comparison of Radioprotective Ability of Fresh and Frozen Mismatched Allogeneic Cultured Derived Progenitors.

Figure 10:
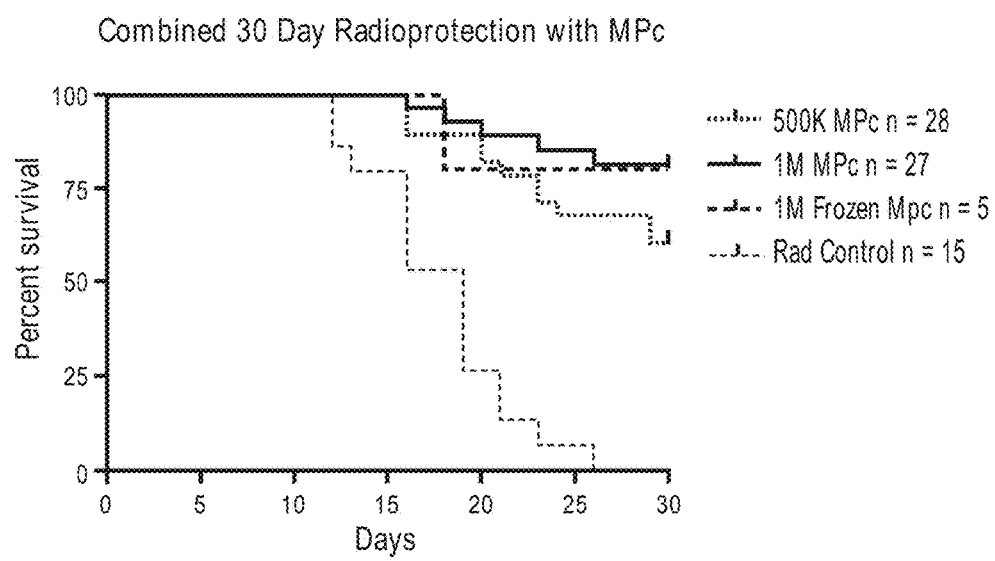
FIG. 10 shows 30 day radio protection from lethally irradiated mice transplanted with fresh and frozen completely MHC mismatched allogeneic myeloid progenitors.

This experiment used AKR MPc donor and C57/B6Ka recipient. MP were derived in culture from sorted HSC. Cultured MP were derived over 7 days of culture in X-Vivo media containing KitL, Flt3L, TPO and IL-6. Following seven days of culture, cells were harvested and analyzed by FACS to determine the frequency of c-kit positive progenitor cells. Cells were either directly injected into lethally irradiated mice or frozen and thawed prior to injection. A dose of cultured cells was transplanted that contained 200,000 c-kit positive lineage negative progenitors. FIG. 10 shows 30 day radioprotection data from lethally irradiated mice transplanted with completely MHC mismatched allogeneic MP. Cyropreserved MPs protect equivalently to MPs that are given at the time of harvest.

7.3 Example 3. Myeloid Progenitors Initiated from Human Hematopoietic Stem Cells in Flasks and Bags Human hpHSC (CD34+CD90+ cells derived from Mobilized Peripheral Blood (MPB)) were obtained from healthy volunteers. MPB is enriched for CD34+ cells using a Baxter Isolex device. CD34-enriched cells are further stained and sorted using a modified Dakocytomation MoFlo of a regular BD FACSaria to obtain CD34+CD90+ cells ("hpHSC") Cells are used either fresh or after cryopreservation, either following the Isolex CD34-enrichment or after CD34+ CD90+ sorting on the MoFlo. Samples are frozen manual or using a step rate freezer.

Freezing of Human Cells.

Cells can be frozen in a cryopreservation media that is a serum free or a serum containing mix. For all the research experiments we are using serum containing cyropreservation media. Serum containing mix: (150 ml total). 37.5 ml serum, 90 ml hetastarch, 22.5 ml DMSO. Pellet cells and resuspend cells in serum free media (IMDM or Xvivo). Prepare a metal bowl with ice and water. Place the tube of resuspended cells in the icy water and slowly drop an equal volume of the cyropreservation mix from above to the resuspended cells while gently mixing the tube. Pipet the mixture in vial and put freezing apparatus at −80 overnight and transfer vial to −180 for long storage.

Thawing of Human Cells.

Thaw the vial in 37 C bath until the content is mostly thawed Resuspend cells in serum free media (IMDM or Xvivo). Pipet cells slowly in vial containing DNAse, take out small aliquot to do initial vial cell count. Dropwise add 10 ml of Media (IMDM/DMEM etc with 10% NCS) to cells while gently rocking the tube to allow slow mixing of media and cells. Add media at approximately 1 ml/minute. Spin down cells and resuspend in staining media (HBSS/2% NCS) "rest" cells by leaving them at RT for 1/2 hour. Count/Stain or plate cells accordingly hpHSC are cultured in wells, flasks or bags in Xvivo15+ 1% Penicillin/Streptomycin, 1% Glutamax and 100 ng/ml KITL, 100 ng/ml FLT3L, 50 ng/ml TPO and 10 ng/ml IL-3, unless indicated otherwise. The cytokines base mix is rhKITL 100 ng/ml (Amgen) stock: 100 μg/ml; rhTPO 50 ng/ml (Biosource) stock: 10 μg/ml; rhFLT3L 100 ng/ml (Amgen)stock: 100 μg/ml; rhIL-3 10 ng/ml (Biosource)

stock: 10 μg/ml. In some experiments, the additive effect of the following cytokines was tested rhIL-6 10 ng/ml, rhIL-11 10 ng/ml, rhGM-CSF 10 ng/ml, rhG-CSF 100 ng/mlAssays include cell counting (trypan blue) and, typically on days 5, 8 and 11, flow cytometry (CD34, CD90, CD45RA, CD123, CD15, CD33, CD41, CD19).

Bags: 7 ml Vuelife bag (American Fluoroseal, catalog #1PF-0007), 32 ml (#2P-0032) or 72 ml (#2P-0072) were used Handling of the bags: Use standard precautions for handling human cells. The bags have one (7 ml bags) or two ports that can be used for filling and drawing samples. The ports have luer locks which allows sample lines and syringes to be connected. The 7 ml bags, once filled with more than approx. 4 ml, are under enough pressure to leak when opened, they need to be clamped shut before opening the luer lock. Use syringes to fill the bags or add more medium, gravity flow is not sufficient. The larger bags can be easily filled by gravity flow, a syringe without plunger can be connected as a "funnel" when adding medium or cells with a regular pipette. These bags do not need to be clamped prior to opening the lock, they only need to be held upright.

Culturing: The bags are typically cultured in a Sanyo incubator; 37° C., 5% $CO_2$ and 1-20% 02. The incubators are fully humidified, although this is not necessary for bag-culturing. The bags are gas-permeable, but not water permeable. The cell concentration is typically $10^5$ cells/ml (range: $10^6$ cells/ml to $10^4$ cells per ml). The bags may be placed in petri dishes (15 cm diameter, can hold 7 or 30 ml bags) or in square dishes (larger bags), for ease of handling and added sterility.

Sampling: Regular cell samples can be drawn from the bags using 1 ml syringes equipped with a luer lock. Mix the contents of the bag (cells tend to collect in creases, see grey deposits in the picture above). Clamp if necessary (7 ml bag) and remove the stopper from (one of) the ports. Attach a 1 ml syringe and invert the bag (syringe down). Remove the clamp, if present. Fill and empty the syringe a few times to mix the cells in the connecting tubes. Empty the syringe (plunger all the way down) and invert the bag (syringe up). Allow air to move up and seal the hard plastic tube of the sample port (even partially fill it), then aspire a sample into the tube. The whole of the sample tube contains approx 0.2 ml. Reclamp if necessary and remove the syringe and replace with the stopper.

In a 7 ml bag 2 ml of cells in GF containing media, at day 3 or 4 additional media was added (2-3 ml) to replenish the culture. In some experiments, in a 72 ml bag approximately $4\times10^6$ cells in 20 ml of medium (cell concentration $2\times10^5$ cells per ml). Once cell densities approach $10^6$ cells per ml (approximately day 4) the cells are diluted to keep the density between $3\times10^5$ and $2\times10^6$ cells per ml. Media may be added at days 4 and 6 (to a total volume of 72 ml) for harvest and freezing at day 8. The cells expanded to approx. $1.5\times10^8$ cells in 8 days. A schedule could be to start with 3 million cells in 15 ml, add 15 ml of medium on day 4, followed by addition of 40 ml of medium on day 6.

Figure 11B:
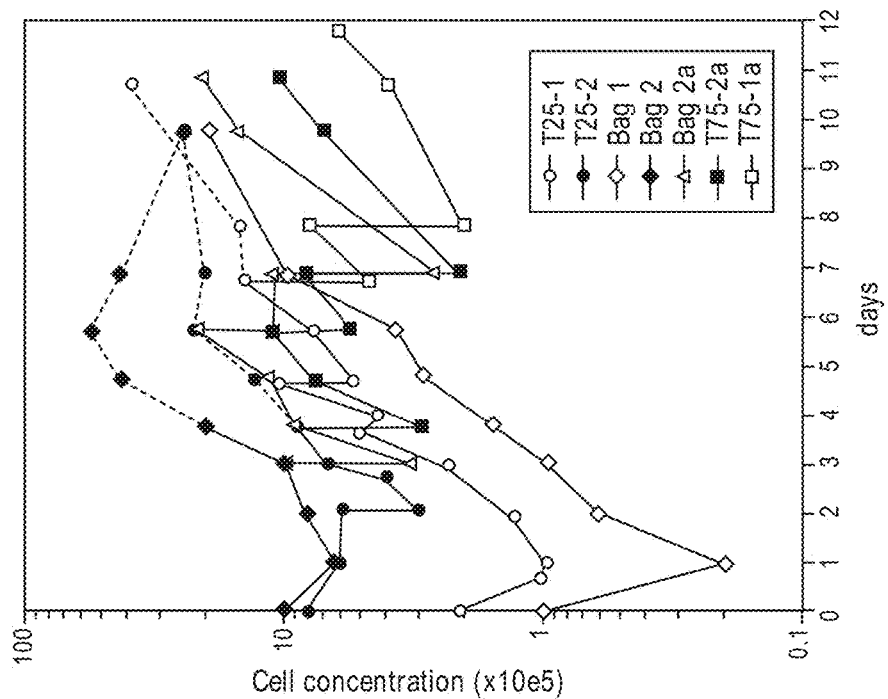
FIGS. 11A-11B shows human expansion data in 7 ml AFC bags and flasks.
Figure 11A:
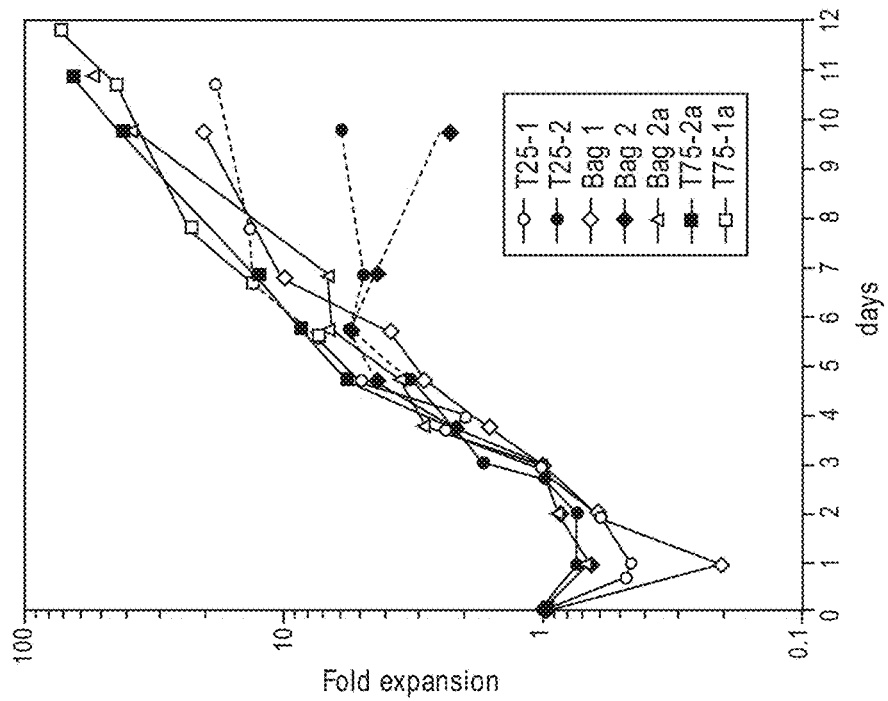

Analysis: Remove a cell sample as described above. Full analysis of the cultures are typically done on days 5, 8 and 12. This includes flow cytometric analysis, plating of 500 cells in 35 mm dishes in methylcellulose, and May-Grünwald/Giemsa stained cytospins, Cell counts are done on a daily bases using a haemocytometer and trypan blue Expansion data was obtained from 5 separate donors. FIGS. 11A-11B shows expansion data in Bags and Flasks from Donor: 1319. FIG. 11A shows total expansion, FIG. 11B shows cell density data for the cells (CD34+CD90+) from the donor, cultured in identical medium/GF (Xvivo15 supplemented with Glutamax, PenStrep, KITL, FLT3L, TPO and IL-3). The cells were cultured at different densities and in different types of bags and flasks. Starting densities between $1\times10^5$ and $1\times10^6$ cells per ml, both in 7 ml AFC bags. Dashed lines indicates cultures that did not receive any more medium, but were followed to see what the maximal densities were that could be achieved. Proliferation rates are similar between cultures growing in AFC bags and cultures growing in tissue culture flasks. A proportion of the cells adhered loosely to the plastic of the flasks, this was not the case for the Teflon bags. Phase contrast view of cells growing in flasks and bags Donor: 1319 of cultures at day 8 after plating show cells in bags tend to gather increases, explaining the greater apparent density (data not shown).

Figure 12:
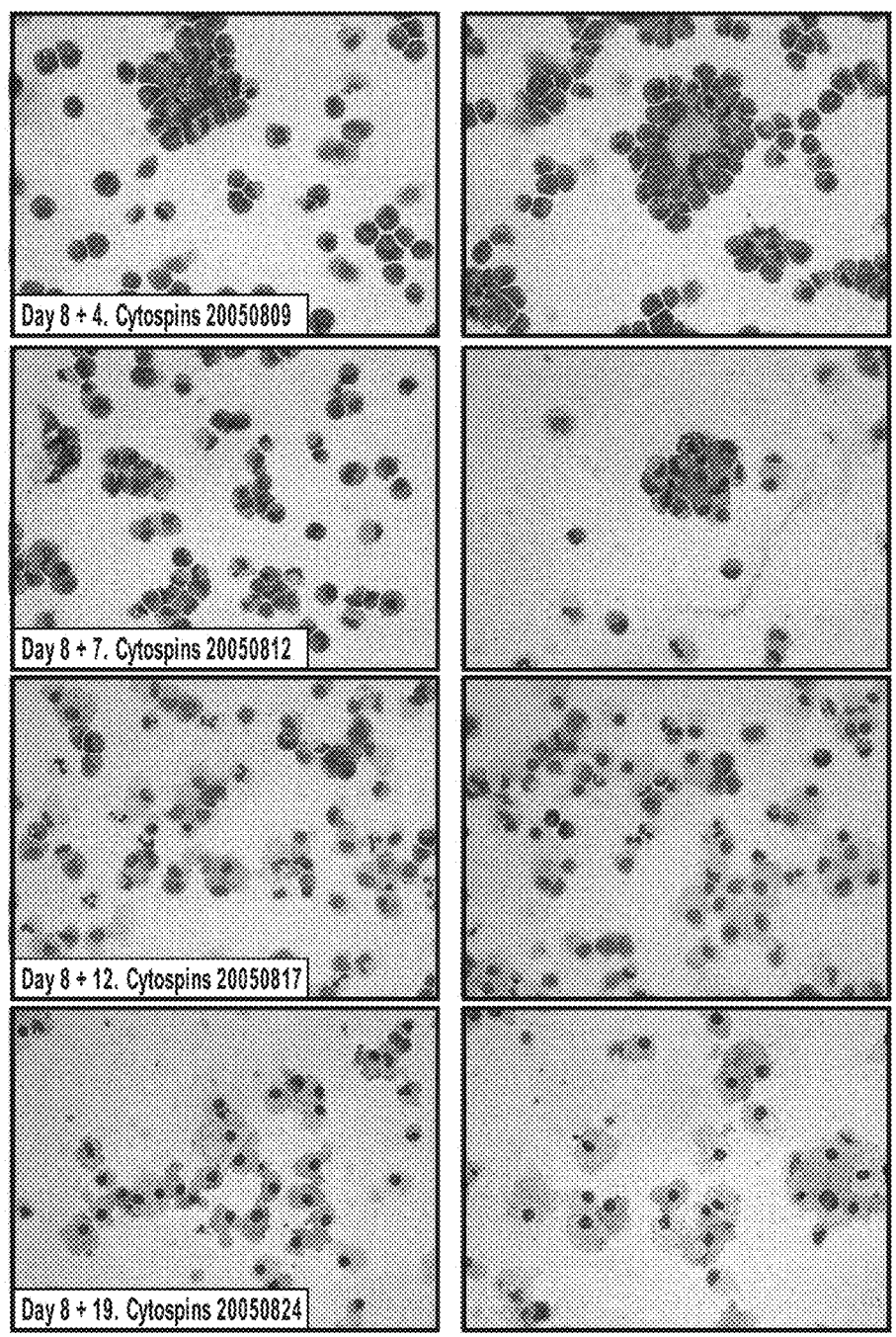
FIG. 12 shows photographs of cells from human myeloid progenitors cultures and treated with growth factors.

FIG. 12 is photographs of cells from human MP cultures and treated with growth factors. Donor: 1319, cells were cultured in flasks for 8 days (Xvivo15+PenStrep, Glutamax, 100 ng/ml KITL, 100 ng/ml FLT3L, 50 ng/ml TPO and 10 ng/ml IL-3, switched to T25 flasks with different growth factors (100 ng/ml KITL, 20 ng/ml IL-3 and 300 ng/mlG-CSF). FIG. 12 shows cells at different timepoints after transfer (4 to 19 days). The presence of granulocytes peaks at day 12, by day 19 only macrophages are seen. Human MP cultures can differentiate into morphologically mature neutrophils and macrophages, as well as megakaryocytes.

Figures 13A, 13B:
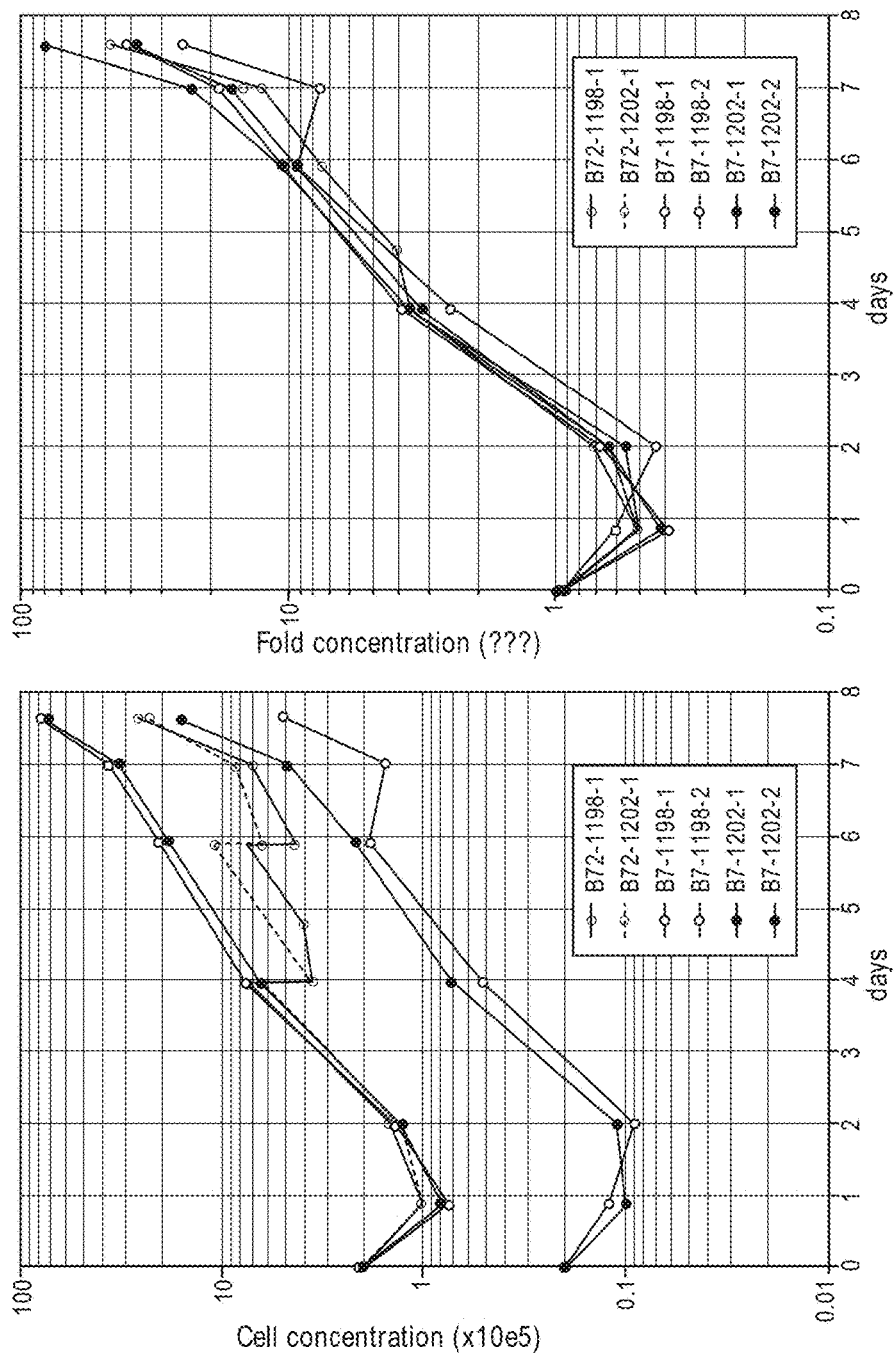
FIG. 13A-13B shows human expansion data in 7 ml AFC bags.
Figure 14B:
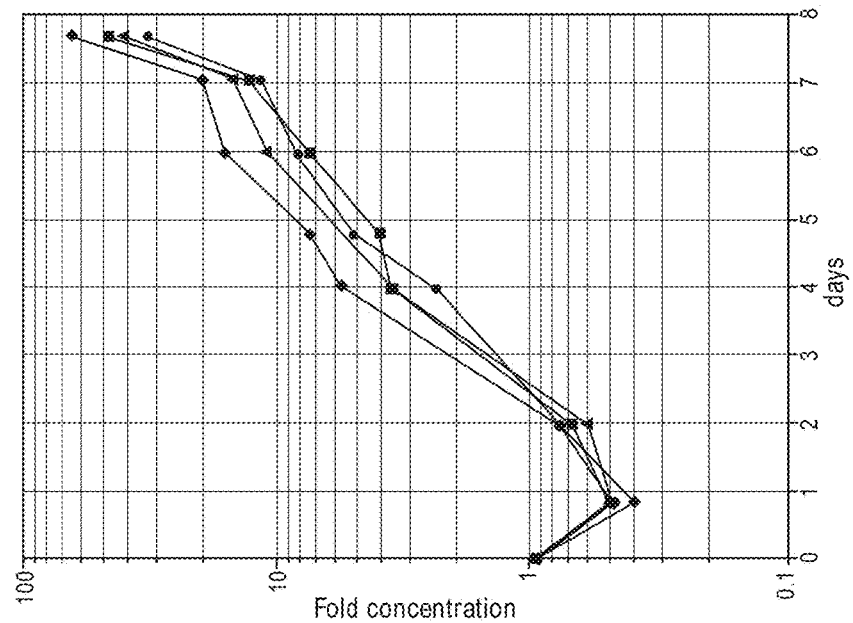
FIG. 14A-14B shows human expansion data in 72 ml AFC bags.
Figure 14A:
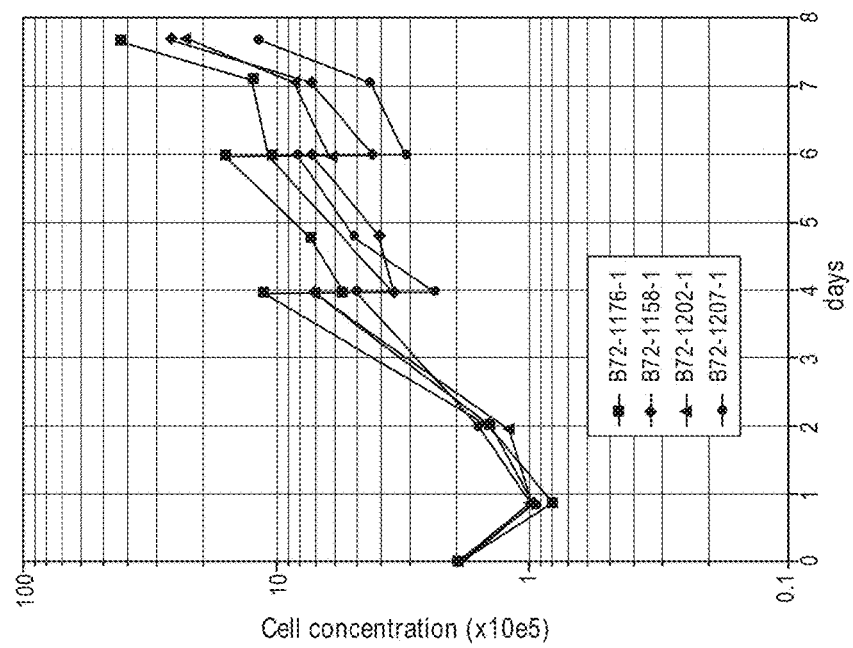

Expansion data in bags from Donors 1198 and 1202. Cells from these two donors were Isolex enriched, sorted for the hpHSC phenotype (CD34$^+$ CD90$^+$) using the Dakocytomation MoFlo and cryopreserved post sorting. The cells were thawed and plated in 7 ml AFC bags as indicated. Medium: Xvivo15 supplemented with Glutamax, PenStrep, KITL, FLT3L, TPO and IL-3. FIG. 13A shows total expansion, and FIG. 13B shows cell density data. Open symbols indicate cells plated at the same time in larger bags (see below). No difference is apparent between cells plated at $2\times10^4$ cells per ml and cells plated at $2\times10^5$ cells per ml, or between cells plated in 7 ml versus 72 ml AFC bags Expansion data in bags from Donors 1176, 1198, 1202 and 1207 in 72 ml AFC bags. Cells from these four donors were Isolex enriched, sorted for the hpHSC phenotype (CD34$^+$ CD90$^+$) using the Dakocytomation MoFlo and cryopreserved post sorting. The cells were thawed and plated in 72 ml AFC bags as indicated. Medium: Xvivo15 supplemented with Glutamax, PenStrep, KITL, FLT3L, TPO and IL-3. FIG. 14A shows total expansion, and FIG. 14B shows cell density data for the cells. Initial plating volume: approx. $4\times10^6$ cells in 20 ml, final culture volume 70 ml per bag. A total of $15.6\times10^6$ cells were plated in the 4 bags, a total of $6.14\times10^8$ cells were harvested (and cryopreserved) after 8 days. Average expansion 40-fold (range 30-fold to 60-fold).

Figures 15A, 15B:
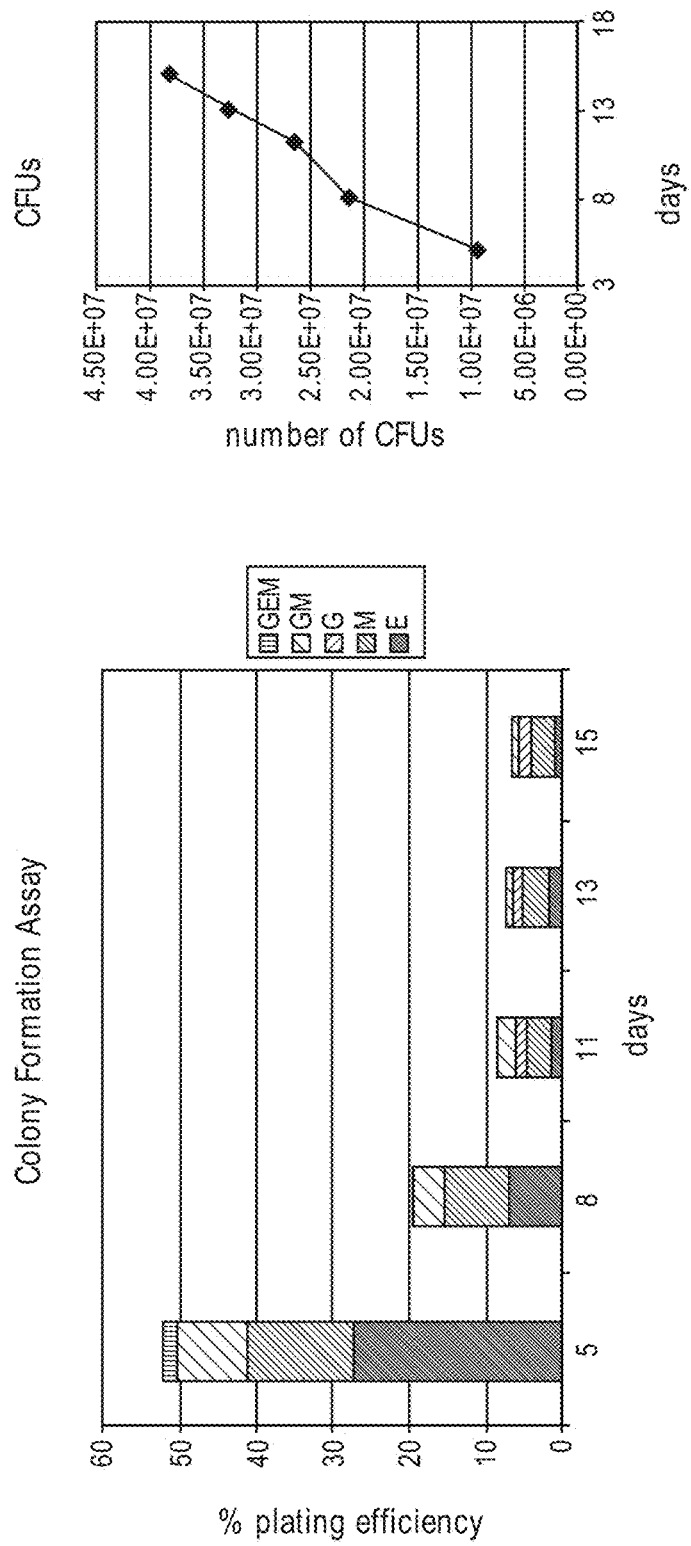
FIG. 15A-15B shows colony formation of human myeloid progenitors.

7.4 Example 4. Human Myeloid Progenitors Colony Formation and Response to G CSF In Vivo Human myeloid progenitor culture were started with $2\times10^6$ purified human HSC (thawed hpHSC) and cultured in a static AFC bag with serum-free ExVivo-15 with SCF, Flt3L, TPO, IL-3 as described above. At day 5, 8, 11, 13 and 15 the MP cells were harvested and plated in triplicates into methyl cellulose to assess their potential to form colonies in vitro. FIG. 15A shows the plating efficiency (colonies obtained/cells plated) subdivided into the different types of colonies (E: erythroid; M: macrophage; G: granulocyte;

GM: mixed granulocyte/macrophage; GEM: mixed myeloid/erythroid), indicating how many progenitors are present in cultures.

FIG. 15B shows the increase of total numbers of CFU (colony forming units) which is the plating efficiency times total cell count. Although the relative numbers of CFU go down due to the relative stronger increase in total cell number, there is an increase in CFU over time.

Figure 16:
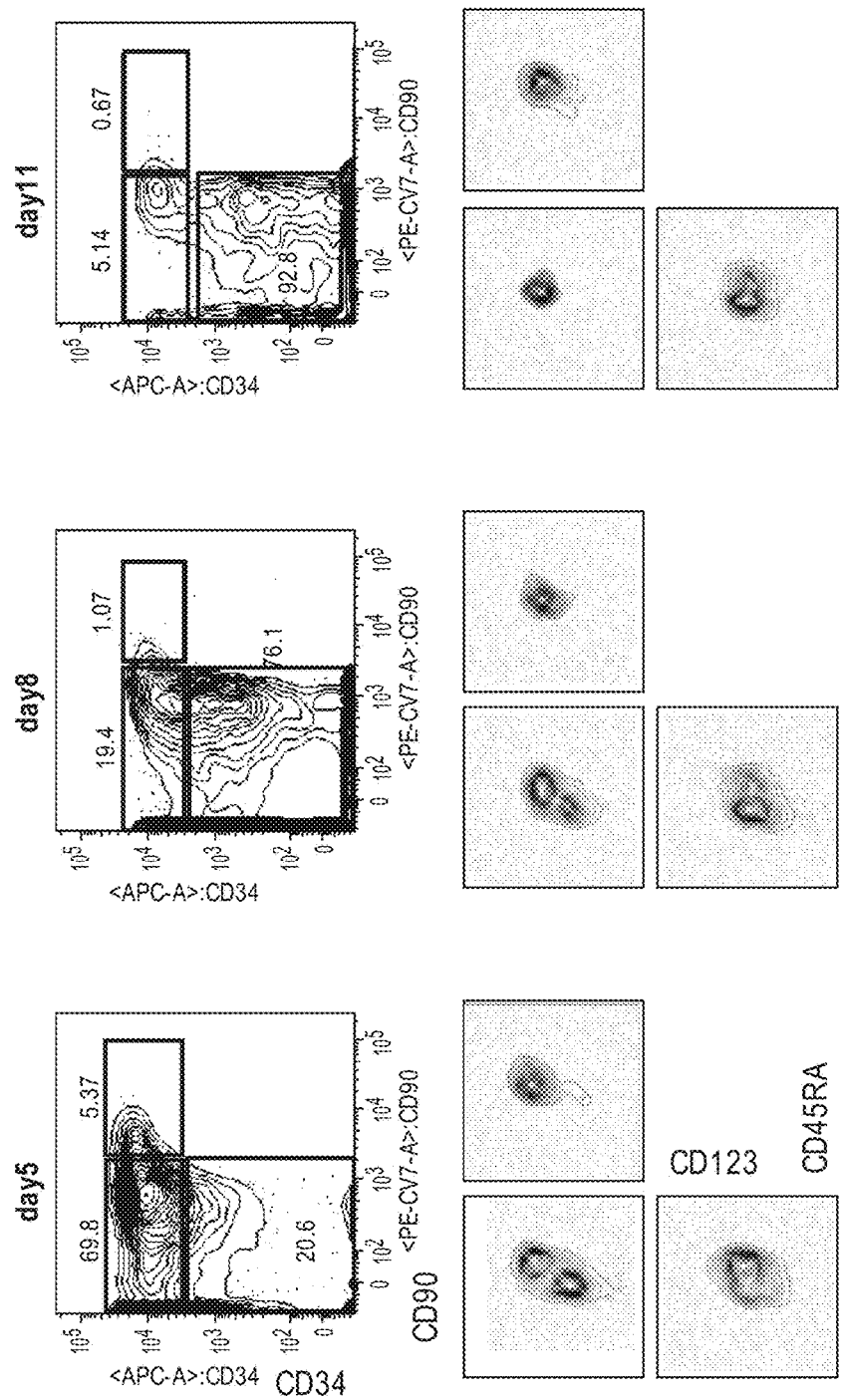
FIG. 16 shows FACS analysis of human myeloid progenitors cultures for stem and progenitor populations.

FACS analysis of cultured MP and changes in the stem/progenitor populations over time are shown in FIG. 16. Plots shown are pregated on live and lineage negative cells. The starting population at day 0 is CD34+CD90+(upper right gate) and this population declines over time. Myeloid progenitors are mainly in the CD34+CD90− gate (upper left), additional data indicates the CD34low/− cells make colonies (although to a lower degree) and therefore contribute to the overall progenitor pool (data not shown). The relative number of CD34+CD90− cells against the relative plating efficiency over time was determined (data not show) to determine the correlation between % CD34+ cells and CFUs. The close correlation (data not shown) suggest that CD34 FACS stains can be used as an indicator for the number of progenitors in cultures.

FIG. 17A-17B show the effect of IL-3 and IL-6, alone and in combination on human MP cells. FIG. 17A shows cell density and cell count per ml and FIG. 17B show the total cell counts. Human cells were cultured in Xvivo containing SCF/Flt3L/TPO and the IL-3/IL-6 (10-20 ng/ml) were added alone or in combination (10-20 ng/ml). The cell counts reveal that IL-3 acts as a proliferation factor in the cultures.

Figures 18A, 18B, 18C:
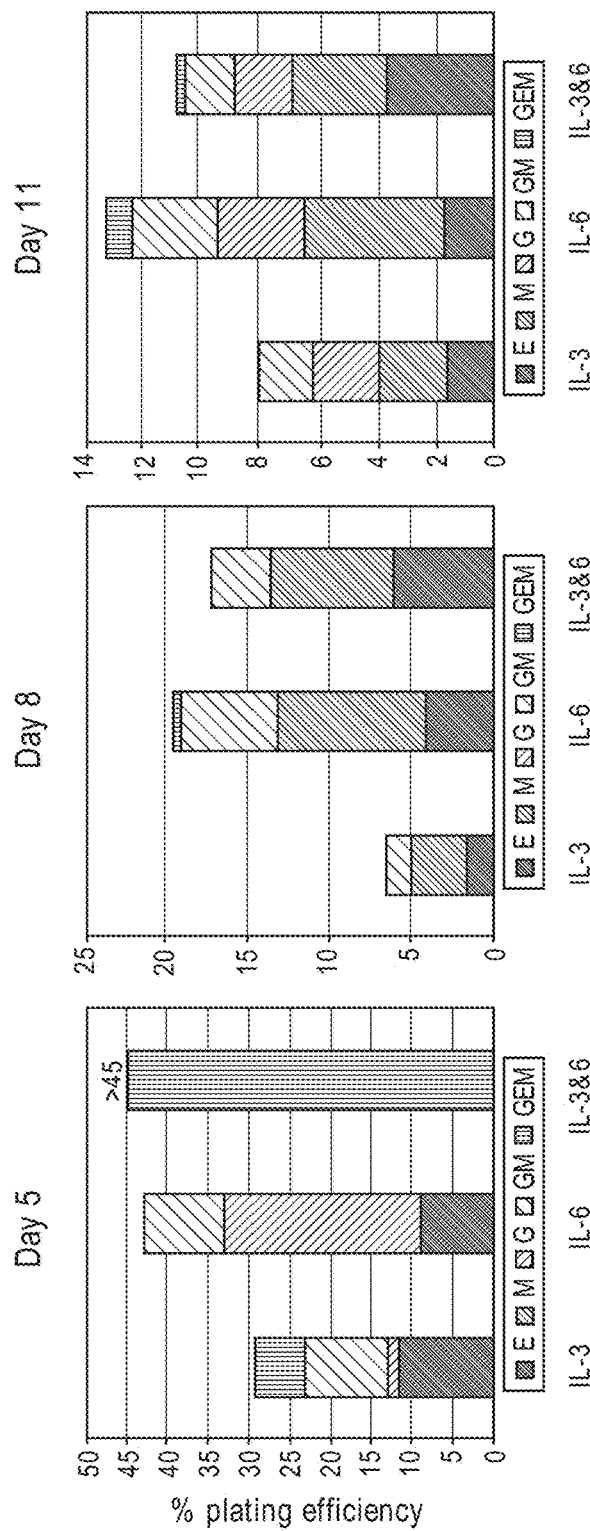
FIG. 18A-18C shows a result of a colony formation assay of the myeloid progenitors cultures with IL-3, IL-6 or in combination.

FIG. 18A-18C show a result of a colony formation assay of the MP cells cultured with IL-3, IL-6 or both in combination. FIG. 18A (day 5), FIG. 18B (day 8), and FIG. 18C (day 11) demonstrates that addition of IL-6 increases the numbers of CFU and helps to maintain progenitor potential of MP cells.

Figure 19:
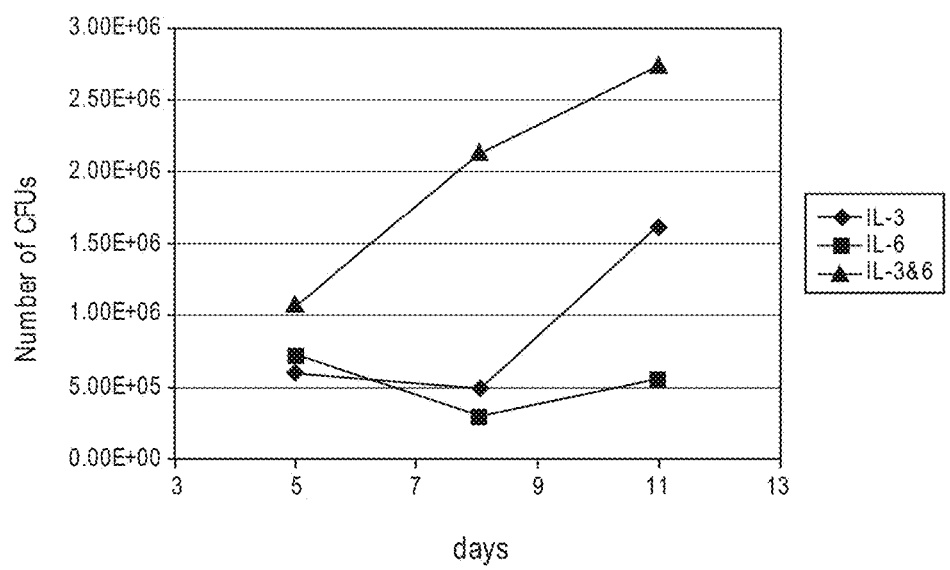
FIG. 19 show the absolute numbers of CFUs in myeloid progenitors cultures with IL-3, IL-6 or in combination.

FIG. 19 show the absolute numbers of CFUs in MP cultures with IL-3, IL-6 or both in combination. Comparison of the total numbers of CFU from MPc in response to IL-3 and/or IL-6. The proliferate effects of IL-3 and the progenitor maintaining effects of IL-6, these two cytokines in combination increase the total numbers of colony initiating cells in the cultures.

Figure 20B:
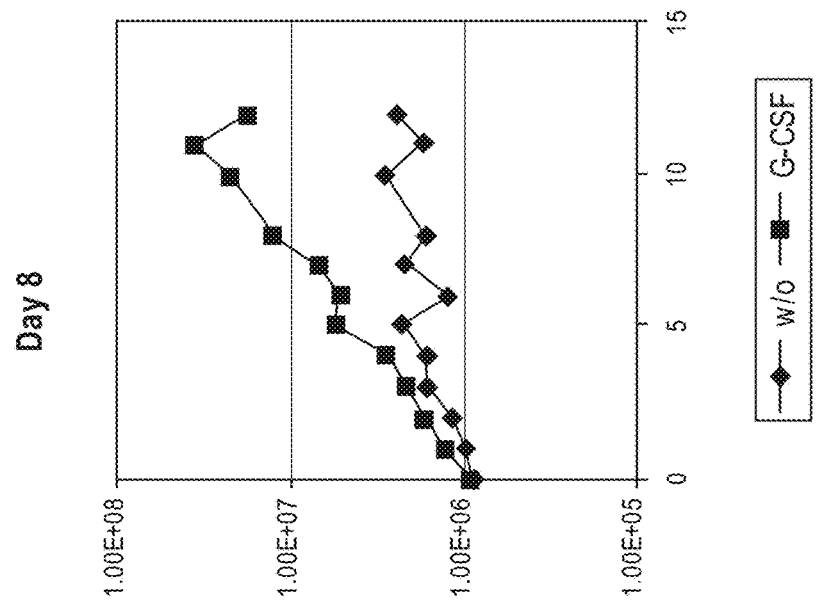
FIG. 20A-20B shows responsiveness of human myeloid progenitors cells towards G-CSF.
Figure 20A:
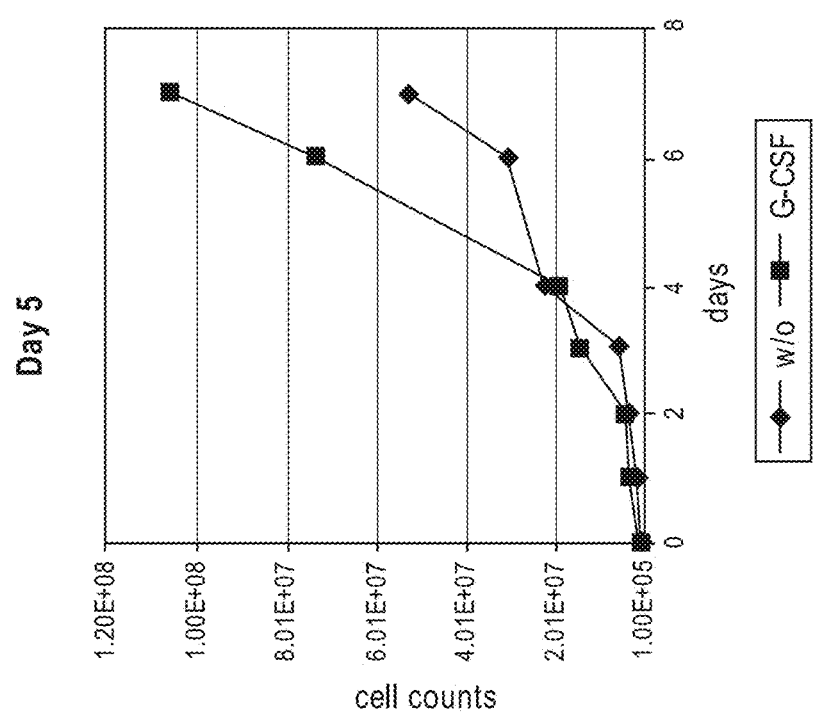

MPc were culture under standard conditions for 5 (FIG. 20A) or 8 days (FIG. 20B). G-CSF was added 300 ng/ml was added at day 5 or 8 MPc (day zero on graphs) to the medium and the cell growth monitored over time and compared to control cultures, which did not receive G-CSF (w/o). The data shows that G-CSF can be used to increase cell numbers over long period of times when added at later stages to the cultures. It also shows that our MP are responsive to G-CSF and are likely to be direct progenitors of granulocytes/neutrophilesm and suggests G-CSF in combination with MPc transplant to increase neutrophils numbers in patients.

Figure 21:
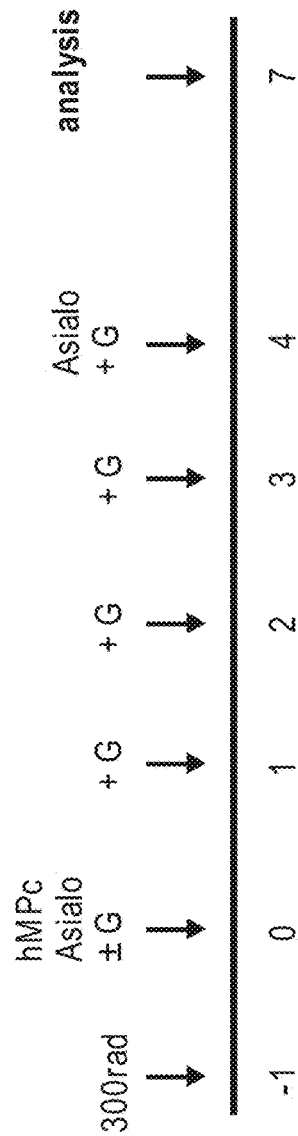
FIG. 21 is a schematic to show responsiveness of human myeloid progenitors cells to G-CSF in vivo.

FIG. 21 is a schematic to show responsiveness of human MP cells to G-CSF in vivo. The scheme shows a transplantation experiment of day 8 MPc into NOD/SCID mice to evaluate their potential to engraft, developmental potential and response to G-CSF in vivo.

Figure 22:
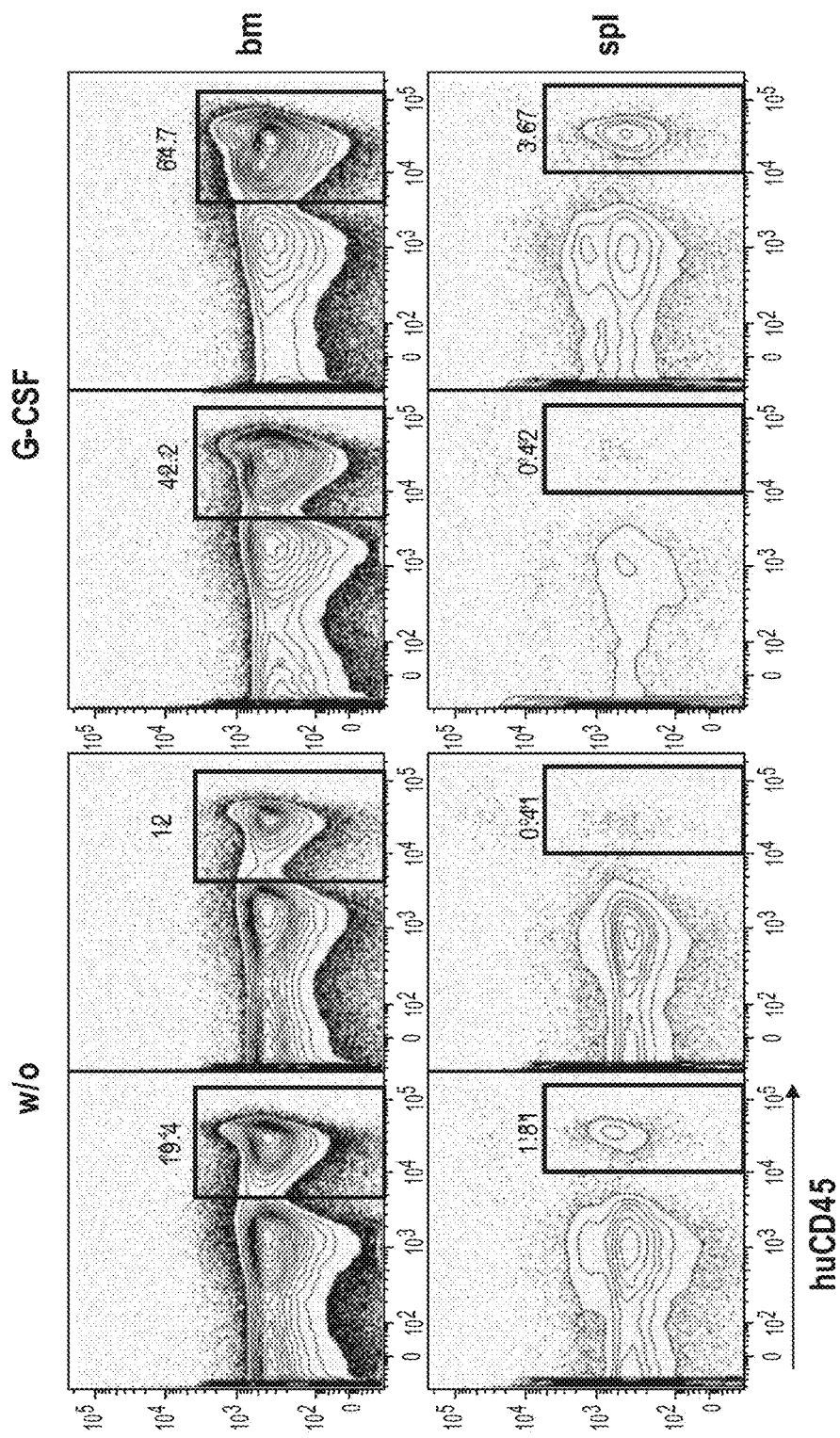
FIG. 22 is FACS analysis of mouse bone marrow and spleen showing engraftment of human MPc one week after transplantation and their response to G-CSF.

FIG. 22 is FACS analysis of bone marrow and spleen to look for engraftment of human MPc one week after transplantation and their response to G-CSF. Samples were stained with anti-human CD45 antibody to detect donor cells and shown are two independent samples for each tissue with/without G-CSF. Bone marrow shows highest degree of reconstitution, which can be increased by injection of G-CSF.

Figure 23:
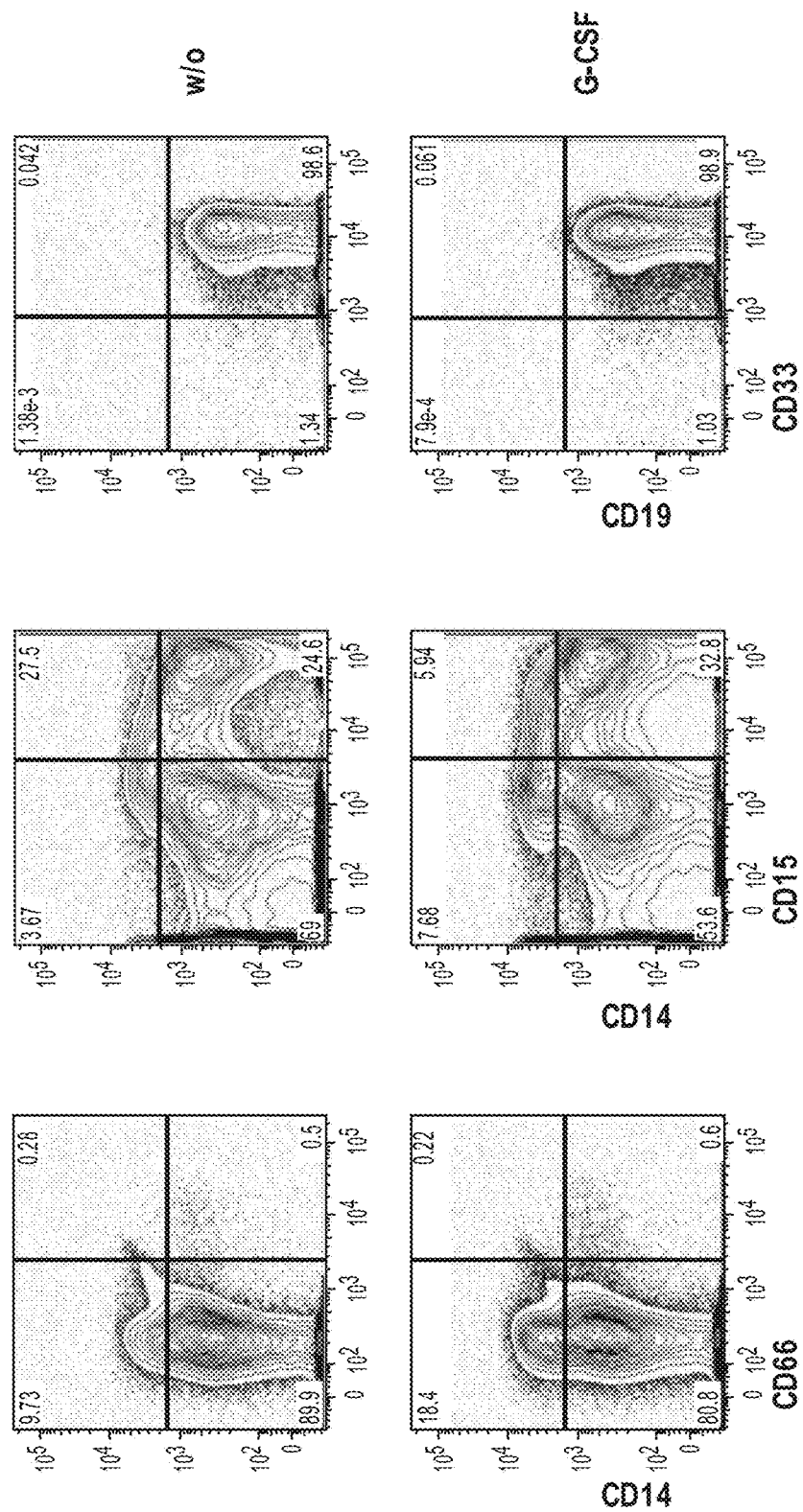
FIG. 23 is FACS phenotype of the human culture-derived myeloid progenitors in NOD/SCID mice.

FIG. 23 is FACS phenotype of the human MPc derived cells in NOD/SCID mice. Plots shown are pregated on live and huCD45+ cells. CD33 is a marker for early myeloid cells and the majority or the human cells are CD33+ indicates that most cells are committed to that lineage. CD14 and CD15 stain more mature myeloid cells and heterogeneous staining shows commitment and maturation into the myeloid lineage. At the same time no human B cells (CD19) or T cells (CD3, not shown) were detectable at that time.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

All patents, patent applications, publications, and references cited herein are expressly incorporated by reference to the same extent as if each individual publication or patent application was specifically and individually indicated to be incorporated by reference.

What is claimed is:

1. A method of improving impaired hematopoiesis in a human, comprising,
   administering to the human a composition comprising human allogeneic myeloid progenitor cells derived from multiple unrelated donors in an amount sufficient to improve hematopoiesis in the human, wherein there is at least a partial mismatch at a major histocompatability complex (MHC) gene between the donors and the human.

2. The method of claim 1, wherein the composition has less than 10% hematopoietic stem cells (HSCs).

3. The method of claim 1, wherein human allogeneic myeloid progenitor cells are expanded human allogeneic myeloid progenitor cells.

4. The method of claim 1, wherein the myeloid progenitor cells comprise common myeloid progenitor cells.

5. The method of claim 1, wherein myeloid progenitor cells in the composition are at least 25% of total cells in the composition.

6. The method of claim 1, wherein the human is undergoing hematopoietic stem cell (HSC) transplantation.

7. The method of claim 6, wherein the myeloid progenitor cells are administered after the HSC transplantation.

8. The method of claim 6, wherein the myeloid progenitor cells are administered concurrently with HSC transplantation.

9. The method of claim 1, wherein the human is neutropenic.

10. The method of claim 1, wherein the human is suffering from thrombocytopenia.

11. The method of claim 10, wherein the myeloid progenitor cells are administered adjunctively with a therapeutic composition for treating complications associated with thrombocytopenia.

12. The method of claim 11, wherein the therapeutic composition comprises a platelet preparation.

13. The method of claim 11, wherein the therapeutic composition comprises EPO.

14. The method of claim 1, wherein the myeloid progenitor cells are expanded from cells obtained from peripheral blood.

15. The method of claim 1, wherein the myeloid progenitor cells are expanded from cells obtained from bone marrow.

16. The method of claim 1, wherein the myeloid progenitor cells are expanded from cells obtained from umbilical cord blood or placental cord blood.

17. The method of claim 1, wherein the human has been previously treated with or exposed to a myeloablative agent.

18. The method of claim 17, wherein the myeloablative agent is ionizing radiation.

19. The method of claim 1, wherein prior to the administering, the human allogeneic myeloid progenitor cells derived from multiple unrelated donors are frozen and subsequently thawed.

20. The method of claim 1, wherein the cells are delivered by intravenous infusion.

* * * * *

UNITED STATES PATENT AND TRADEMARK OFFICE
CERTIFICATE OF CORRECTION

PATENT NO. : 10,260,044 B1
APPLICATION NO. : 16/155598
DATED : April 16, 2019
INVENTOR(S) : Timothy C. Fong, Adrianus Geertrudis Wilhelmus Domen and Julie Lynne Christensen Page 1 of 1

It is certified that error appears in the above-identified patent and that said Letters Patent is hereby corrected as shown below:

On the Title Page

Item (73) Assignee, delete "Therapeutic" and insert -- Therapeutics --

Signed and Sealed this
Twenty-fifth Day of February, 2020

Andrei Iancu
*Director of the United States Patent and Trademark Office*